US012729192B2

(12) United States Patent
Peng et al.

(10) Patent No.: US 12,729,192 B2
(45) Date of Patent: Sep. 8, 2026

(54) CDK9 INHIBITOR AND USE THEREOF

(71) Applicant: PHARMABLOCK SCIENCES (NANJING), INC., Nanjing (CN)

(72) Inventors: Zuozhong Peng, Nanjing (CN); Jilin Jia, Nanjing (CN); Jiaqi Hu, Nanjing (CN); Qian Cui, Nanjing (CN); Yizhou Wu, Nanjing (CN); Yunfei Yi, Nanjing (CN); Qiuhong Chen, Nanjing (CN); Jie Wang, Nanjing (CN)

(73) Assignee: PHARMABLOCK SCIENCES (NANJING), INC., Nanjing (CN)

( * ) Notice: Subject to any disclaimer, the term of this patent is extended or adjusted under 35 U.S.C. 154(b) by 627 days.

(21) Appl. No.: 18/019,984

(22) PCT Filed: Aug. 6, 2021

(86) PCT No.: PCT/CN2021/111073

§ 371 (c)(1),
(2) Date: Feb. 6, 2023

(87) PCT Pub. No.: WO2022/028556

PCT Pub. Date: Feb. 10, 2022

(65) Prior Publication Data

US 2023/0271942 A1 Aug. 31, 2023

(30) Foreign Application Priority Data

Aug. 7, 2020 (CN) ........................ 202010789162.3

(51) Int. Cl.

| | |
|---|---|
| ***C07D 401/14*** | (2006.01) |
| ***C07D 401/12*** | (2006.01) |
| ***C07D 417/14*** | (2006.01) |
| ***C07D 471/04*** | (2006.01) |
| ***C07D 487/04*** | (2006.01) |

(52) U.S. Cl.

CPC ......... *C07D 401/14* (2013.01); *C07D 401/12* (2013.01); *C07D 417/14* (2013.01); *C07D 471/04* (2013.01); *C07D 487/04* (2013.01)

(58) Field of Classification Search

CPC .. C07D 401/14; C07D 401/12; C07D 417/14; C07D 471/04; C07D 487/04; C07D 213/81; C07D 213/74; A61P 35/00

See application file for complete search history.

(56) References Cited

FOREIGN PATENT DOCUMENTS

| | | | | |
|---|---|---|---|---|
| CN | 101568529 | A | | 10/2009 |
| CN | 102143953 | A | | 8/2011 |
| CN | 103562184 | A | | 2/2014 |
| CN | 104822380 | A | | 8/2015 |
| EP | 2361902 | A1 | | 8/2011 |
| EP | 2589592 | A1 | * | 5/2013 |
| EP | 3176154 | A1 | | 6/2017 |
| EP | 3036231 | B1 | | 2/2020 |
| JP | 2008542219 | A | | 11/2008 |
| JP | 2009511555 | A | | 3/2009 |
| JP | 2010514689 | A | | 5/2010 |
| JP | 2016506368 | A | | 3/2016 |
| JP | 2020507612 | A | | 3/2020 |
| WO | WO-2005113494 | A2 | * | 12/2005 .............. A61P 35/00 |
| WO | 2008034600 | A1 | | 3/2008 |
| WO | 2008079933 | A2 | | 7/2008 |
| WO | 2009118567 | A2 | | 10/2009 |
| WO | 2010051781 | A1 | | 5/2010 |
| WO | 2012117059 | A1 | | 9/2012 |
| WO | 2012126181 | A1 | | 9/2012 |
| WO | 2018106643 | A1 | | 6/2018 |
| WO | 2019154177 | A1 | | 8/2019 |

OTHER PUBLICATIONS

Le Manach et al (J Med Chem; 2018, 61:9371-9385) (Year: 2018).*

International Search Report for PCT/CN2021/111073, 8 pages, dated Nov. 10, 2021.

Gao, J , et al., "Discovery of novel 5-fluoro-N2, N4-diphenylpyrimidine-2, 4-diamines as potent inhibitors against CDK2 and CDK9", MedChemComm 6 (3), 444-454, DOI: 10.1039/C4MD00412D, 31 pages (2014).

Hole, A , et al., "Comparative structural and functional studies of 4-(thiazol-5-yl)-2-(phenylamino)pyrimidine-5-carbonitrile CDK9 inhibitors suggest the basis for isotype selectivity", J Med Chem 56 (3), 660-670, DOI: 10.1021/m301495v, 39 pages (2012).

Wang, S , et al., "Discovery and Characterization of 2-Anilino-4-(Thiazol-5-yl)Pyrimidine Transcriptional CDK Inhibitors as Anti-cancer Agents", Chemistry & Biology 17, 1111-1121, 11 pages (2010).

EP Search Report for EP Application No. 21853057.4, 13 pages, dated Sep. 30, 2024.

Cas Registry , RN 2058729-58-9 (2017) and RN1054040-45-7 (2008), 2 pages.

(Continued)

*Primary Examiner* — Rayna Rodriguez

(74) *Attorney, Agent, or Firm* — Viksnins Harris Padys Malen LLP

(57) ABSTRACT

Provided are a compound of formula (I) or a tautomer, a mesomer, a raceme, an enantiomer, a diastereoisomer, or a pharmaceutically acceptable salt thereof, and the use thereof in the preparation of drugs for diseases mediated by CDK9.

(I)

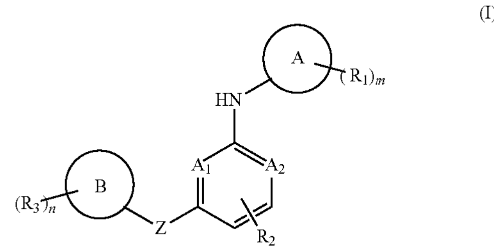

8 Claims, No Drawings

Specification includes a Sequence Listing.

(56) References Cited

OTHER PUBLICATIONS

Japanese Office Action , for JP Patent Application No. 2023-507896, 3 pages, dated Feb. 1, 2024.
Australian Office Action for AU Application No. 2021323245, 11 pages, dated Jul. 20, 2023.
CAS Registry , No. 2217237-20-0, 1 page, dated Apr. 22, 2018.
CAS Registry , No. 2394630-39-6, 1 page, dated Dec. 19, 2019.
CAS Registry , No. 2395739-84-9, 1 page, dated Dec. 20, 2019.

* cited by examiner

CDK9 INHIBITOR AND USE THEREOF

CROSS-REFERENCE TO RELATED APPLICATION(S)

This patent application claims the benefit of priority of Chinese Patent Application No. 202010789162.3, filed on Aug. 7, 2020.

SEQUENCE LISTING

The instant application contains a Sequence Listing which has been submitted electronically in ASCII format and is hereby incorporated by reference in its entirety. Said ASCII copy, created on Jun. 3, 2026, is named 17050014US1.txt and is 1440 bytes in size.

TECHNICAL FIELD

The present application belongs to the field of chemical medicine and, in particular, to a CDK9 inhibitor and a use thereof.

BACKGROUND

Cyclin-dependent kinases (CDKs) are serine-threonine protein kinases associated with various cyclin subunits. There are more than 20 members in the CDK kinase family, wherein CDK1, CDK2, CDK3, CDK4, and CDK6 are considered as cell cycle regulators and CDK7, CDK8, CDK9, and CDK11 are considered as transcription factors. Thus, CDKs participate in multiple key physiological processes including cell cycle control, cell apoptosis, neuronal physiology, and the regulation of differentiation and transcription. Considerable research evidence shows that CDKs play a key role in the development and progression of various diseases such as cancer, cardiovascular diseases, inflammatory diseases, neurodegenerative diseases, and viral diseases and thus become a very effective drug target for the research and development of innovative drugs for these associated diseases.

Cyclin-dependent kinase 9 (CDK9) participates in the formation of a positive transcription elongation factor (P-TEFb) and plays a key role in an RNA transcription regulation process. Especially for proteins having a relatively short intracellular half-life and rapidly degraded, the kinase activity of CDK9 is inhibited to inhibit the gene transcription necessary for the synthesis of these proteins, thereby down-regulating the intracellular expression level of these proteins. cMYC oncoproteins and Mcl-1 anti-apoptotic proteins expressed by a key oncogene cMYC and an important cell apoptosis suppressor gene Mcl-1 play key roles in promoting the survival and proliferation of various tumor cells. Thus, CDK9 has become an important target for cancer treatment, which has received wide attention.

In an early stage, the researches on CDK inhibitors mainly focused on the research and development of non-selective CDK inhibitors (Journal of China Pharmaceutical University, 2017, 2, 233-241). However, non-selective inhibitors generally have a strong inhibitory effect on a first type of CDK kinase for cell cycle regulation and thus have an obvious inhibitory effect on the normal division of non-tumor cells. In clinical researches, the non-selective CDK inhibitors exhibit relatively high toxicity and easily cause side effects. Therefore, it is necessary to study selective CDK inhibitors so as to have better selectivity and better druggability to reduce toxicity and adverse effects.

Currently, two CDK9-selective drugs are in the clinical research stage. One drug is AZD4573 (WO2017001354A1) from AstraZeneca, which is in clinical stage I to undergo clinical researches for blood tumor (NCT03263637). The other drug is BAY1251152 from Bayer, which is also in clinical stage I to undergo clinical researches for blood tumor (NCT02745743) and solid tumor (NCT02635672).

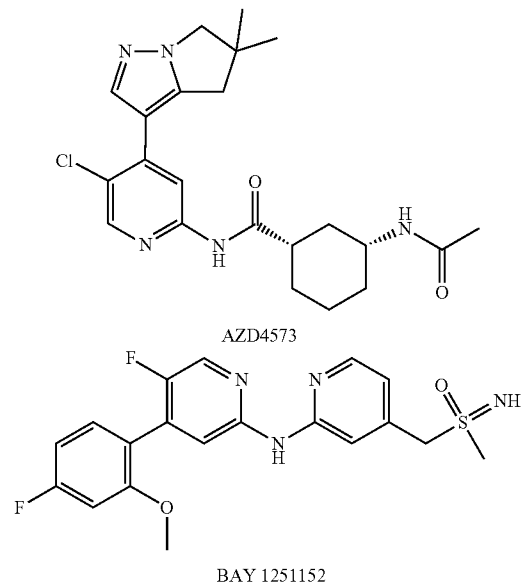

AZD4573

BAY 1251152

More researches are still required on CDK9 selective inhibitors to provide candidate compounds having good activity and selectivity.

SUMMARY

The present application discloses a compound usable as a CDK9 selective inhibitor and a use of the compound for preparing a drug for the prevention or treatment of a CDK9-mediated disease.

In one aspect, the present application provides a compound represented by general Formula (I):

(I)

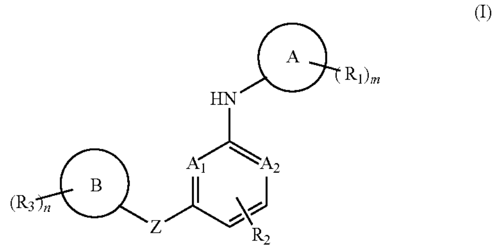

or a tautomer, a mesomer, a racemate, an enantiomer, a diastereomer, or a pharmaceutically acceptable salt thereof; wherein the ring A is 5- to 10-membered heteroaryl containing 1 to 3 heteroatoms;

the ring B is cycloalkyl or 5- to 10-membered heterocycloalkyl containing 1 to 3 heteroatoms;

$A_1$ and $A_2$ are each independently selected from C or N;

Z is selected from —C(O)—, —$CH_2$—, —$S(O)_2$—, —NH—, or —C(O)NH—;

$R_1$ is selected from hydrogen, $C_1$ to $C_6$ alkyl, $C_2$ to $C_6$ alkenyl, $C_2$ to $C_6$ alkynyl, halogenated $C_1$ to $C_6$ alkyl, halogenated $C_2$ to $C_6$ alkenyl, halogenated $C_2$ to $C_6$ alkynyl, halogen, cyano, nitro, $—C(O)NR_4R_5$, $—C(O)R_4$, $—C(O)OR_4$, $—OR_4$, $—OC(O)R_4$, $—OC(O)OR_4$, $—OC(O)NR_4R_5$, $—NR_4R_5$, $—SR_4$, $—S(O)R_4$, $—S(O)_2R_4$, $—(CH_2)_nOH$, or a 3- to 10-membered saturated or unsaturated ring containing 0 to 3 heteroatoms, wherein the 3- to 10-membered saturated or unsaturated ring containing 0 to 3 heteroatoms is optionally substituted with 1 to 3 $R_4$;

$R_2$ is selected from hydrogen, $C_1$ to $C_6$ alkyl, $C_2$ to $C_6$ alkenyl, $C_2$ to $C_6$ alkynyl, halogenated $C_1$ to $C_6$ alkyl, halogenated $C_2$ to $C_6$ alkenyl, halogenated $C_2$ to $C_6$ alkynyl, halogen, cyano, nitro, $—C(O)NR_4R_5$, $—C(O)R_4$, $—C(O)OR_4$, $—OR_4$, $—OC(O)R_4$, $—OC(O)OR_4$, $—OC(O)NR_4R_5$, $—NR_4R_5$, $—(CH_2)_nNR_4R_5$, $—SR_4$, $—S(O)R_4$, $—S(O)_2R_4$, or $—(CH_2)_nOH$;

$R_3$ is selected from hydrogen, $C_1$ to $C_6$ alkyl, $C_2$ to $C_6$ alkenyl, $C_2$ to $C_6$ alkynyl, halogenated $C_1$ to $C_6$ alkyl, halogenated $C_2$ to $C_6$ alkenyl, halogenated $C_2$ to $C_6$ alkynyl, halogen, cyano, nitro, $—C(O)NR_4R_5$, $—C(O)R_4$, $—C(O)OR_4$, $—OR_4$, $—OC(O)R_4$, $—OC(O)OR_4$, $—OC(O)NR_4R_5$, $—NR_4R_5$, $—(CH_2)_nNR_4R_5$, $—SR_4$, $—S(O)R_4$, $—S(O)_2R_4$, or $—(CH_2)_nOH$;

each $R_4$ and each $R_5$ are independently selected from hydrogen, $C_1$ to $C_6$ alkyl, halogenated $C_1$ to $C_6$ alkyl, $C_3$ to $C_6$ cycloalkyl, halogenated $C_3$ to $C_6$ cycloalkyl, $C_3$ to $C_6$ heterocycloalkyl, halogenated $C_3$ to $C_6$ heterocycloalkyl, halogen, $=O$, $—(CH_2)_nC(O)NR_6R_7$, $—C(O)R_6$, $—C(O)OR_6$, $—OR_6$, $—OC(O)R_6$, $—OC(O)OR_6$, $—OC(O)NR_6R_7$, $—(CH_2)_nNR_6R_7$, $—SR_6$, $—S(O)R_6$, $—(CH_2)_nS(O)_2R_6$, $—(CH_2)_nOH$, or $—(CH_2)_nCN$, respectively, or $R_4$ and $R_5$ together with adjacent atoms form a 5- to 6-membered saturated or unsaturated ring containing 0 to 3 heteroatoms, wherein the 5- to 6-membered saturated or unsaturated ring containing 0 to 3 heteroatoms is optionally substituted with 1 to 3 $R_6$;

each $R_6$ and each $R_7$ are independently selected from hydrogen, halogen, carbonyl, hydroxyl, cyano, nitro, $C_1$ to $C_6$ alkyl, halogenated $C_1$ to $C_6$ alkyl, $C_3$ to $C_6$ cycloalkyl, or halogenated $C_3$ to $C_6$ cycloalkyl, respectively; and each m and each n are independently selected from 0, 1, 2, or 3, respectively.

In some embodiments, the general Formula (I) is a compound represented by general Formula (Ia):

(Ia)

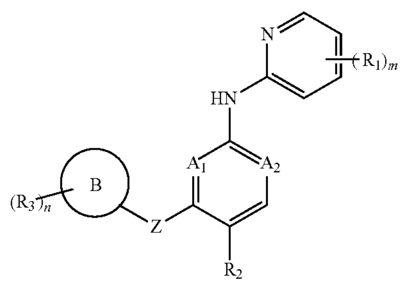

or a tautomer, a mesomer, a racemate, an enantiomer, a diastereomer, or a pharmaceutically acceptable salt thereof, wherein the ring B, $A_1$, $A_2$, Z, $R_1$, $R_2$, $R_3$, m, and n are defined as defined above.

In some other embodiments, the general Formula (I) is a compound represented by general Formula (Ib):

(Ib)

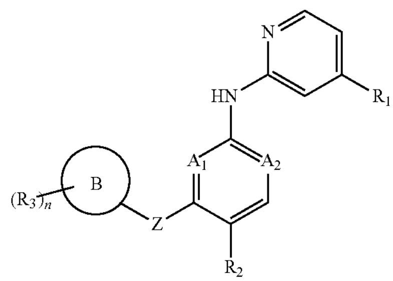

or a tautomer, a mesomer, a racemate, an enantiomer, a diastereomer, or a pharmaceutically acceptable salt thereof;

wherein the ring B, $A_1$, $A_2$, Z, $R_1$, $R_2$, $R_3$, and n are defined as defined above.

In some other embodiments, the general Formula (I) is a compound represented by general Formula (Ic):

(Ic)

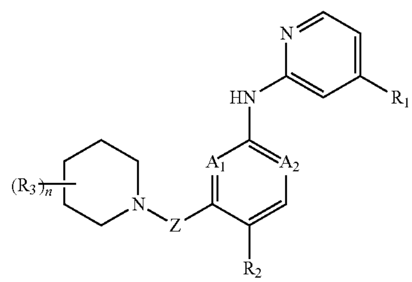

or a tautomer, a mesomer, a racemate, an enantiomer, a diastereomer, or a pharmaceutically acceptable salt thereof;

wherein $A_1$, $A_2$, Z, $R_1$, $R_2$, $R_3$, and n are defined as defined above; preferably, $A_1$ and $A_2$ are each independently selected from C or N;

Z is selected from $—C(O)—$, $—CH_2—$, or $—NH—$;

$R_1$ is selected from hydrogen, $C_1$ to $C_6$ alkyl, halogenated $C_1$ to $C_6$ alkyl, halogen, cyano, nitro, $—C(O)NR_4R_5$, $—C(O)OR_4$, $—OR_4$, or a 3- to 10-membered saturated or unsaturated ring containing 0 to 3 heteroatoms (as a non-limiting example, the 3- to 10-membered saturated or unsaturated ring containing 0 to 3 heteroatoms may be

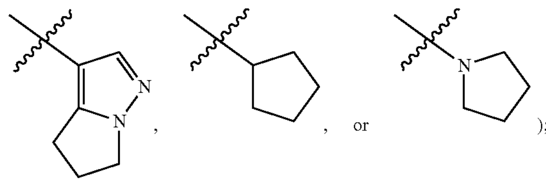 [SMILES: *c1cnn2c1CCC2 ; *C1CCCC1 ; *N1CCCC1]

);

$R_2$ is selected from hydrogen, $C_1$ to $C_6$ alkyl, halogenated $C_1$ to $C_6$ alkyl, halogen, cyano, nitro, $—C(O)NR_4R_5$, $—C(O)R_4$, $—C(O)OR_4$, or $—OR_4$;

$R_3$ is selected from hydrogen, $C_1$ to $C_6$ alkyl, halogenated $C_1$ to $C_6$ alkyl, halogen, cyano, nitro, —C(O)$NR_4R_5$, —C(O)$R_4$, —C(O)$OR_4$, —$OR_4$, —$NR_4R_5$, or —$(CH_2)_nNR_4R_5$;

each $R_4$ and each $R_5$ are independently selected from hydrogen, $C_1$ to $C_6$ alkyl, halogenated $C_1$ to $C_6$ alkyl, $C_3$ to $C_6$ cycloalkyl, halogenated $C_3$ to $C_6$ cycloalkyl, $C_3$ to $C_6$ heterocycloalkyl, halogenated $C_3$ to $C_6$ heterocycloalkyl, halogen, —C(O)$R_6$, —C(O)$OR_6$, —$OR_6$, or —$(CH_2)_nS(O)_2R_6$, respectively, or $R_4$ and $R_5$ together with adjacent atoms form a 5- to 6-membered saturated or unsaturated ring containing 0 to 3 heteroatoms, wherein the 5- to 6-membered saturated or unsaturated ring containing 0 to 3 heteroatoms is optionally substituted with 1 to 3 $R_6$ (as a non-limiting example, $R_4$ and $R_5$ together with adjacent atoms form the 5- to 6-membered saturated or unsaturated ring containing 0 to 3 heteroatoms, which may be

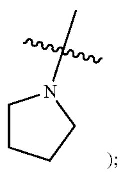 [SMILES: *N1CCCC1]

);

each $R_6$ and each $R_7$ are independently selected from hydrogen, halogen, carbonyl, hydroxyl, cyano, nitro, $C_1$ to $C_6$ alkyl, halogenated $C_1$ to $C_6$ alkyl, $C_3$ to $C_6$ cycloalkyl, or halogenated $C_3$ to $C_6$ cycloalkyl, respectively; and each n is independently selected from 0, 1, 2, or 3.

In some other embodiments, the general Formula (I) is a compound represented by general Formula (Id):

(Id)

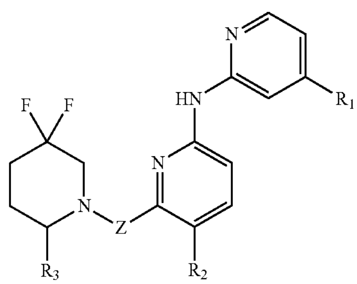

or a tautomer, a mesomer, a racemate, an enantiomer, a diastereomer, or a pharmaceutically acceptable salt thereof;

wherein Z, $R_1$, $R_2$, and $R_3$ are defined as defined above; preferably,

Z is selected from —C(O)—, —$CH_2$—, or —NH—;

$R_1$ is selected from hydrogen, $C_1$ to $C_6$ alkyl, halogenated $C_1$ to $C_6$ alkyl, halogen, cyano, nitro, —C(O)$NR_4R_5$, —C(O)$OR_4$, —$OR_4$, or a 3- to 10-membered saturated or unsaturated ring containing 0 to 3 heteroatoms (as a non-limiting example, the 3- to 10-membered saturated or unsaturated ring containing 0 to 3 heteroatoms may be

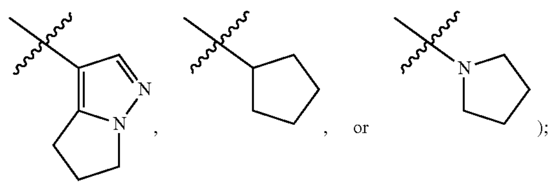 [SMILES: *c1cnn2c1CCC2 ; *C1CCCC1 ; *N1CCCC1]

);

$R_2$ is selected from hydrogen, $C_1$ to $C_6$ alkyl, halogenated $C_1$ to $C_6$ alkyl, halogen, cyano, nitro, —C(O)$NR_4R_5$, —C(O)$R_4$, —C(O)$OR_4$, or —$OR_4$;

$R_3$ is selected from hydrogen, $C_1$ to $C_6$ alkyl, halogenated $C_1$ to $C_6$ alkyl, cyano, nitro, —C(O)$NR_4R_5$, —C(O)$R_4$, —C(O)$OR_4$, —$OR_4$, —$NR_4R_5$, or —$(CH_2)_nNR_4R_5$;

each $R_4$ and each $R_5$ are independently selected from hydrogen, $C_1$ to $C_6$ alkyl, halogenated $C_1$ to $C_6$ alkyl, $C_3$ to $C_6$ cycloalkyl, halogenated $C_3$ to $C_6$ cycloalkyl, $C_3$ to $C_6$ heterocycloalkyl, halogenated $C_3$ to $C_6$ heterocycloalkyl, halogen, —C(O)$R_6$, —C(O)$OR_6$, —$OR_6$, or —$(CH_2)_nS(O)_2R_5$, respectively, or $R_4$ and $R_5$ together with adjacent atoms form a 5- to 6-membered saturated or unsaturated ring containing 0 to 3 heteroatoms, wherein the 5- to 6-membered saturated or unsaturated ring containing 0 to 3 heteroatoms is optionally substituted with 1 to 3 $R_6$ (as a non-limiting example, $R_4$ and $R_5$ together with adjacent atoms form the 5- to 6-membered saturated or unsaturated ring containing 0 to 3 heteroatoms, which may be

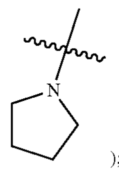

);

each $R_6$ and each $R_7$ are independently selected from hydrogen, halogen, carbonyl, hydroxyl, cyano, nitro, $C_1$ to $C_6$ alkyl, halogenated $C_1$ to $C_6$ alkyl, $C_3$ to $C_6$ cycloalkyl, or halogenated $C_3$ to $C_6$ cycloalkyl, respectively; and each n is independently selected from 0, 1, 2, or 3.

In some other embodiments, the general Formula (I) is a compound represented by general Formula (Ie):

(Ie)

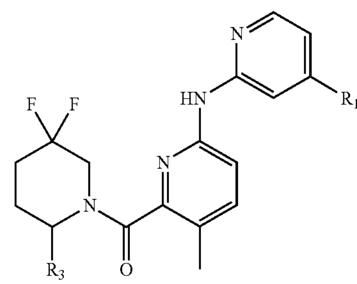

or a tautomer, a mesomer, a racemate, an enantiomer, a diastereomer, or a pharmaceutically acceptable salt thereof;

wherein $R_1$ and $R_3$ are defined as defined above.

In some other embodiments, $R_1$ is selected from cyano, nitro, halogen, trifluoromethyl, trifluoromethoxy, difluoromethyl, difluoromethoxy, monofluoromethyl, methyl, methoxy, or ethoxy.

In some other embodiments, $R_3$ is selected from halogen, $—CH_2NHC(O)CH_3$, or $—CH_2NH_2$.

In some other embodiments, the compound represented by general Formula (I) is selected from the following:

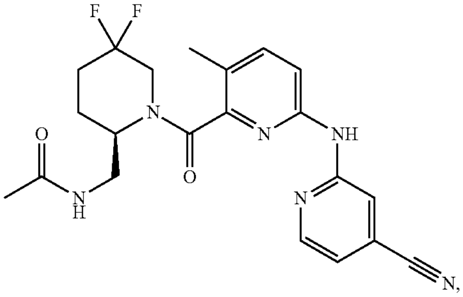
,

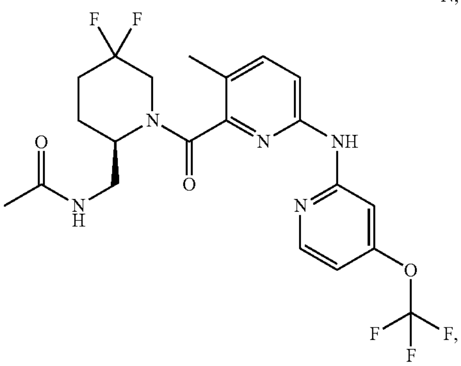
,

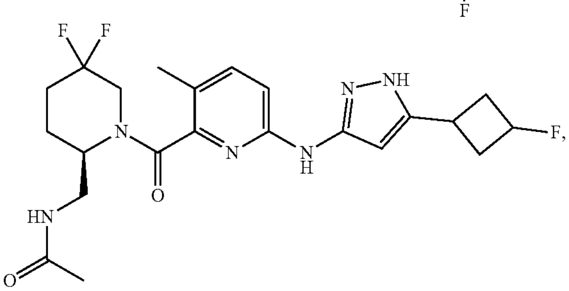
,

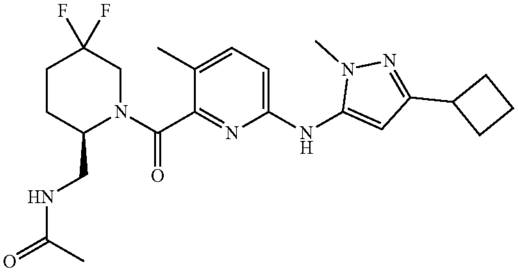
,

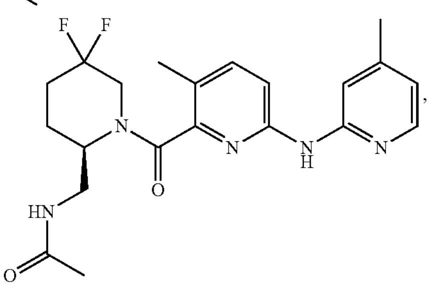
,

-continued

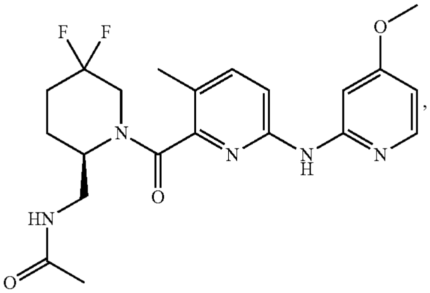
,

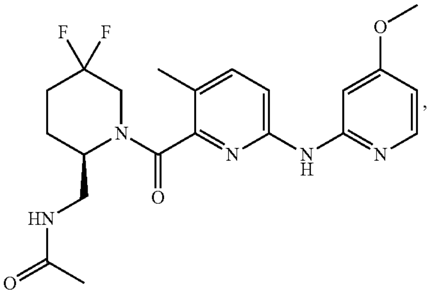
,

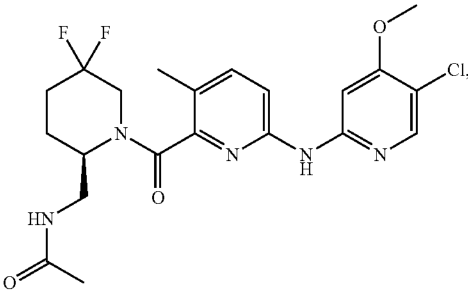
,

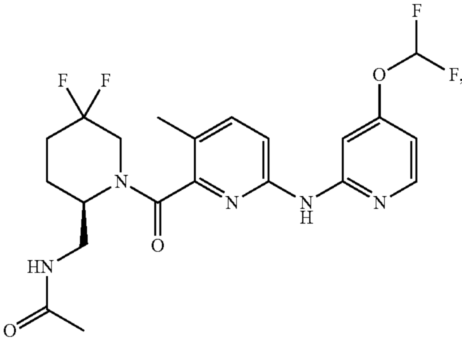
,

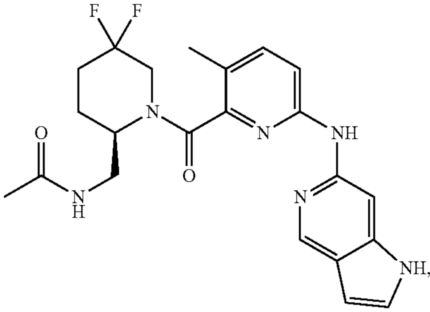
,

-continued
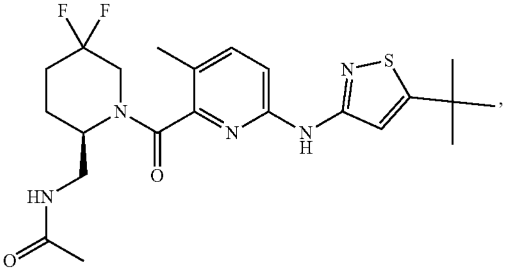
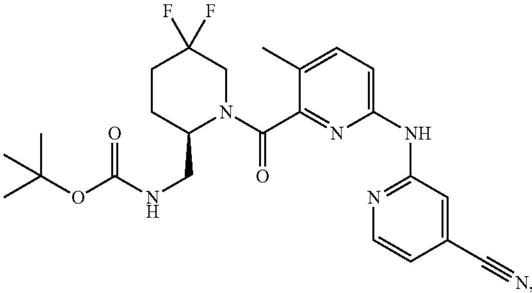
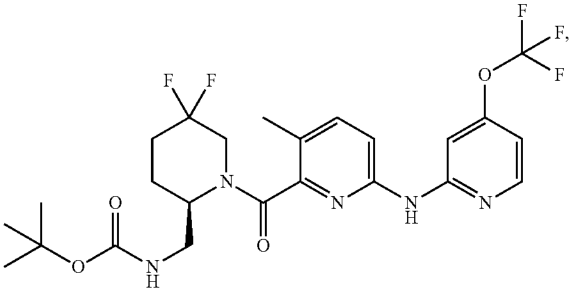
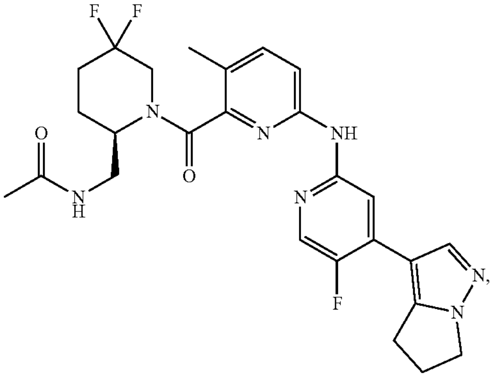
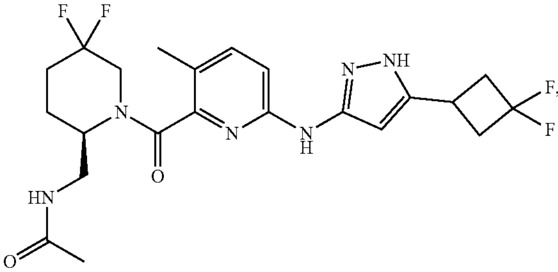
-continued
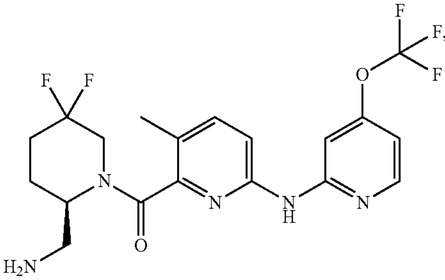
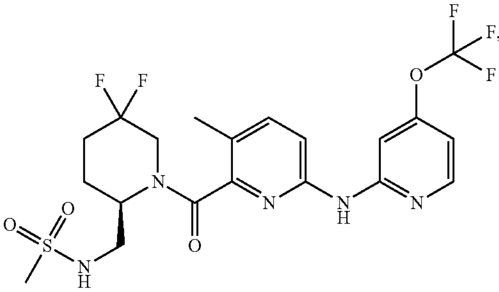
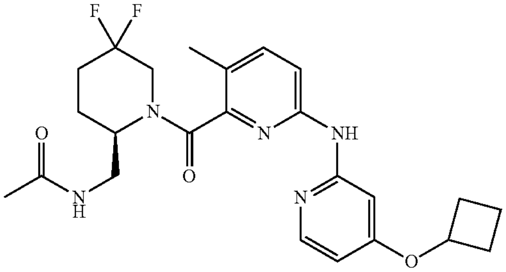
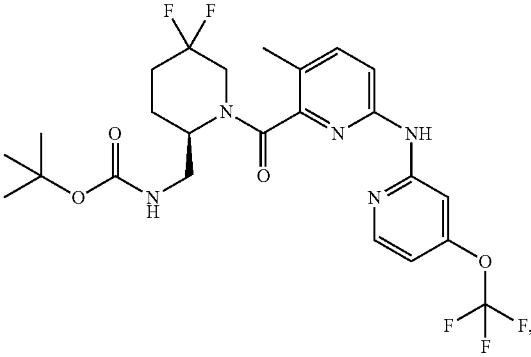
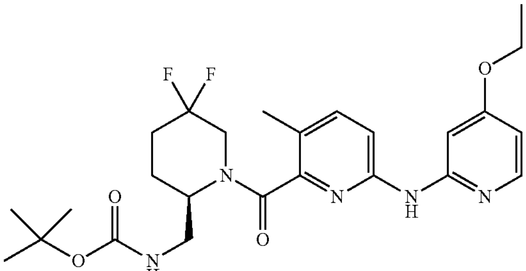

-continued
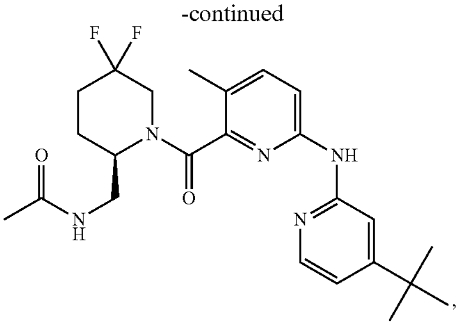
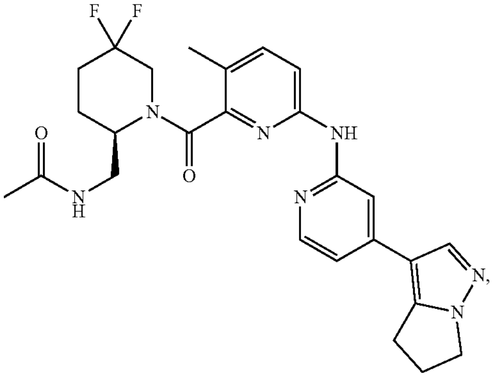
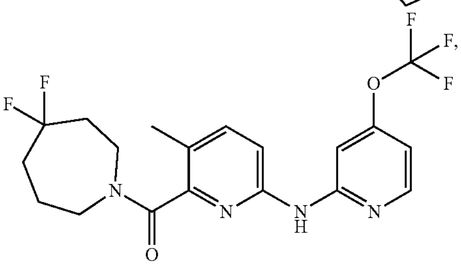
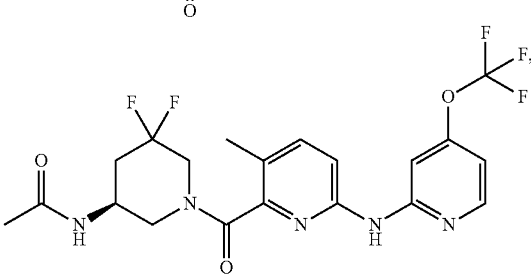
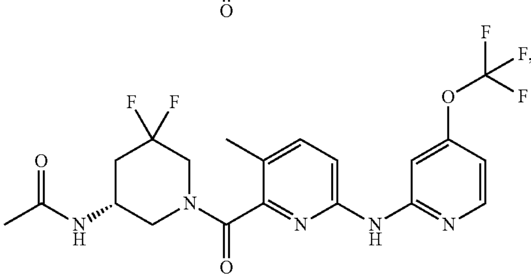
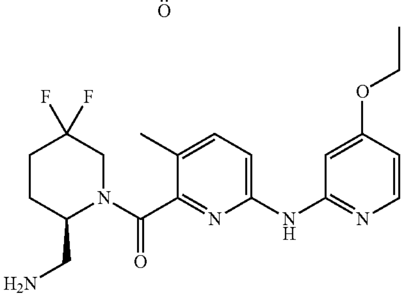
-continued
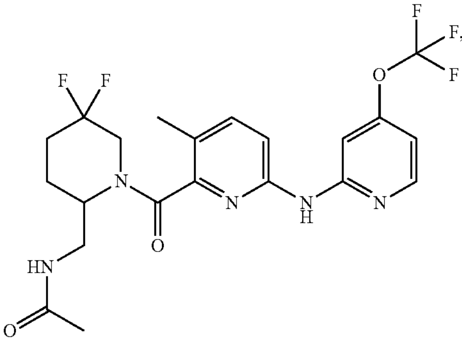
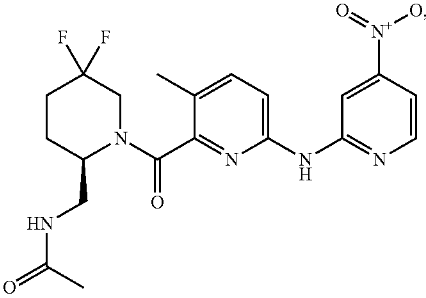
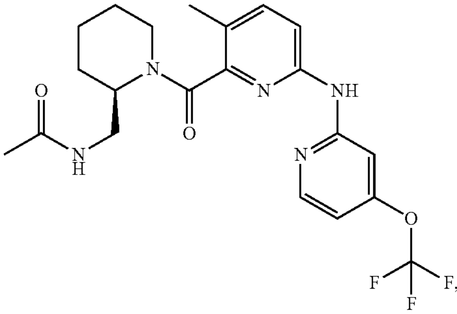
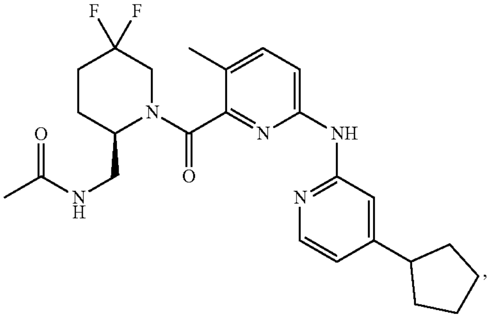
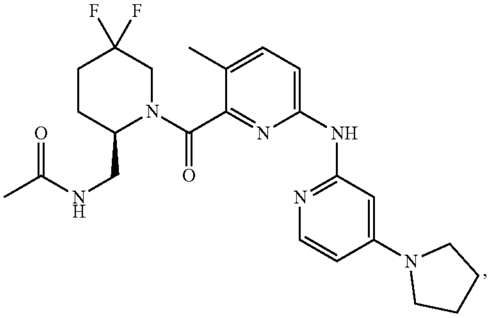

-continued
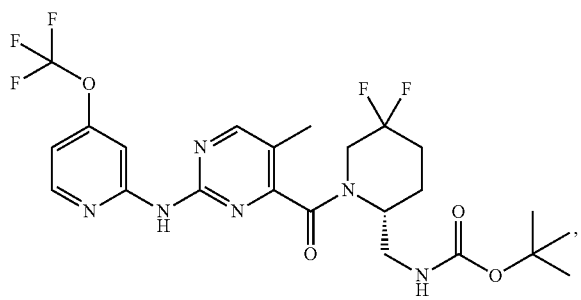
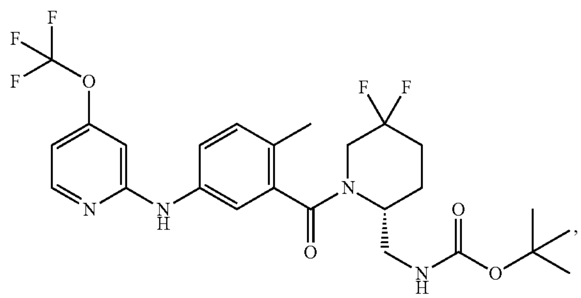
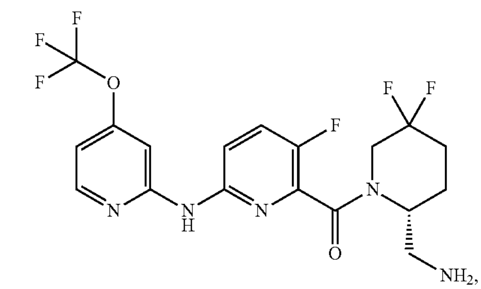
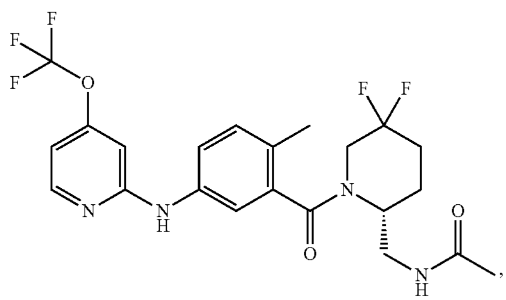
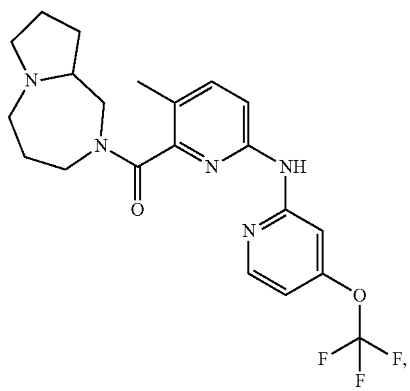
-continued
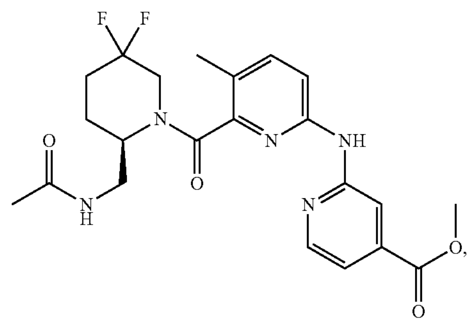
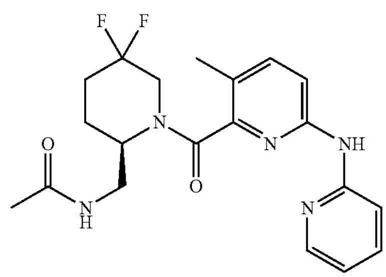
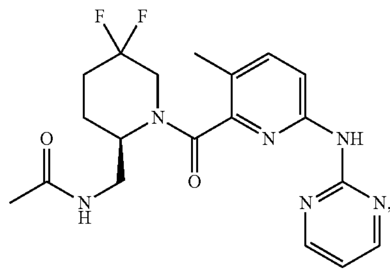
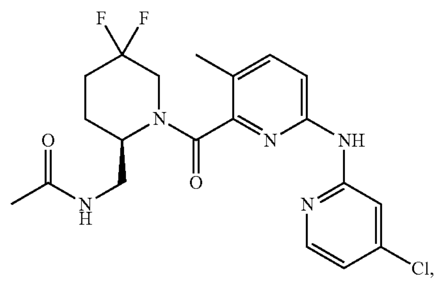
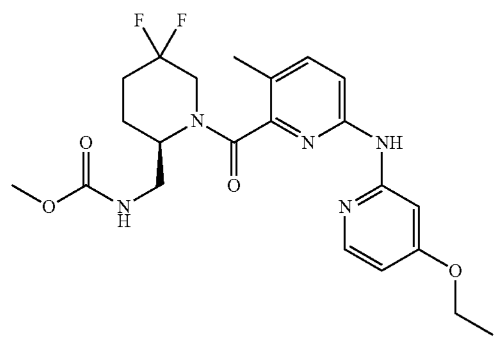

-continued
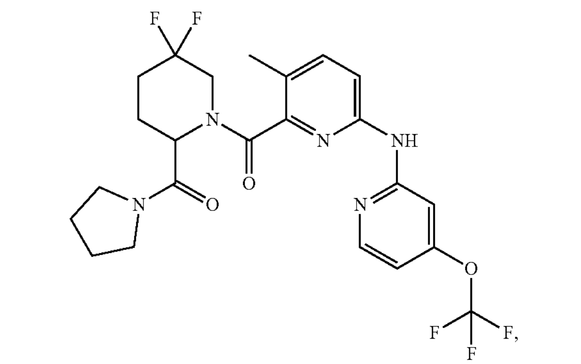
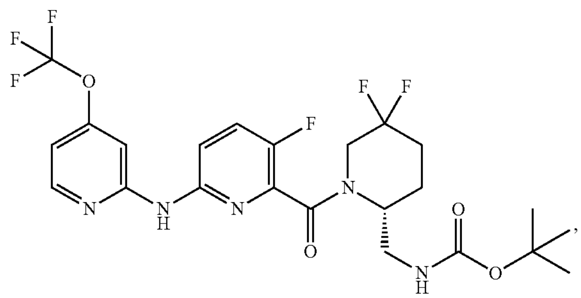
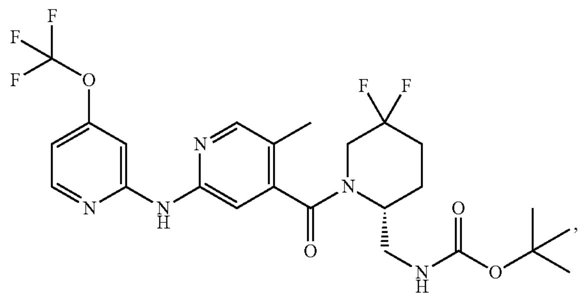
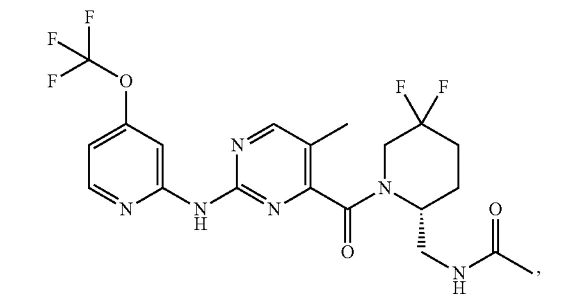
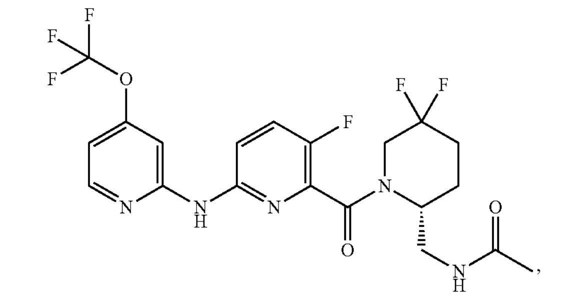
-continued
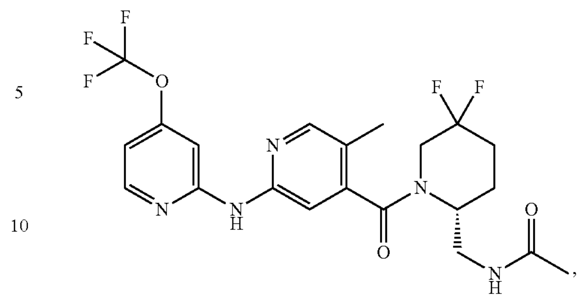
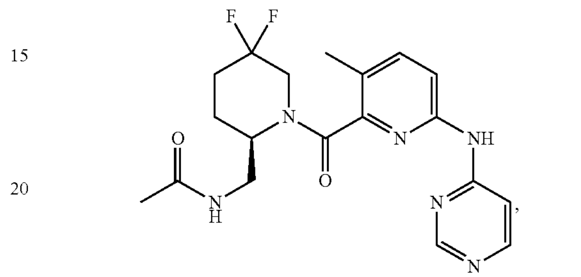
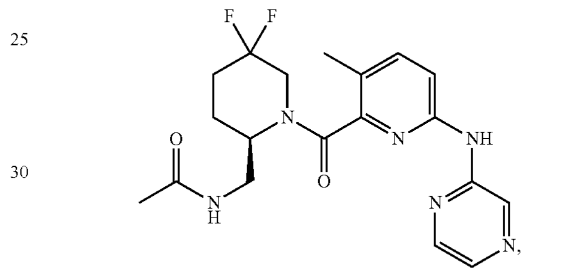
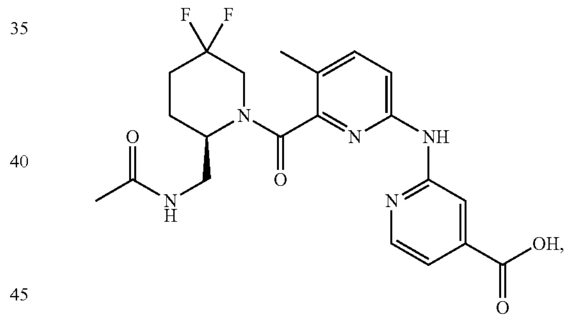
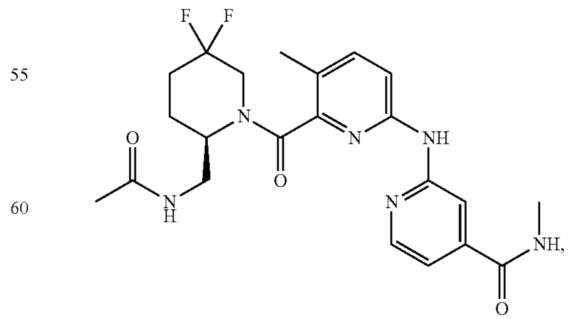

-continued
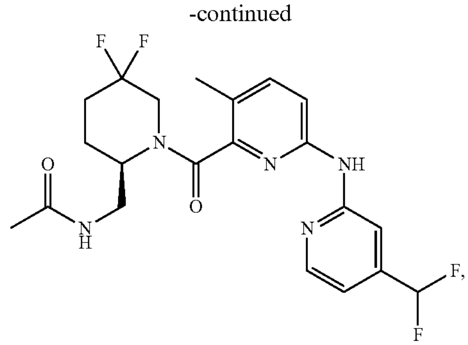
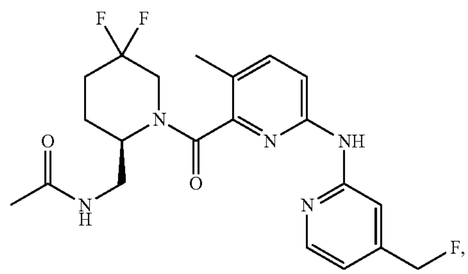
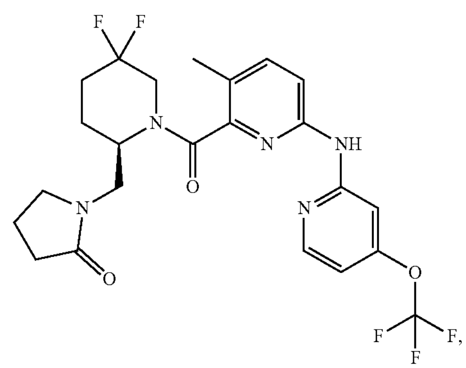
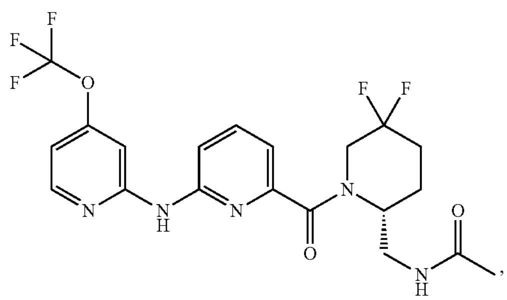
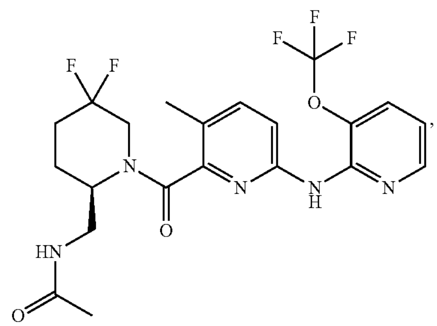
-continued
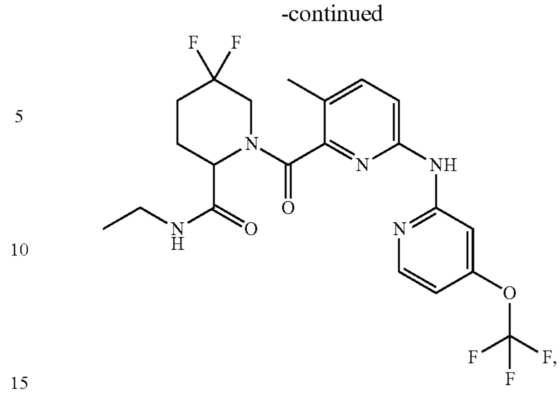
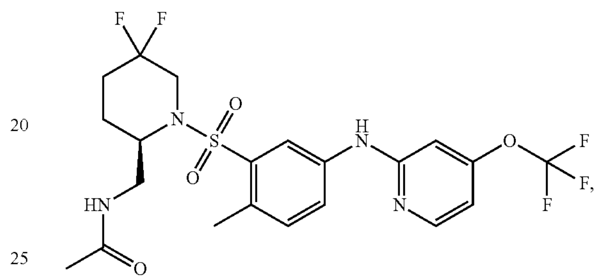
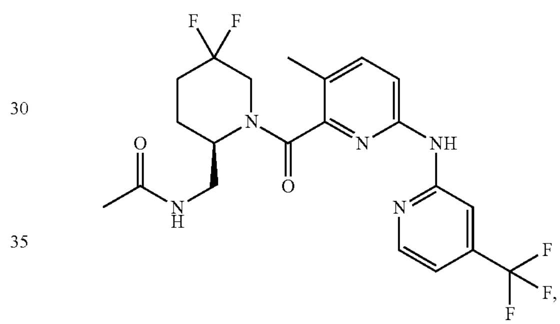
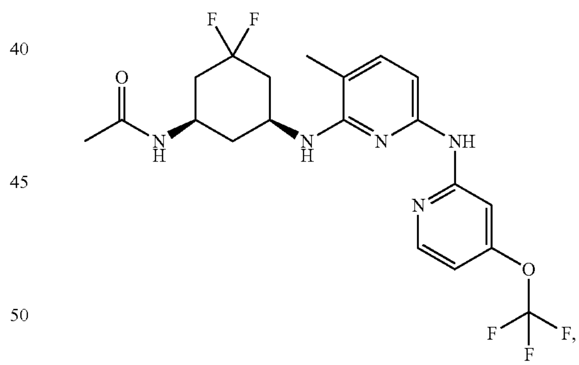
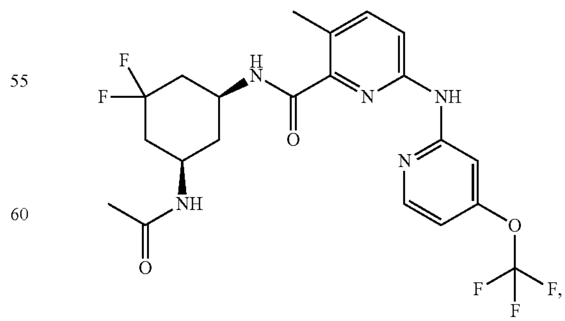

-continued

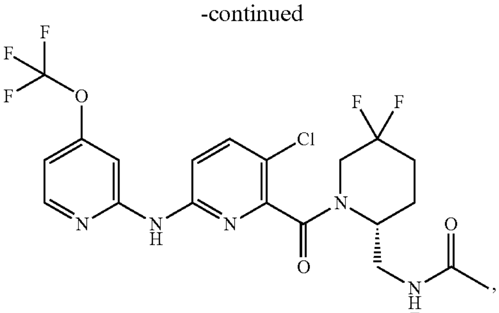

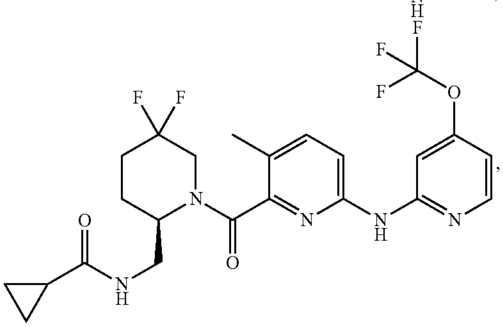

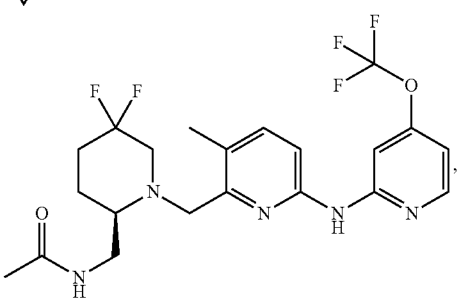

or

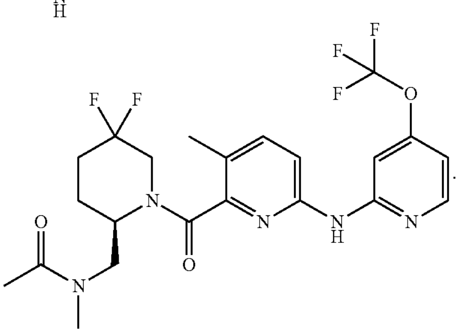

In another aspect, the present application further provides a use of the preceding compound or an isomer or a pharmaceutically acceptable salt thereof for preparing a drug for a CDK-mediated disease.

In some embodiments, the CDK-mediated disease is a CDK9-mediated disease.

In some other embodiments, the CDK-mediated disease is cancer, a cardiovascular disease, an inflammatory disease, a neurodegenerative disease, or a viral disease.

In some other embodiments, the CDK-mediated disease is cancer.

In some other embodiments, the cancer is leukemia, lymphoma, multiple myeloma, lung cancer, prostate cancer, head and neck cancer, breast cancer, pancreatic cancer, colorectal cancer, or melanoma.

In another aspect, the present application further provides a pharmaceutical composition including a therapeutically effective amount of the preceding compound or an isomer or a pharmaceutically acceptable salt thereof; and a pharmaceutically acceptable carrier or excipient.

Terms

Unless otherwise stated, the terms used in the specification and claims have the meanings below.

The term "isomer" includes an enantiomeric form, a diastereomeric form, and a geometric (or conformational) isomeric form of a given structure. For example, the present application includes R and S configurations at each asymmetric center, Z and E double-bond isomers, Z and E conformational isomers, a single stereochemical isomer, and a mixture of an enantiomer, a diastereomer, and a geometric (or conformational) isomer.

The term "pharmaceutically acceptable salt" refers to, for example, an acid addition salt and/or an alkali salt thereof. Suitable acid addition salts are formed by acids, which form non-toxic salts such as hydrochlorides/chlorides. Suitable alkali salts are formed by bases, which form non-toxic salts such as calcium and sodium salts. Hemi-salts of acids and bases may also be formed, such as hemisulfates and hemicalcium salts.

The term "therapeutically effective amount" refers to the following amount of the compound of the present application: (i) an amount for the treatment of a specific disease, condition, or disorder; (ii) an amount for the alleviation, relief, or elimination of one or more symptoms of a specific disease, condition, or disorder; or (iii) an amount for the prevention or delay of the onset of one or more symptoms of a specific disease, condition, or disorder in the present application.

The term "pharmaceutically acceptable carrier or excipient" refers to a non-toxic carrier, adjuvant, or vehicle that does not impair the pharmacological activity of the compound formulated with it.

The term "alkyl" refers to a saturated aliphatic hydrocarbyl group, which is a straight or branched chain group containing from 1 to 20 carbon atoms, preferably alkyl containing 1 to 12 carbon atoms, more preferably alkyl containing 1 to 6 carbon atoms. Non-limiting examples of lower alkyl containing 1 to 6 carbon atoms include methyl, ethyl, n-propyl, isopropyl, n-butyl, isobutyl, t-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, etc.

The term "alkoxy" refers to —O-alkyl and —O-unsubstituted cycloalkyl, wherein alkyl is defined as defined above. Non-limiting examples of alkoxy include methoxy, ethoxy, propoxy, butoxy, cyclopropoxy, cyclobutoxy, cyclopentoxy, and cyclohexoxy.

The term "cycloalkyl" refers to a saturated or partially unsaturated monocyclic or polycyclic hydrocarbon substituent. The cycloalkyl ring includes 3 to 20 carbon atoms, preferably 3 to 12 carbon atoms, more preferably 3 to 6 carbon atoms (e.g. 3, 4, 5, or 6 carbon atoms), and most preferably 5 to 6 carbon atoms. Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl, etc. Polycyclic cycloalkyl includes spiro, fused, and bridged cycloalkyl groups.

The term "spirocycloalkyl" refers to a 5- to 20-membered polycyclic group with individual rings sharing one carbon atom (called a spiro atom), wherein the rings may contain one or more double bonds, but no ring has a completely conjugated π-electron system. The spirocycloalkyl is preferably 6- to 14-membered and more preferably 7- to 10-membered (e.g., 7-, 8-, 9-, or 10-membered). According to the number of spiro atoms shared between rings, spirocycloalkyl is divided into mono-spiro cycloalkyl, di-spiro cycloalkyl, or poly-spiro cycloalkyl, preferably mono-spiro cycloalkyl and di-spiro cycloalkyl. More preferably, the spirocycloalkyl is 4-membered/4-membered, 4-membered/5-membered, 4-membered/6-membered, 5-membered/5-membered, or 5-membered/6-membered mono-spiro cycloalkyl.

The term "fused cycloalkyl" refers to a 5- to 20-membered all-carbon polycyclic group in which each ring in the system shares an adjacent pair of carbon atoms with another ring in the system, wherein one or more rings may contain one or more double bonds, but no ring has a completely conjugated π-electron system. The fused cycloalkyl is preferably 6- to 14-membered and more preferably 7- to 10-membered. According to the number of rings, the fused cycloalkyl may be divided into bicyclic, tricyclic, tetracyclic, or polycyclic fused cycloalkyl, preferably bicyclic or tricyclic fused cycloalkyl, more preferably 5-membered/5-membered or 5-membered/6-membered bicyclic fused cycloalkyl.

The term "bridged cycloalkyl" refers to a 5- to 20-membered all-carbon polycyclic group in which any two rings share two carbon atoms that are not directly connected, wherein the rings may contain one or more double bonds, but no ring has a completely conjugated 71-electron system. The bridged cycloalkyl is preferably 6- to 14-membered and more preferably 7- to 10-membered. According to the number of rings, the bridged cycloalkyl may be divided into bicyclic, tricyclic, tetracyclic, or polycyclic bridged cycloalkyl, preferably bicyclic, tricyclic, or tetracyclic bridged cycloalkyl, more preferably bicyclic or tricyclic bridged cycloalkyl.

The term "heterocycloalkyl" refers to a saturated or partially unsaturated monocyclic or polycyclic hydrocarbon substituent containing 3 to 20 ring atoms, wherein one or more ring atoms are heteroatoms selected from nitrogen, oxygen, or $S(O)_m$ (wherein m is an integer from 0 to 2) but exclude —O—O—, —O—S—, or —S—S— in the ring, with the remaining ring atoms being carbon. Preferably, the heterocycloalkyl contains 3 to 12 ring atoms, wherein 1 to 4 ring atoms are heteroatoms; more preferably, the heterocycloalkyl contains 3 to 8 ring atoms, wherein 1 to 3 ring atoms are heteroatoms; most preferably, the heterocycloalkyl contains 5 to 6 ring atoms, wherein 1 to 2 or 1 to 3 ring atoms are heteroatoms. Non-limiting examples of monocyclic heterocyclyl include pyrrolidinyl, imidazolidinyl, tetrahydrofuranyl, tetrahydropyranyl, tetrahydrothienyl, dihydroimidazolyl, dihydrofuranyl, dihydropyrazolyl, dihydropyrrolyl, piperidinyl, piperazinyl, morpholinyl, thiomorpholinyl, homopiperazinyl, etc., preferably tetrahydropyranyl, piperidinyl, and pyrrolidinyl. Polycyclic heterocycloalkyl includes spiroheterocyclyl, fused heterocyclyl, and bridged heterocyclyl.

The term "spiroheterocyclyl" refers to a 5- to 20-membered polycyclic heterocyclyl group with individual rings sharing one atom (called a spiro atom), wherein one or more ring atoms are heteroatoms selected from nitrogen, oxygen, or $S(O)_m$ (wherein m is an integer from 0 to 2), with the remaining ring atoms being carbon. The rings may contain one or more double bonds, but no ring has a completely conjugated π-electron system. The spiroheterocyclyl is preferably 6- to 14-membered and more preferably 7- to 10-membered. According to the number of spiro atoms shared between rings, spiroheterocyclyl is divided into mono-spiro heterocyclyl, di-spiro heterocyclyl, or poly-spiro heterocyclyl, preferably mono-spiro heterocyclyl and di-spiro heterocyclyl. More preferably, the spiroheterocyclyl is 4-membered/4-membered, 4-membered/5-membered, 4-membered/6-membered, 5-membered/5-membered, or 5-membered/6-membered mono-spiro heterocyclyl.

The term "fused heterocyclyl" refers to a 5- to 20-membered polycyclic heterocyclyl group in which each ring in the system shares an adjacent pair of carbon atoms with another ring in the system, wherein one or more rings may contain one or more double bonds, but no ring has a completely conjugated π-electron system; and one or more ring atoms are heteroatoms selected from nitrogen, oxygen, or $S(O)_m$ (wherein m is an integer from 0 to 2), with the remaining ring atoms being carbon. The fused heterocyclyl is preferably 6- to 14-membered and more preferably 7- to 10-membered. According to the number of rings, the fused heterocyclyl may be divided into bicyclic, tricyclic, tetracyclic, or polycyclic fused heterocyclyl, preferably bicyclic or tricyclic fused heterocyclyl, more preferably 5-membered/5-membered or 5-membered/6-membered bicyclic fused heterocyclyl.

The term "bridged heterocyclyl" refers to a 5- to 14-membered polycyclic heterocyclyl group in which any two rings share two atoms that are not directly connected, wherein the rings may contain one or more double bonds, but no ring has a completely conjugated 71-electron system; and one or more ring atoms are heteroatoms selected from nitrogen, oxygen, or $S(O)_m$ (wherein m is an integer from 0 to 2), with the remaining ring atoms being carbon. The bridged heterocyclyl is preferably 6- to 14-membered and more preferably 7- to 10-membered. According to the number of rings, the bridged heterocyclyl may be divided into bicyclic, tricyclic, tetracyclic, or polycyclic bridged heterocyclyl, preferably bicyclic, tricyclic, or tetracyclic bridged heterocyclyl, more preferably bicyclic or tricyclic bridged heterocyclyl.

The term "aryl" refers to a 6- to 14-membered all-carbon monocyclic ring or polycyclic fused ring (i.e., rings sharing an adjacent pair of carbon atoms) group having a conjugated 71-electron system and is preferably 6- to 10-membered, such as phenyl and naphthyl.

The term "heteroaryl" refers to a heteroaromatic system containing 1 to 4 heteroatoms and 5 to 14 ring atoms, wherein the heteroatoms are selected from oxygen, sulfur, and nitrogen. The heteroaryl is preferably 5- to 10-membered heteroaryl containing 1 to 3 heteroatoms and more preferably 5- or 6-membered heteroaryl containing 1 to 2 heteroatoms. Preferred examples are imidazolyl, furyl, thienyl, thiazolyl, pyrazolyl, oxazolyl, pyrrolyl, tetrazolyl, pyridyl, pyrimidinyl, thiadiazolyl, pyrazinyl, pyridazinyl, etc.

The term "hydroxyalkyl" refers to alkyl substituted with hydroxyl, wherein alkyl is defined as defined above.

The term "haloalkyl" refers to alkyl substituted with one or more halogens, wherein alkyl is defined as defined above.

The term "haloalkoxy" refers to alkoxy substituted with one or more halogens, wherein alkoxy is defined as defined above.

The term "deuterated alkyl" refers to alkyl substituted with one or more deuterium atoms, wherein alkyl is defined as defined above.

The term "deuterated alkoxy" refers to alkoxy substituted with one or more deuterium atoms, wherein alkoxy is defined as defined above.

The term "cycloalkyl alkyl" refers to alkyl substituted with one or more cycloalkyl groups, wherein cycloalkyl and alkyl are defined as defined above.

The term "cycloalkyl-oxy" refers to —O-cycloalkyl, wherein cycloalkyl is defined as defined above.

The term "heterocyclyl alkyl" refers to alkyl substituted with one or more heterocyclyl groups, wherein heterocyclyl and alkyl are defined as defined above.

The term "arylalkyl" refers to alkyl substituted with one or more aryl groups, wherein aryl and alkyl are defined as defined above.

The term "hydroxyl" refers to an —OH group.

The term "halogen" refers to fluorine, chlorine, bromine, or iodine.

The term "amino" refers to —$NH_2$.

The term "cyano" refers to —CN.

The term "nitro" refers to —$NO_2$.

The term "carboxyl" refers to —C(O)OH.

DETAILED DESCRIPTION

Example 1: (R)—N-((1-(6-((4-cyanopyridin-2-yl)amino)-3-methylpyridine-2-carbonyl)-5,5-difluoropiperidin-2-yl)methyl)acetamide (1)

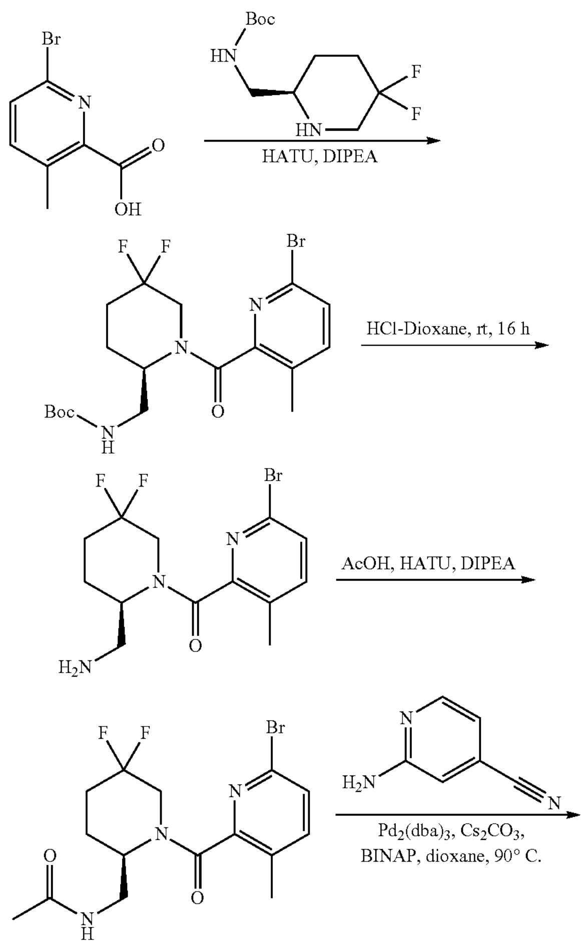

-continued

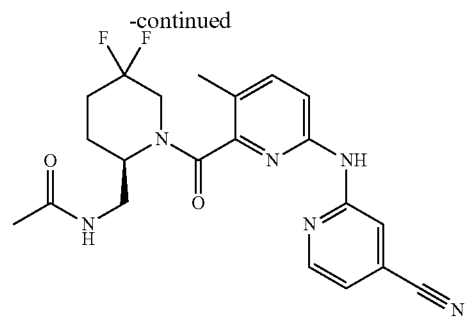

Step 1: (R)-((1-(6-bromo-3-methylpyridine-2-carbonyl)-5,5-difluoropiperidin-2-yl)methyl) t-butyl carbamate (2)

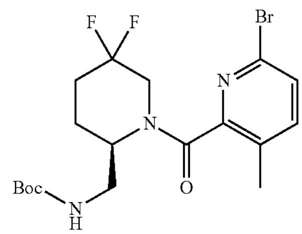 [SMILES: Cc1ccc(Br)nc1C(=O)N1CC(F)(F)CC[C@@H]1CNC(=O)OC(C)(C)C]

With stirring, 6-bromo-3-methylpicolinic acid (2.16 g, 10.00 mmol, 1 eq.) was dissolved in DCM (50 mL), and DIPEA (6.46 g, 49.99 mmol, 5 eq.) and HATU (5.70 g, 15.00 mmol, 1.5 eq.) were added at a temperature of an ice water bath. The reaction mixture was stirred at 0° C. for half an hour, and then (R)-((5,5-difluoropiperidin-2-yl)methyl)t-butyl carbamate (2.75 g, 11.00 mmol, 1.1 eq.) was added. The reaction mixture was stirred overnight at ambient temperature. The reaction mixture was treated with water and EtOAc, and the organic phase was isolated. The organic phase was washed with water, dried over $MgSO_4$, and concentrated to dryness. The crude product was purified through column chromatography (Biotage Rening Flash 80 g, EtOAc/n-Hep=20%-50%) to obtain a transparent wax (3.9 g, 87.01%). LC-MS (m/z): 448.1 $[M+H]^+$.

VT $^1$H NMR was performed to confirm the presence of conformational isomerism:

Room temperature: $^1$H NMR (400 MHz, DMSO-$d_6$) δ 7.72 (d, J=8.2 Hz, 1H), 7.63 (dd, J=8.2, 4.2 Hz, 1H), 7.05 (t, J=6.2 Hz, 0.25H), 6.85 (t, J=6.1 Hz, 0.65H), 4.81 (s, 0.3H), 4.66 (t, J=13.4 Hz, 0.7H), 3.77-3.37 (m, 2H), 3.31-3.19 (m, 1H), 2.98 (d, J=14.2 Hz, 1H), 2.23 (s, 2H), 2.17 (s, 1H), 2.11 (d, J=10.5 Hz, 1H), 1.92-1.63 (m, 2H), 1.40 (s, 3H), 1.33 (s, 6H). 1.230 (s, 1H);

50° C.: $^1$H NMR (400 MHz, DMSO-$d_6$) δ 7.71 (dd, J=8.3, 1.9 Hz, 1H), 7.61 (dd, J=8.1, 4.4 Hz, 1H), 6.91 (s, 0.3H), 6.71 (s, 0.7H), 4.83 (s, 0.3H), 4.69 (t, J=13.5 Hz, 0.7H), 3.76-3.24 (m, 3H), 3.03 (d, J=14.1 Hz, 1H), 2.24 (s, 2.5H), 2.21 (s, 0.5H), 2.16-1.97 (m, 1H), 1.94-1.64 (m, 2H), 1.42 (s, 3H), 1.34 (s, 7H).

Step 2: (R)-(2-(aminomethyl)-5,5-difluoropiperidin-1-yl)(6-bromo-3-methylpyridin-2-yl) methanone (3)

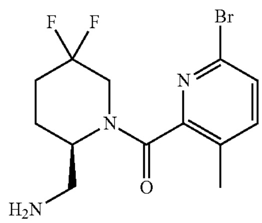 [SMILES: Cc1ccc(Br)nc1C(=O)N1CC(F)(F)CC[C@@H]1CN]

With stirring, (R)-((1-(6-bromo-3-methylpyridine-2-carbonyl)-5,5-difluoropiperidin-2-yl)methyl) t-butyl carbamate (2.24 g, 5.0 mmol, 1.0 eq.) was dissolved in EtOAc (300 mL), and a solution of HCl in 1,4-dioxane (4 M, 20 mL, 80.00 mmol, 16 eq.) was added at a temperature of an ice water bath. The reaction mixture was stirred overnight at ambient temperature. The crude product was used directly in the next step without further purification. LC-MS (m/z): 348.0 $[M+H]^+$.

Step 3: (R)—N-((1-(6-bromo-3-methylpyridine-2-carbonyl)-5,5-difluoropiperidin-2-yl)methyl) acetamide (4)

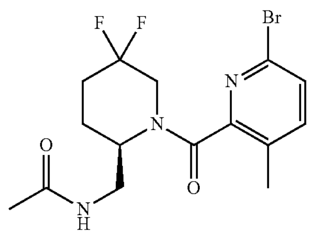 [SMILES: CC(=O)NC[C@H]1CCC(F)(F)CN1C(=O)c1nc(Br)ccc1C]

With stirring, (R)-(2-(aminomethyl)-5,5-difluoropiperidin-1-yl)(6-bromo-3-methylpyridin-2-yl) methanone (1.75 g, 5.0 mmol, 1.0 eq.) was dissolved in DCM (20 mL), and DIPEA (3.22 g, 25 mmol, 5 eq.) and HATU (2.85 g, 7.5 mmol, 1.5 eq.) were added at a temperature of an ice water bath. The reaction mixture was stirred at 0° C. for half an hour, and then acetic acid (0.6 g, 10.0 mmol, 2.0 eq.) was added. The reaction mixture was stirred overnight at ambient temperature. The reaction mixture was treated with water and EtOAc, and the organic phase was isolated. The organic phase was washed with water, dried over $MgSO_4$, and concentrated to dryness. The crude product was purified through column chromatography (Biotage Rening Flash 80 g, EtOAc/n-Hep=20%-50%) to obtain a transparent wax (1.58 g, 81.32%). LC-MS (m/z): 390.1 $[M+H]^+$.

Step 4: (R)—N-((1-(6-((4-cyanopyridin-2-yl)amino)-3-methylpyridine-2-carbonyl)-5,5-difluoropiperidin-2-yl)methyl)acetamide (1)

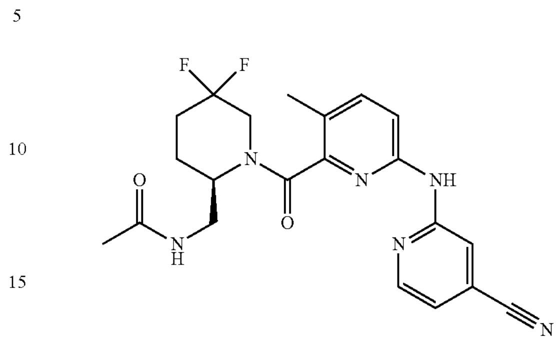

A mixture of (R)—N-((1-(6-bromo-3-methylpyridine-2-carbonyl)-5,5-difluoropiperidin-2-yl)methyl)acetamide (50.00 mg, 0.13 mmol, 1.0 eq.), 2-aminoisonicotinonitrile (53.30 mg, 0.26 mmol, 2.0 eq.), $Pd_2(dba)_3$ (11.90 mg, 0.01 mmol, 0.1 eq.), BINAP (16.17 mg, 0.26 mmol, 0.2 eq.), and $CS_2CO_3$ (127.14 mg, 0.39 mmol, 3.0 eq.) was suspended in 1,4-dioxane (3.0 mL). The resulting mixture was heated to 90° C. to react for 10 h under a nitrogen atmosphere. The reaction solution was purified through column chromatography (Biotage Rening Flash 10 g, EtOAc/n-Hep=100%, methanol/EtOAc=10%) to obtain the title compound. $^1H$ NMR (400 MHz, DMSO-$d_6$) δ 10.26 (s, 0.3H), 10.21 (s, 0.7H), 8.51-8.42 (m, 1H), 8.24 (s, 0.7H), 8.19 (s, 0.3H), 8.15 (t, J=6.3 Hz, 0.3H), 7.95 (t, J=6.1 Hz, 0.7H), 7.66 (dd, J=8.6, 2.3 Hz, 1H), 7.55 (d, J=8.5 Hz, 0.3H), 7.46 (d, J=8.5 Hz, 0.7H), 7.26 (td, J=5.0, 1.4 Hz, 1H), 4.83 (s, 0.3H), 4.73 (t, J=13.2 Hz, 0.7H), 3.74-3.63 (m, 1H), 3.52-3.36 (m, 2H), 3.31-3.21 (m, 1H), 2.33-2.00 (m, 5H), 1.95-1.71 (m, 5H). LC-MS (m/z): 429.2 $[M+H]^+$.

Example 2: (R)—N-((5,5-difluoro-1-(3-methyl-6-((4-(trifluoromethoxy)pyridin-2-yl)amino)pyridine-2-carbonyl)piperidin-2-yl)methyl)acetamide (5)

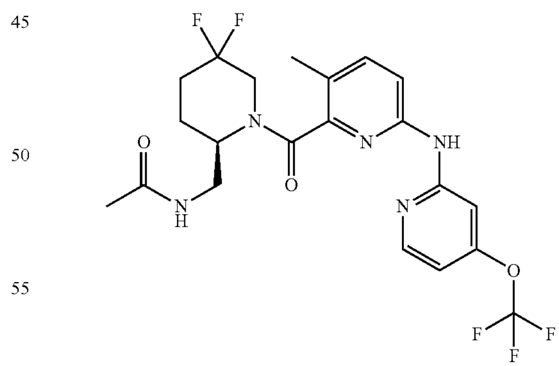

(R)—N-((5,5-difluoro-1-(3-methyl-6-((4-(trifluoromethoxy)pyridin-2-yl)amino)pyridine-2-carbonyl)piperidin-2-yl)methyl)acetamide was obtained by a method similar to the synthesis method of Compound 1 in Example 1. $^1H$ NMR (400 MHz, DMSO-$d_6$) δ 9.94 (s, 0.3H), 9.85 (s, 0.7H), 8.24 (dd, J=5.7, 2.3 Hz, 1H), 8.15 (t, J=6.2 Hz, 0.3H), 7.97 (t, J=6.1 Hz, 0.7H), 7.75-7.44 (m, 2H), 7.34 (d, J=4.9 Hz, 0.7H), 7.16 (d, J=4.9 Hz, 0.3H), 6.75 (t, J=5.5, Hz, 1H), 4.82

(s, 0.3H), 4.74 (s, 0.7H), 3.81-3.39 (m, 2H), 3.31-3.23 (m, 2H), 2.33-2.07 (m, 5H), 1.98-1.78 (m, 5H). LC-MS (m/z): 488.2 $[M+H]^+$.

Example 3: (R)—N-((5,5-difluoro-1-(6-((5-(3-fluorocyclobutyl)-1H-pyrazol-3-yl)amino)-3-methylpyridine-2-carbonyl)piperidin-2-yl))methyl)acetamide (6)

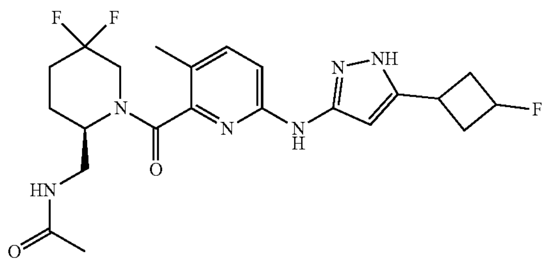 [SMILES: CC(=O)NC[C@H]1CCC(F)(F)CN1C(=O)c1nc(Nc2cc(C3CC(F)C3)[nH]n2)ccc1C]

(R)—N-((5,5-difluoro-1-(6-((5-(3-fluorocyclobutyl)-1H-pyrazol-3-yl)amino)-3-methylpyridine-2-carbonyl)piperidin-2-yl))methyl)acetamide was obtained by a method similar to the synthesis method of Compound 1 in Example 1. LC-MS (m/z): 465.2 $[M+H]^+$.

Example 4: (R)—N-((1-(6-((3-cyclobutyl-1-methyl-1H-pyrazol-5-yl)amino)-3-methylpyridine-2-carbonyl)-5,5-difluoropiperidin-2-yl)methyl)acetamide (7)

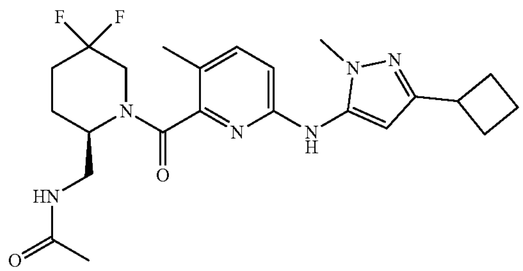 [SMILES: CC(=O)NC[C@H]1CCC(F)(F)CN1C(=O)c1nc(Nc2cc(C3CCC3)nn2C)ccc1C]

(R)—N-((1-(6-((3-cyclobutyl-1-methyl-1H-pyrazol-5-yl)amino)-3-methylpyridine-2-carbonyl)-5,5-difluoropiperidin-2-yl)methyl)acetamide was obtained by a method similar to the synthesis method of Compound 1 in Example 1. LC-MS (m/z): 461.2 $[M+H]^+$.

Example 5: (R)—N-((5,5-difluoro-1-(3-methyl-6-((4-methylpyridin-2-yl)amino)pyridine-2-carbonyl)piperidin-2-yl)methyl)acetamide (8)

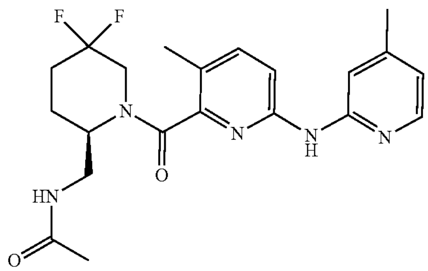 [SMILES: CC(=O)NC[C@H]1CCC(F)(F)CN1C(=O)c1nc(Nc2cc(C)ccn2)ccc1C]

(R)—N-((5,5-difluoro-1-(3-methyl-6-((4-methylpyridin-2-yl)amino)pyridine-2-carbonyl) piperidin-2-yl)methyl)acetamide was obtained by a method similar to the synthesis method of Compound 1 in Example 1. $^1$H NMR (400 MHz, DMSO-$d_6$) δ 8.30 (s, 1H), 8.10 (d, J=5.4 Hz, 1H), 7.96 (t, J=6.2 Hz, 1H), 7.68 (s, 1H), 7.62 (d, J=8.5 Hz, 1H), 7.53-7.36 (m, 1H), 6.85-6.70 (m, 1H), 4.84 (s, 0.4H), 4.73 (t, J=13.3 Hz, 0.6H), 3.62 (s, 1H), 3.53-3.38 (m, 3H), 2.43-2.02 (m, 8H), 1.99-1.59 (m, 5H). LC-MS (m/z): 418.2 $[M+H]^+$.

Example 6: (R)—N-((5,5-difluoro-1-(6-((4-methoxypyridin-2-yl)amino)-3-methylpyridine-2-carbonyl)piperidin-2-yl)methyl)acetamide (9)

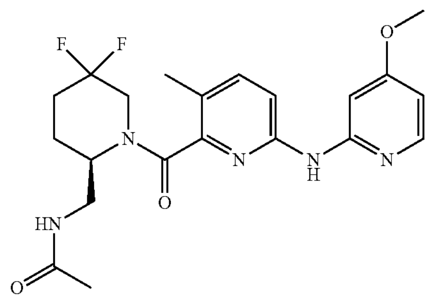 [SMILES: COc1ccnc(Nc2ccc(C)c(C(=O)N3CC(F)(F)CC[C@@H]3CNC(C)=O)n2)c1]

(R)—N-((5,5-difluoro-1-(6-((4-methoxypyridin-2-yl)amino)-3-methylpyridine-2-carbonyl) piperidin-2-yl)methyl)acetamide was obtained by a method similar to the synthesis method of Compound 1 in Example 1. $^1$H NMR (400 MHz, DMSO-$d_6$) δ 9.68 (s, 0.3H), 9.57 (s, 0.7H), 8.12 (t, J=6.1 Hz, 0.3H), 8.03 (dd, J=5.8, 1.3 Hz, 1H), 7.91 (t, J=6.1 Hz, 0.7H), 7.77-7.52 (m, 2H), 7.35 (d, J=2.3 Hz, 0.3H), 7.32 (d, J=2.3 Hz, 0.7H), 6.50 (dd, J=5.8, 2.4, Hz, 0.5H), 6.11 (dd, J=5.8, 2.3 Hz, 0.5H), 4.87-4.64 (m, 1H), 3.77 (s, 2H), 3.70 (s, 1H), 3.63 (d, J 14.9 Hz, 1H), 3.54-3.40 (m, 2H), 3.29-3.23 (m, 1H), 2.30-2.00 (m, 5H), 1.92-1.58 (m, 5H). LC-MS (m/z): 434.2 $[M+H]^+$.

Example 7: (R)—N-((1-(6-((5-chloro-4-methoxypyridin-2-yl)amino)-3-methylpyridine-2-carbonyl)-5,5-difluoropiperidin-2-yl)methyl)acetamide (10)

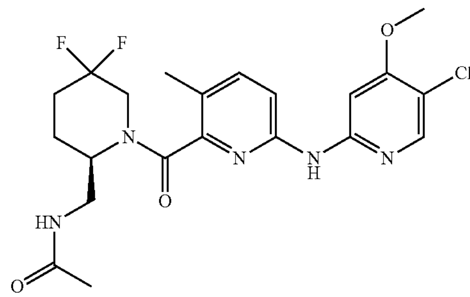 [SMILES: COc1cc(Nc2ccc(C)c(C(=O)N3CC(F)(F)CC[C@@H]3CNC(C)=O)n2)ncc1Cl]

(R)—N-((1-(6-((5-chloro-4-methoxypyridin-2-yl)amino)-3-methylpyridine-2-carbonyl)-5,5-difluoropiperidin-2-yl)methyl)acetamide was obtained by a method similar to the synthesis method of Compound 1 in Example 1. $^1$H NMR (400 MHz, DMSO-$d_6$) δ 9.88 (s, 0.3H), 9.77 (s, 0.7H), 8.11 (s, 1.3H), 7.92 (t, J=6.1 Hz, 0.7H), 7.71-7.53 (m, 3H), 4.86-4.66 (m, 1H), 3.87 (d, J=3.6 Hz, 3H), 3.82-3.38 (m, 1H), 3.30 (d, J=10.7 Hz, 3H), 2.27-1.98 (m, 5H), 1.88-1.56 (m, 5H). LC-MS (m/z): 468.2 $[M+H]^+$.

Example 8: (R)—N-((1-(6-((4-(difluoromethoxy)pyridin-2-yl)amino)-3-methylpyridine-2-carbonyl)-5,5-difluoropiperidin-2-yl)methyl)acetamide (11)

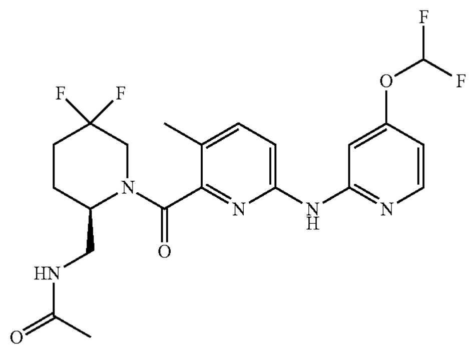 [SMILES: CC(=O)NC[C@H]1CCC(F)(F)CN1C(=O)c1nc(Nc2cc(OC(F)F)ccn2)ccc1C]

(R)—N-((1-(6-((4-(difluoromethoxy)pyridin-2-yl)amino)-3-methylpyridine-2-carbonyl)-5,5-difluoropiperidin-2-yl)methyl)acetamide was obtained by a method similar to the synthesis method of Compound 1 in Example 1. $^1H$ NMR (400 MHz, DMSO-$d_6$) δ 9.97 (s, 0.3H), 9.88 (s, 0.7H), 8.23 (dd, J=5.7, 2.3 Hz, 1H), 8.14 (t, J=6.2 Hz, 0.3H), 7.92 (t, J=6.1 Hz, 0.7H), 7.71-7.49 (m, 3H), 7.35 (d, J=4.9 Hz, 0.7H), 7.17 (d, J=4.9 Hz, 0.3H), 6.72 (t, J=5.5, Hz, 1H), 4.81 (s, 0.3H), 4.73 (s, 0.7H), 3.80-3.38 (m, 2H), 3.30-3.23 (m, 2H), 2.32-2.00 (m, 5H), 1.98-1.78 (dm, 5H). LC-MS (m/z): 470.2 $[M+H]^+$.

Example 9: (R)—N-((1-(6-((1H-pyrrolo[3,2-c]pyridin-6-yl)amino)-3-methylpyridine-2-carbonyl)-5,5-difluoropiperidin-2-yl)methyl)acetamide (12)

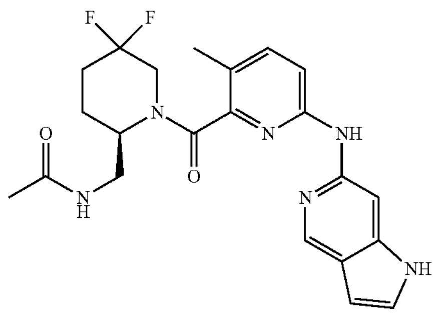 [SMILES: CC(=O)NC[C@H]1CCC(F)(F)CN1C(=O)c1nc(Nc2cc3[nH]ccc3cn2)ccc1C]

(R)—N-((1-(6-((1H-pyrrolo[3,2-c]pyridin-6-yl)amino)-3-methylpyridine-2-carbonyl)-5,5-difluoropiperidin-2-yl)methyl)acetamide was obtained by a method similar to the synthesis method of Compound 1 in Example 1. $^1H$ NMR (400 MHz, DMSO-$d_6$) δ 11.39 (s, 0.5H), 11.08 (s, 0.5H), 9.49 (s, 0.5H), 9.34 (s, 0.5H), 8.50 (d, J=3.4 Hz, 1H), 8.34 (d, J=8.4 Hz, 0.5H), 8.10 (s, 0.5H), 7.88 (d, J=6.1 Hz, 0.5H), 7.72 (s, 0.5H), 7.57-7.48 (m, 1.5H), 7.36-7.19 (m, 1.5H), 6.45 (d, J=2.7 Hz, 1H), 4.90 (s, 0.5H), 4.76 (t, J=13.2 Hz, 0.5H), 3.98-3.40 (m, 3H), 3.30-3.24 (m, 1H), 2.37-2.00 (d, J=8.5 Hz, 5H), 1.99-1.59 (m, 5H). LC-MS (m/z): 443.2 $[M+H]^+$.

Example 10: (R)—N-((1-(6-((5-(t-butyl)isothiazol-3-yl)amino)-3-methylpyridine-2-carbonyl)-5,5-difluoropiperidin-2-yl)methyl)acetamide (13)

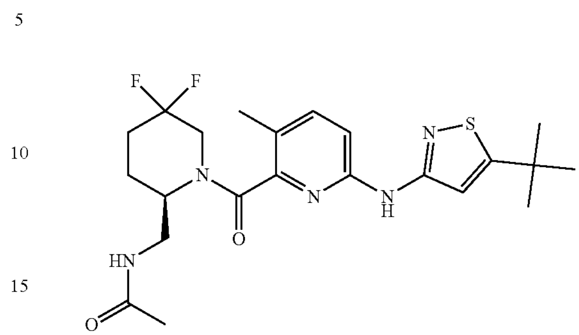

(R)—N-((1-(6-((5-(t-butyl)isothiazol-3-yl)amino)-3-methylpyridine-2-carbonyl)-5,5-difluoropiperidin-2-yl)methyl)acetamide was obtained by a method similar to the synthesis method of Compound 1 in Example 1. $^1H$ NMR (400 MHz, DMSO-$d_6$) δ 10.18 (s, 0.3H), 10.05 (s, 0.7H), 8.13 (t, J=6.1 Hz, 0.3H), 7.92 (t, J=6.0 Hz, 0.7H), 7.84-7.76 (m, 0.3H), 7.67 (d, J 8.6 Hz, 0.7H), 7.60 (dd, J=8.6, 5.8 Hz, 1H), 7.20 (s, 0.7H), 7.13 (s, 0.3H), 4.80 (s, 0.4H), 4.73 (t, J=13.4 Hz, 0.6H), 3.75-3.37 (m, 2H), 3.31-3.23 (m, 2H), 2.35-2.00 (m, 5H), 1.91-1.67 (m, 5H), 1.35 (s, 9H). LC-MS (m/z): 466.2 $[M+H]^+$.

Example 11: (R)—N-((1-(6-((4-(5,6-dihydro-4H-pyrrolo[1,2-b]pyrazol-3-yl)-5-fluoropyridin-2-yl)amino)-3-methylpyridine-2-carbonyl)-5,5-difluoropiperidin-2-yl)methyl)acetamide (14)

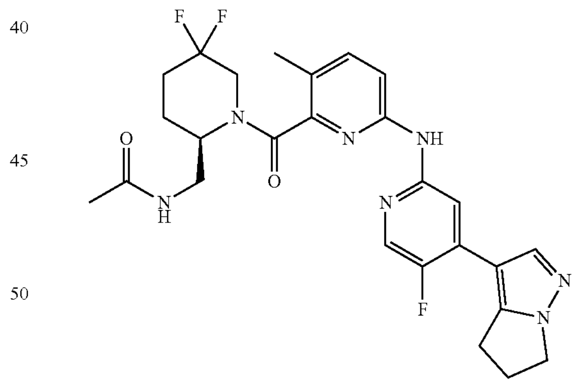

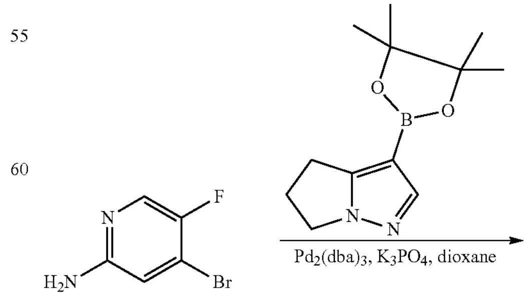

-continued

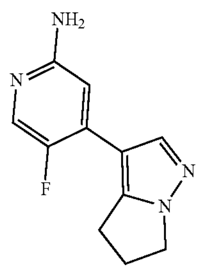

A mixture of 4-bromo-5-fluoropyridin-2-amine (0.19 g, 1 mmol, 1.0 eq.), 3-(3,3,4,4-tetramethyl-1λ$^3$,2,5-bromodioxolan-1-yl)-5,6-dihydro-4H-pyrrolo[1,2-b]pyrazole (0.606 g, 2 mmol, 2.0 eq.), $Pd_2(dba)_3$ (70 mg, 0.01 mmol, 0.1 eq.), BINAP (112 mg, 0.2 mmol, 0.2 eq.) and $K_3PO_4$ (636 mg, 3 mmol, 3.0 eq.) was suspended in 1,4-dioxane (3.0 mL). The resulting mixture was heated to 90° C. to react for 10 h under a nitrogen atmosphere. The reaction solution was purified through column chromatography (Biotage Rening Flash 10 g, EtOAc/n-Hep=100%, methanol/EtOAc=10%) to obtain 4-(5,6-dihydro-4H-pyrrolo[1,2-b]pyrazol-3-yl)-5-fluoropyridin-2-amine. $^1$H NMR (400 MHz, DMSO-d6) δ 7.83 (dd, J=24.6, 3.0 Hz, 2H), 6.57 (d, J=5.5 Hz, 1H), 5.76 (s, 2H), 4.13 (t, J=7.3 Hz, 2H), 3.05 (t, J=7.4 Hz, 2H), 2.68-2.52 (m, 2H). LC-MS (m/z): 219.3 [M+H]$^+$.

(R)—N-((1-(6-((4-(5,6-dihydro-4H-pyrrolo[1,2-b]pyrazol-3-yl)-5-fluoropyridin-2-yl)amino)-3-methylpyridine-2-carbonyl)-5,5-difluoropiperidin-2-yl)methyl)acetamide was obtained by a method similar to the synthesis method of Compound 1 in Example 1. LC-MS (m/z): 528.2 [M+H]$^+$.

Example 12: (R)—N-((1-(6-((5-(3,3-difluorocyclobutyl)-1H-pyrazol-3-yl)amino)-3-methylpyridine-2-carbonyl)-5,5-difluoropiperidin-2-yl)methyl)acetamide (15)

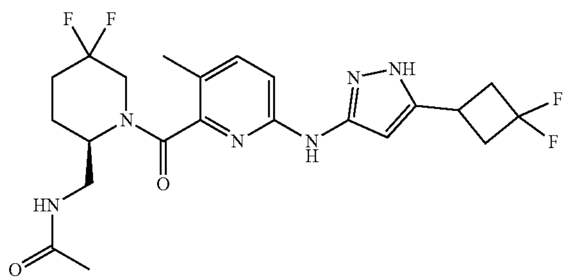 [SMILES: CC(=O)NC[C@H]1CCC(F)(F)CN1C(=O)c1nc(Nc2cc(C3CC(F)(F)C3)[nH]n2)ccc1C]

(R)—N-((1-(6-((5-(3,3-difluorocyclobutyl)-1H-pyrazol-3-yl)amino)-3-methylpyridine-2-carbonyl)-5,5-difluoropiperidin-2-yl)methyl)acetamide was obtained by a method similar to the synthesis method of Compound 1 in Example 1. $^1$H NMR (400 MHz, DMSO-d6) δ 11.95 (s, 1H), 9.29 (s, 1H), 8.11 (t, J=6.2 Hz, 0.3H), 7.93 (t, J=6.1 Hz, 0.7H), 7.47 (d, J=10.5 Hz, 1H), 7.02 (d, J=8.5 Hz, 1H), 6.34 (s, 1H), 4.80 (s, 0.3H), 4.71 (t, J=13.3 Hz, 0.7H), 3.69 (d, J=30.5 Hz, 1H), 3.53-3.40 (m, 2H), 3.22 (dd, J=13.7, 6.7 Hz, 2H), 3.09-2.82 (m, 2H), 2.78-2.58 (m, 2H), 2.37-1.56 (m, 10H). LC-MS (m/z): 483.2 [M+H]$^+$.

Example 13: (R)—N-((1-(6-((4-cyclobutoxypyridin-2-yl)amino)-3-methylpyridine-2-carbonyl)-5,5-difluoropiperidin-2-yl)methyl)acetamide (16)

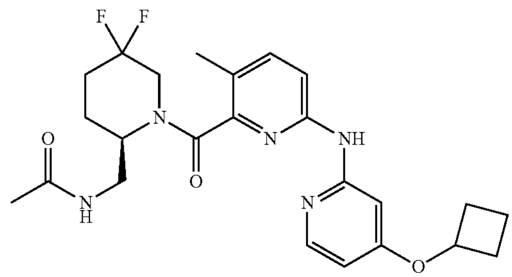 [SMILES: CC(=O)NC[C@H]1CCC(F)(F)CN1C(=O)c1nc(Nc2cc(OC3CCC3)ccn2)ccc1C]

(R)—N-((1-(6-((4-cyclobutoxypyridin-2-yl)amino)-3-methylpyridine-2-carbonyl)-5,5-difluoropiperidin-2-yl)methyl)acetamide was obtained by a method similar to the synthesis method of Compound 1 in Example 1. $^1$H NMR (400 MHz, DMSO-$d_6$) δ 9.70 (s, 0.3H), 9.57 (s, 0.7H), 8.15 (t, J=6.1 Hz, 0.3H), 8.01 (dd, J=5.8, 1.9 Hz, 1H), 7.92 (t, J=6.1 Hz, 0.7H), 7.69-7.53 (m, 2H), 7.32 (d, J=2.3 Hz, 0.3H), 7.28 (d, J=2.3 Hz, 0.7H), 6.40 (dd, J=5.8, 2.3 Hz, 1H), 4.86-4.66 (m, 2H), 3.76-3.35 (m, 2H), 3.32-3.17 (m, 2H), 2.48-2.36 (m, 4H), 2.34-1.97 (m, 6H), 1.96-1.57 (m, 6H). LC-MS (m/z): 474.2 [M+H]$^+$.

Example 14: (R)—N-((1-(6-((4-(t-butyl)pyridin-2-yl)amino)-3-methylpyridine-2-carbonyl)-5,5-difluoropiperidin-2-yl)methyl)acetamide (17)

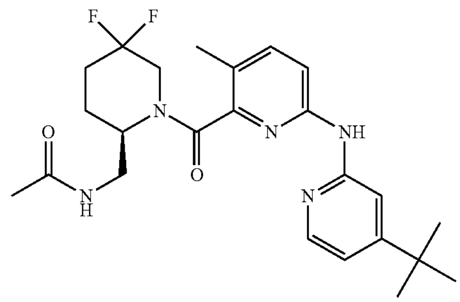 [SMILES: CC(=O)NC[C@H]1CCC(F)(F)CN1C(=O)c1nc(Nc2cc(C(C)(C)C)ccn2)ccc1C]

(R)—N-((1-(6-((4-(t-butyl)pyridin-2-yl)amino)-3-methylpyridine-2-carbonyl)-5,5-difluoropiperidin-2-yl)methyl)acetamide was obtained by a method similar to the synthesis method of Compound 1 in Example 1. $^1$H NMR (400 MHz, Chloroform-d) δ 8.28 (s, 0.6H), 8.18 (d, J=5.6 Hz, 0.4H), 7.78 (d, J=8.7 Hz, 1H), 7.57 (t, J=7.5 Hz, 1H), 7.06-6.91 (m, 1H), 6.29 (s, 1H), 5.04 (d, J=16.6 Hz, 1H), 4.25-4.01 (m, 1H), 3.96-3.80 (m, 1H), 3.73-3.48 (m, 1H), 3.32-3.00 (m, 1H), 2.27 (s, 1H), 2.24 (s, 2H), 2.20-2.03 (m, 2H), 2.00 (s, 2H), 1.98 (s, 1H), 1.95-1.68 (m, 2H), 1.41-1.21 (m, 9H). LC-MS (m/z): 461.3 [M+H]$^+$.

Example 15: (R)—N-((1-(6-((4-(5,6-dihydro-4H-pyrrolo[1,2-b]pyrazol-3-yl)pyridin-2-yl)amino)-3-methylpyridine-2-carbonyl)-5,5-difluoropiperidin-2-yl)methyl)acetamide (18)

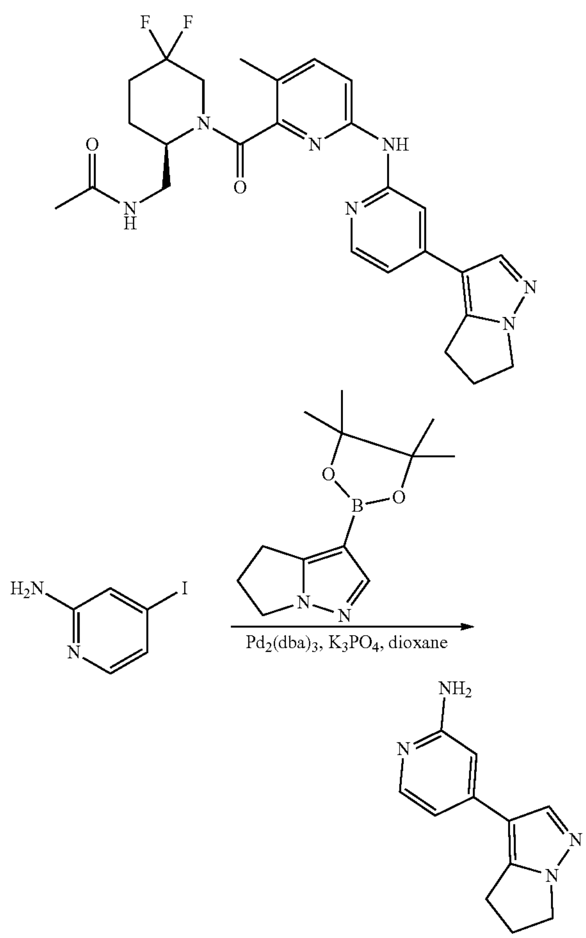

A mixture of 4-iodopyridin-2-amine (0.173 g, 1 mmol, 1.0 eq.), 3-(3,3,4,4-tetramethyl-1λ$^3$,2,5-boradioxolan-1-yl)-5,6-dihydro-4H-pyrrolo[1,2-b]pyrazole (0.606 g, 2 mmol, 2.0 eq.), $Pd_2(dba)_3$ (70 mg, 0.01 mmol, 0.1 eq.), BINAP (112 mg, 0.2 mmol, 0.2 eq.) and $K_3PO_4$ (636 mg, 3 mmol, 3.0 eq.) was suspended in 1,4-dioxane (3.0 mL). The resulting mixture was heated to 90° C. to react for 10 h under a nitrogen atmosphere. The reaction solution was purified through column chromatography (Biotage Rening Flash 10 g, EtOAc/n-Hep=100%, methanol/EtOAc=10%) to obtain 4-(5,6-dihydro-4H-pyrrolo[1,2-b]pyrazol-3-yl)pyridin-2-amine. LC-MS (m/z): 201.1 $[M+H]^+$.

(R)—N-((1-(6-((4-(5,6-dihydro-4H-pyrrolo[1,2-b]pyrazol-3-yl)pyridin-2-yl)amino)-3-methylpyridine-2-carbonyl)-5,5-difluoropiperidin-2-yl)methyl)acetamide was obtained by a method similar to the synthesis method of Compound 1 in Example 1. $^1$H NMR (400 MHz, DMSO-$d_6$) δ 9.71 (s, 0.3H), 9.60 (s, 0.7H), 8.15 (t, J=6.2 Hz, 1H), 7.94-7.52 (m, 4H), 7.03 (dt, J=5.3, 1.7 Hz, 1H), 6.71-6.51 (m, 1H), 4.88-4.69 (m, 1H), 4.10 (q, J=7.2 Hz, 2H), 3.75-3.41 (m, 2H), 3.32-3.16 (m, 2H), 3.12-2.98 (m, 2H), 2.68-2.58 (m, 2H), 2.11 (d, J 16.8 Hz, 5H), 1.93-1.53 (m, 5H). LC-MS (m/z): 510.2 $[M+H]^+$.

Example 16: (R)—N-((5,5-difluoro-1-(3-methyl-6-((4-nitropyridin-2-yl)amino)pyridine-2-carbonyl)piperidin-2-yl)methyl)acetamide (19)

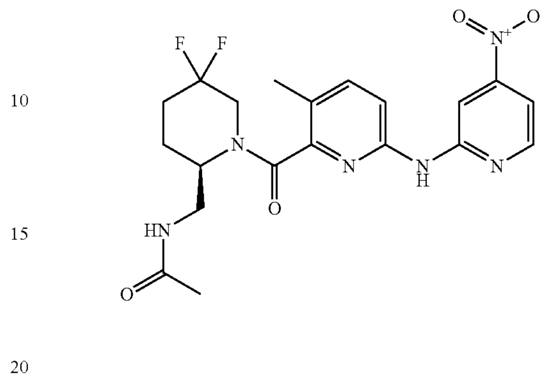

(R)—N-((5,5-difluoro-1-(3-methyl-6-((4-nitropyridin-2-yl)amino)pyridine-2-carbonyl)piperidin-2-yl)methyl)acetamide was obtained by a method similar to the synthesis method of Compound 1 in Example 1. $^1$H NMR (400 MHz, DMSO-$d_6$) δ 10.47 (s, 0.3H), 10.35 (s, 0.7H), 8.67 (d, J 2.1 Hz, 0.3H), 8.55 (d, J=5.5 Hz, 1H), 8.49 (d, J=2.0 Hz, 0.7H), 8.15 (t, J=6.1 Hz, 0.3H), 7.92 (t, J=6.1 Hz, 0.7H), 7.77-7.50 (m, 3H), 4.75 (t, J=13.2 Hz, 1H), 3.80-3.38 (m, 3H), 3.30 (d, J=2.0 Hz, 1H), 2.38-1.97 (m, 5H), 1.93-1.62 (m, 5H). LC-MS (m/z): 449.2 $[M+H]^+$.

Example 17: (R)—N-((1-(6-((4-cyclopentylpyridin-2-yl)amino)-3-methylpyridine-2-carbonyl)-5,5-difluoropiperidin-2-yl)methyl)acetamide (20)

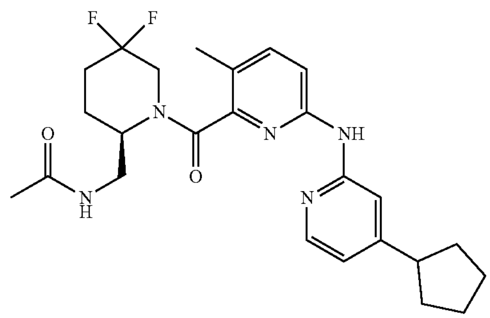 [SMILES: CC(=O)NC[C@H]1CCC(F)(F)CN1C(=O)c1nc(Nc2cc(C3CCCC3)ccn2)ccc1C]

(R)—N-((1-(6-((4-cyclopentylpyridin-2-yl)amino)-3-methylpyridine-2-carbonyl)-5,5-difluoropiperidin-2-yl)methyl)acetamide was obtained by a method similar to the synthesis method of Compound 1 in Example 1. $^1$H NMR (400 MHz, DMSO-$d_6$) δ 9.66 (s, 0.3H), 9.57 (s, 0.7H), 8.23-8.13 (m, 0.4H), 8.09 (d, J=5.1 Hz, 1H), 7.94 (t, J=6.1 Hz, 0.6H), 7.70-7.55 (m, 3H), 6.77 (d, J=5.3 Hz, 1H), 4.81-4.71 (m, 1H), 3.79-3.21 (m, 6H), 2.89 (p, J=8.2 Hz, 1H), 2.37-1.35 (m, 16H). LC-MS (m/z): 472.2$[M+H]^+$.

Example 18: (R)—N-((5,5-difluoro-1-(3-methyl-6-((4-(pyrrolidin-1-yl)pyridin-2-yl)amino)pyridine-2-carbonyl)piperidin-2-yl)methyl)acetamide (21)

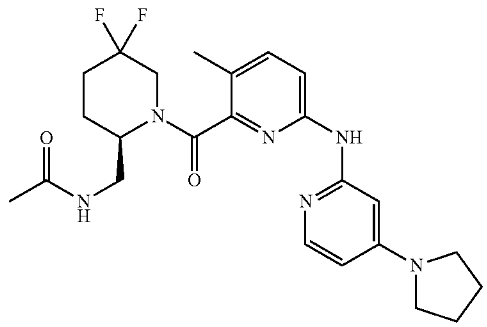 [SMILES: CC(=O)NC[C@H]1CCC(F)(F)CN1C(=O)c1nc(Nc2cc(N3CCCC3)ccn2)ccc1C]

(R)—N-((5,5-difluoro-1-(3-methyl-6-((4-(pyrrolidin-1-yl)pyridin-2-yl)amino)pyridine-2-carbonyl)piperidin-2-yl)methyl)acetamide was obtained by a method similar to the synthesis method of Compound 1 in Example 1. $^1$H NMR (400 MHz, DMSO-$d_6$) δ 9.37 (s, 0.4H), 9.23 (s, 0.6H), 8.15 (s, 0.3H), 7.94 (t, J=6.0 Hz, 0.7H), 7.80 (d, J=5.9 Hz, 1H), 7.73-7.44 (m, 2H), 6.99 (d, J 2.1 Hz, 0.3H), 6.80 (d, J=2.1 Hz, 0.7H), 6.10 (dd, J=5.9, 2.1 Hz, 1H), 4.73 (t, J=13.6 Hz, 1H), 3.78-3.50 (m, 3H), 3.48-3.27 (m, 3H), 2.27-2.04 (d, J=16.0 Hz, 7H), 2.00-1.79 (m, 7H), 1.72 (s, 2H). LC-MS (m/z): 473.2 [M+H]$^+$.

Example 19: (R)—N-((5,5-difluoro-1-(3-methyl-6-(pyridin-2-ylamino)pyridine-2-carbonyl) piperidin-2-yl)methyl)acetamide (22)

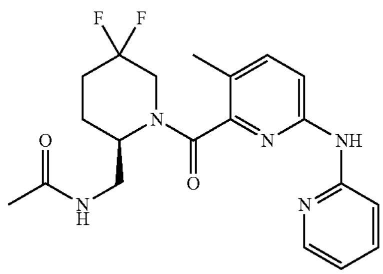 [SMILES: CC(=O)NC[C@H]1CCC(F)(F)CN1C(=O)c1nc(Nc2ccccn2)ccc1C]

(R)—N-((5,5-difluoro-1-(3-methyl-6-(pyridin-2-ylamino)pyridine-2-carbonyl)piperidin-2-yl)methyl)acetamide was obtained by a method similar to the synthesis method of Compound 1 in Example 1. $^1$H NMR (400 MHz, DMSO-$d_6$) δ 9.74 (s, 0.3H), 9.65 (s, 0.7H), 8.22 (dd, J=4.7, 2.7 Hz, 1H), 8.11 (t, J=6.2 Hz, 0.3H), 7.91 (t, J=6.1 Hz, 0.7H), 7.75-7.52 (m, 4H), 6.86 (dd, J=7.1, 4.9 Hz, 1H), 4.82 (s, 0.3H), 4.73 (t, J=13.4 Hz, 0.7H), 3.80-3.60 (m, 1H), 3.55-3.36 (m, 2H), 3.32-3.19 (m, 1H), 2.37-1.98 (m, 5H), 1.93-1.66 (m, 5H). LC-MS (m/z): 404.2 [M+H]$^+$.

Example 20: (R)—N-((5,5-difluoro-1-(3-methyl-6-(pyrimidin-2-ylamino)pyridine-2-carbonyl) piperidin-2-yl)methyl)acetamide (23)

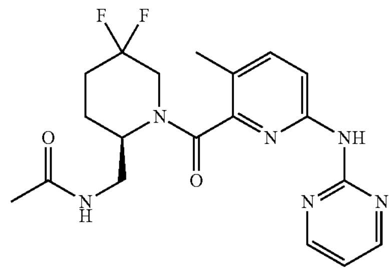 [SMILES: CC(=O)NC[C@H]1CCC(F)(F)CN1C(=O)c1nc(Nc2ncccn2)ccc1C]

(R)—N-((5,5-difluoro-1-(3-methyl-6-(pyrimidin-2-ylamino)pyridine-2-carbonyl)piperidin-2-yl)methyl)acetamide was obtained by a method similar to the synthesis method of Compound 1 in Example 1. $^1$H NMR (400 MHz, DMSO-$d_6$) δ 9.76 (s, 1H), 8.56 (dd, J=4.7, 1.0 Hz, 2H), 8.22 (d, J=8.6 Hz, 0.3H), 8.15 (d, J=8.5 Hz, 0.7H), 8.08 (t, J=6.1 Hz, 0.3H), 7.93 (t, J=6.2 Hz, 0.7H), 7.69 (dd, J=8.6, 5.0 Hz, 1H), 6.96 (t, J=4.8 Hz, 1H), 4.79 (s, 0.3H), 4.71 (t, J=13.5 Hz, 0.7H), 3.75-3.61 (m, 1H), 3.58-3.36 (m, 2H), 3.24 (dt, J=13.4, 6.4 Hz, 1H), 2.37-1.97 (m, 5H), 1.92-1.58 (m, 5H). LC-MS (m/z): 405.2 [M+H]$^+$.

Example 21: (R)—N-((1-(6-((4-chloropyridin-2-yl)amino)-3-methylpyridine-2-carbonyl)-5,5-difluoropiperidin-2-yl)methyl)acetamide (24)

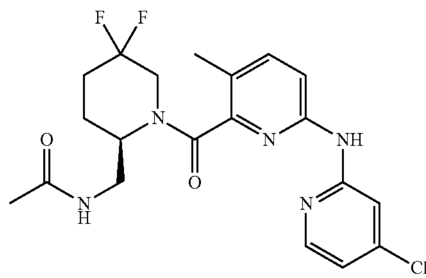 [SMILES: CC(=O)NC[C@H]1CCC(F)(F)CN1C(=O)c1nc(Nc2cc(Cl)ccn2)ccc1C]

(R)—N-((1-(6-((4-chloropyridin-2-yl)amino)-3-methylpyridine-2-carbonyl)-5,5-difluoropiperidin-2-yl)methyl)acetamide was obtained by a method similar to the synthesis method of Compound 1 in Example 1. $^1$H NMR (400 MHz, DMSO-$d_6$) δ 10.03 (s, 0.3H), 9.98 (s, 0.7H), 8.20 (dd, J=5.4, 2.0 Hz, 1H), 8.13 (t, J=6.2 Hz, 0.3H), 8.05 (d, J=1.9 Hz, 0.7H), 7.97-7.85 (m, 1H), 7.66-7.56 (m, 1.3H), 7.47 (d, J=8.5 Hz, 0.7H), 6.99-6.96 (m, 1H), 4.82 (s, 0.4H), 4.73 (t, J 13.3 Hz, 0.6H), 3.74-3.58 (m, 1H), 3.57-3.35 (m, 2H), 3.32-3.22 (m, 1H), 2.34-2.08 (m, 5H), 1.99-1.67 (m, 5H). LC-MS (m/z): 438.1 [M+H]$^+$.

Example 22: (R)—N-((5,5-difluoro-1-(3-methyl-6-(pyrimidin-4-ylamino)pyridine-2-carbonyl) piperidin-2-yl)methyl)acetamide (25)

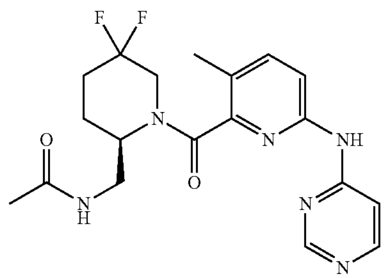 [SMILES: CC(=O)NC[C@H]1CCC(F)(F)CN1C(=O)c1nc(Nc2ccncn2)ccc1C]

(R)—N-((5,5-difluoro-1-(3-methyl-6-(pyrimidin-4-ylamino)pyridine-2-carbonyl)piperidin-2-yl)methyl)acetamide was obtained by a method similar to the synthesis method of Compound 1 in Example 1. $^1$H NMR (400 MHz, DMSO-$d_6$) δ 10.30 (s, 0.3H), 10.22 (s, 0.7H), 8.71 (t, J=1.6 Hz, 1H), 8.43 (d, J=5.9 Hz, 0.3H), 8.39 (d, J=5.9 Hz, 0.7H), 8.13 (t, J=6.2 Hz, 0.3H), 7.91 (t, J=6.1 Hz, 0.7H), 7.80-7.57 (m, 3H), 4.83 (s, 0.4H), 4.73 (t, J=13.3 Hz, 0.6H), 3.83-3.42 (m, 2H), 3.42-3.34 (m, 1H), 3.31-3.26 (m, 1H), 2.28-2.09 (m, 5H), 1.97-1.68 (m, 5H). LC-MS (m/z): 405.2 [M+H]$^+$.

Example 23: (R)—N-((5,5-difluoro-1-(3-methyl-6-(pyrazin-2-ylamino)pyridine-2-carbonyl) piperidin-2-yl)methyl)acetamide (26)

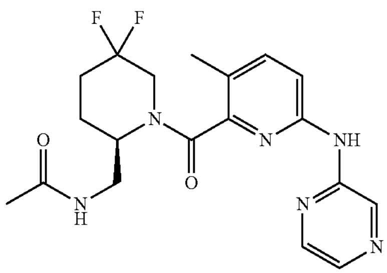 [SMILES: CC(=O)NC[C@H]1CCC(F)(F)CN1C(=O)c1nc(Nc2cnccn2)ccc1C]

(R)—N-((5,5-difluoro-1-(3-methyl-6-(pyrazin-2-ylamino)pyridine-2-carbonyl)piperidin-2-yl)methyl)acetamide was obtained by a method similar to the synthesis method of Compound 1 in Example 1. $^1$H NMR (400 MHz, DMSO-d6) δ 10.13 (s, 0.3H), 10.03 (s, 0.7H), 9.02 (d, J=1.5 Hz, 0.7H), 8.99 (d, J=1.5 Hz, 0.3H), 8.23 (dt, J=2.9, 1.5 Hz, 1H), 8.12 (t, J=6.2 Hz, 0.3H), 8.08 (d, J=2.7 Hz, 1H), 7.91 (t, J=6.1 Hz, 0.7H), 7.67 (d, J=13.4 Hz, 2H), 4.82 (s, 0.3H), 4.73 (t, J=13.4 Hz, 0.7H), 3.75-3.63 (m, 1H), 3.52-3.35 (m, 2H), 3.33-3.22 (m, 1H), 2.34-2.08 (m, 5H), 1.91-1.70 (m, 5H). LC-MS (m/z): 405.2 [M+H]$^+$.

Example 24: (R)—N-((1-(6-((4-(difluoromethyl) pyridin-2-yl)amino)-3-methylpyridine-2-carbonyl)-5,5-difluoropiperidin-2-yl)methyl)acetamide (27)

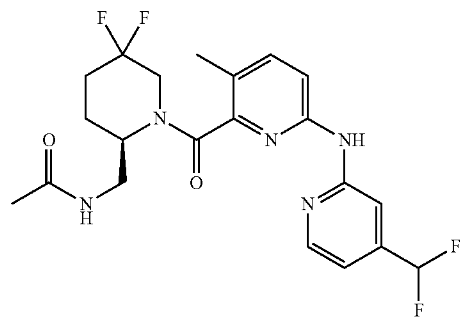 [SMILES: CC(=O)NC[C@H]1CCC(F)(F)CN1C(=O)c1nc(Nc2cc(C(F)F)ccn2)ccc1C]

(R)—N-((1-(6-((4-(difluoromethyl)pyridin-2-yl)amino)-3-methylpyridine-2-carbonyl)-5,5-difluoropiperidin-2-yl) methyl)acetamide was obtained by a method similar to the synthesis method of Compound 1 in Example 1. $^1$H NMR (400 MHz, DMSO-$d_6$) δ 10.07 (s, 0.3H), 9.98 (s, 0.7H), 8.37 (dd, J=5.4, 1.8 Hz, 1H), 8.14 (t, J=6.1 Hz, 0.3H), 7.92 (d, J=6.5 Hz, 1.7H), 7.64 (d, J=6.0 Hz, 2H), 7.26-6.76 (m, 2H), 4.87-4.67 (m, 1H), 3.73-3.61 (m, 1H), 3.58-3.37 (m, 1H), 3.30-3.17 (m, 2H), 2.28-2.00 (m, 5H), 1.95-1.64 (m, 5H). LC-MS (m/z): 454.2 [M+H]$^+$.

Example 25: (R)—N-((5,5-difluoro-1-(6-((4-(fluoromethyl)pyridin-2-yl)amino)-3-methylpyridine-2-carbonyl)piperidin-2-yl)methyl)acetamide (28)

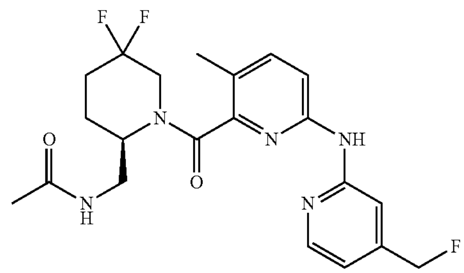 [SMILES: CC(=O)NC[C@H]1CCC(F)(F)CN1C(=O)c1nc(Nc2cc(CF)ccn2)ccc1C]

(R)—N-((5,5-difluoro-1-(6-((4-(fluoromethyl)pyridin-2-yl)amino)-3-methylpyridine-2-carbonyl) piperidin-2-yl) methyl)acetamide was obtained by a method similar to the synthesis method of Compound 1 in Example 1. $^1$H NMR (400 MHz, DMSO-$d_6$) δ 9.88 (s, 0.3H), 9.80 (s, 0.7H), 8.24 (t, J=4.8 Hz, 1H), 8.13 (t, J=6.2 Hz, 0.3H), 7.93 (t, J=6.1 Hz, 0.7H), 7.78 (s, 1H), 7.73-7.66 (m, 0.5H), 7.63-7.58 (m, 1.5H), 6.92-6.81 (m, 1H), 5.51 (s, 0.3H), 5.47 (s, 0.7H), 5.40 (s, 0.3H), 5.36 (s, 0.7H), 4.80 (s, 0.4H), 4.73 (t, J=13.3 Hz, 0.6H), 3.77-3.59 (m, 1H), 3.56-3.37 (m, 1H), 3.32-3.24 (m, 2H), 2.30-2.08 (m, 5H), 1.94-1.64 (m, 5H). LC-MS (m/z): 436.3 [M+H]$^+$.

Example 26: (R)—N-((5,5-difluoro-1-(3-methyl-6-((3-(trifluoromethoxy)pyridin-2-yl)amino) pyridine-2-carbonyl)piperidin-2-yl)methyl)acetamide (29)

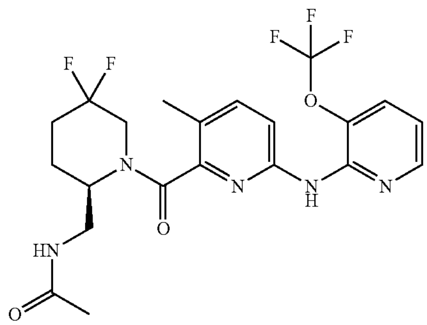 [SMILES: CC(=O)NC[C@H]1CCC(F)(F)CN1C(=O)c1nc(Nc2ncccc2OC(F)(F)F)ccc1C]

(R)—N-((5,5-difluoro-1-(3-methyl-6-((3-(trifluoromethoxy)pyridin-2-yl)amino)pyridine-2-carbonyl)piperidin-2-yl)methyl)acetamide was obtained by a method similar to the synthesis method of Compound 1 in Example 1. $^1$H NMR (400 MHz, DMSO-$d_6$) δ 8.95 (s, 0.3H), 8.89 (s, 0.7H), 8.24 (dd, J=7.7, 4.8, Hz, 1H), 8.07 (t, J=6.2 Hz, 0.3H), 8.01-7.89 (m, 1.7H), 7.79 (d, J 7.1 Hz, 1H), 7.68 (d, J=8.5 Hz, 1H), 7.07-7.02 (m, 1H), 4.78 (s, 0.4H), 4.71 (t, J=13.4 Hz, 0.6H), 3.76-3.60 (m, 1H), 3.56-3.38 (m, 2H), 3.25-3.17 (m, 1H), 2.27-2.06 (m, 5H), 1.82-1.71 (m, 5H). LC-MS (m/z): 488.2 [M+H]$^+$.

Example 27: (R)—N-((5,5-difluoro-1-(3-methyl-6-((4-(trifluoromethyl)pyridin-2-yl)amino)pyridine-2-carbonyl)piperidin-2-yl)methyl)acetamide (30)

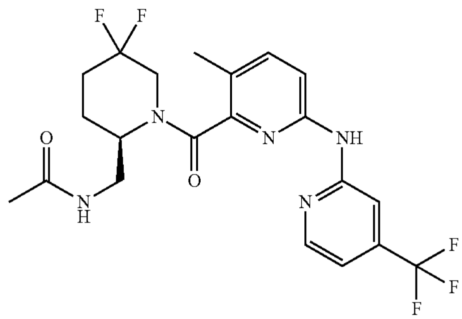 [SMILES: CC(=O)NC[C@H]1CCC(F)(F)CN1C(=O)c1nc(Nc2cc(C(F)(F)F)ccn2)ccc1C]

(R)—N-((5,5-difluoro-1-(3-methyl-6-((4-(trifluoromethyl)pyridin-2-yl)amino)pyridine-2-carbonyl)piperidin-2-yl)methyl)acetamide was obtained by a method similar to the synthesis method of Compound 1 in Example 1. $^1$H NMR (400 MHz, DMSO-$d_6$) δ 10.26 (s, 0.3H), 10.18 (s, 0.7H), 8.48 (d, J=5.0 Hz, 1H), 8.22 (d, J=12.5 Hz, 1H), 8.15 (t, J=6.1 Hz, 0.3H), 7.92 (t, J 6.1 Hz, 0.7H), 7.66 (d, J=8.6, Hz, 1H), 7.56 (d, J=8.5 Hz, 1H), 7.18 (d, J=4.4 Hz, 1H), 4.90-4.64 (m, 1H), 3.75-3.57 (m, 1H), 3.55-3.41 (m, 1H), 3.33-3.16 (m, 2H), 2.32-2.30 (m, 5H), 1.91-1.65 (m, 5H). LC-MS (m/z): 472.2 [M+H]$^+$.

Example 28: (R)-((1-(6-((4-cyanopyridin-2-yl) amino)-3-methylpyridine-2-carbonyl)-5,5-difluoropiperidin-2-yl)methyl)t-butyl carbamate (31)

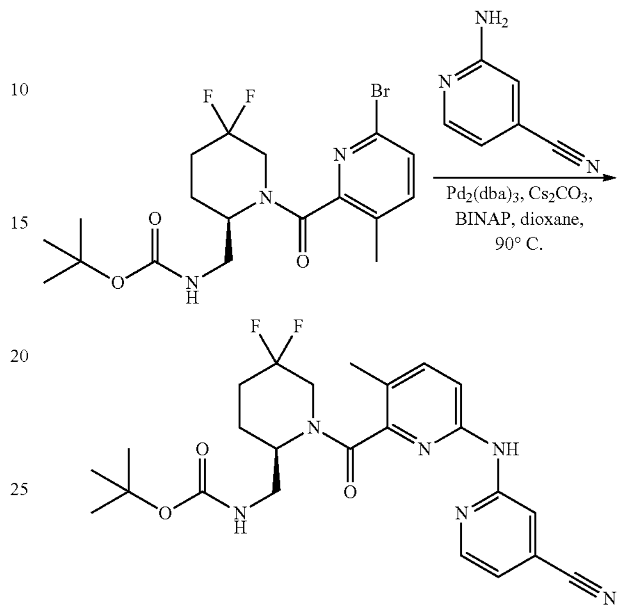

(R)-((1-(6-((4-cyanopyridin-2-yl)amino)-3-methylpyridine-2-carbonyl)-5,5-difluoropiperidin-2-yl)methyl)t-butyl carbamate was obtained by a method similar to the synthesis method of Compound 1 in Example 1. LC-MS (m/z): 487.4 [M+H]$^+$.

Example 29: (R)—N-((5,5-difluoro-1-(3-methyl-6-((4-(trifluoromethoxy)pyridin-2-yl)amino)pyridine-2-carbonyl)piperidin-2-yl)methyl)methanesulfonamide (32)

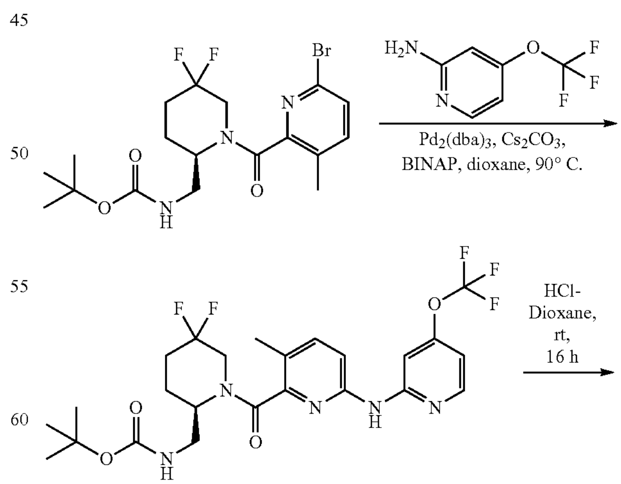

-continued

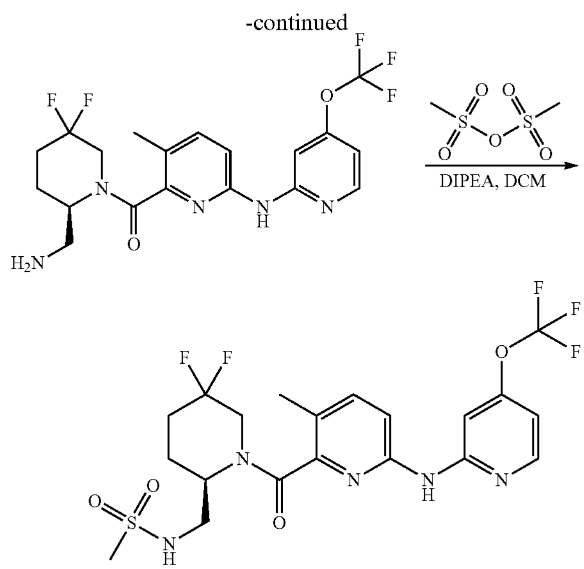

Step 1: (R)-((5,5-difluoro-1-(3-methyl-6-((4-(trifluoromethoxy)pyridin-2-yl)amino)pyridine-2-carbonyl)piperidin-2-yl)methyl)t-butyl carbamate (33)

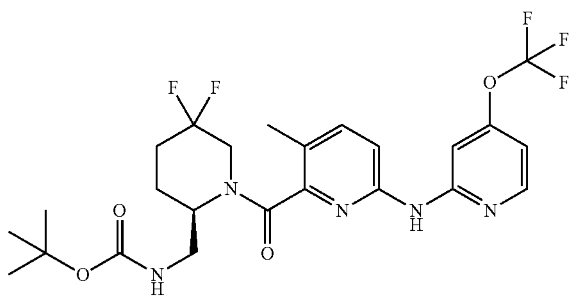 [SMILES: Cc1ccc(Nc2cc(OC(F)(F)F)ccn2)nc1C(=O)N1CC(F)(F)CC[C@@H]1CNC(=O)OC(C)(C)C]

(R)-((5,5-difluoro-1-(3-methyl-6-((4-(trifluoromethoxy)pyridin-2-yl)amino)pyridine-2-carbonyl)piperidin-2-yl)methyl)t-butyl carbamate was obtained by a method similar to the synthesis method of Compound 31 in Example 28. LC-MS (m/z): 546.2[M+H]+.

Step 2: (R)-(2-(aminomethyl)-5,5-difluoropiperidin-1-yl)(3-methyl-6-((4-(trifluoromethoxy)pyridin-2-yl)amino)pyridin-2-yl)methanone (34)

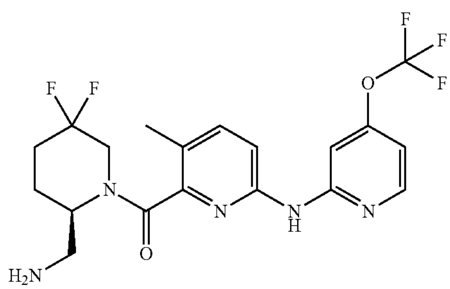 [SMILES: Cc1ccc(Nc2cc(OC(F)(F)F)ccn2)nc1C(=O)N1CC(F)(F)CC[C@@H]1CN]

(R)-(2-(aminomethyl)-5,5-difluoropiperidin-1-yl)(3-methyl-6-((4-(trifluoromethoxy)pyridin-2-yl)amino)pyridin-2-yl)methanone was obtained by a method similar to the synthesis method of Compound 3 in Example 1. LC-MS (m/z): 446.2 [M+H]+.

Step 3: (R)—N-((5,5-difluoro-1-(3-methyl-6-((4-(trifluoromethoxy)pyridin-2-yl)amino)pyridine-2-carbonyl)piperidin-2-yl)methyl)methanesulfonamide (32)

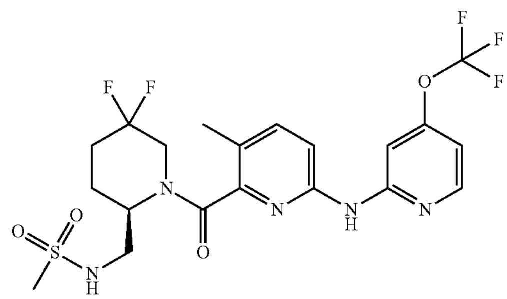 [SMILES: Cc1ccc(Nc2cc(OC(F)(F)F)ccn2)nc1C(=O)N1CC(F)(F)CC[C@@H]1CNS(C)(=O)=O]

With stirring, (R)-(2-(aminomethyl)-5,5-difluoropiperidin-1-yl)(3-methyl-6-((4-(trifluoromethoxy)pyridin-2-yl)amino)pyridin-2-yl)methanone (45 mg, 0.1 mmol, 1 eq.) was dissolved in DCM (5 mL), and methanesulfonic anhydride (35 mg, 0.2 mmol, 2 eq.) was added at a temperature of an ice water bath. The reaction mixture was stirred at 0° C. for half an hour, and then DIPEA (39 mg, 0.3 mmol, 3 eq.) was added. The reaction mixture was stirred overnight at ambient temperature. The reaction mixture was treated with water and EtOAc, and the organic phase was isolated. The organic phase was washed with water, dried over $MgSO_4$, and concentrated to dryness. The crude product was purified through column chromatography (Biotage Rening Flash 80 g, EtOAc/n-Hep=80%-100%) to obtain the title compound (25 mg, 47.80%). $^1$H NMR (400 MHz, DMSO-$d_6$) δ 10.17 (s, 0.3H), 10.11 (s, 0.7H), 8.32 (dd, J=5.7, 3.0 Hz, 1H), 7.96 (s, 0.7H), 7.85 (s, 0.3H), 7.70-7.45 (m, 2H), 7.39 (t, J=6.6 Hz, 0.3H), 7.12 (t, J=6.6 Hz, 0.7H), 6.94-6.82 (m, 1H), 4.80 (s, 0.3H), 4.72 (t, J=13.3 Hz, 0.7H), 3.71-3.36 (m, 2H), 3.30-3.20 (m, 1H), 3.19-3.06 (m, 1H), 2.97 (s, 1H), 2.79 (s, 2H), 2.31-1.65 (m, 7H). LC-MS (m/z): 524.1 [M+H]+.

Example 30: (R)—N-((1-(6-((4-ethoxypyridin-2-yl)amino)-3-methylpyridine-2-carbonyl)-5,5-difluoropiperidin-2-yl)methyl)acetamide (35)

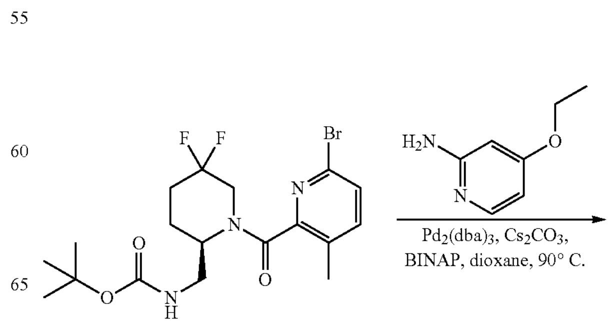

-continued

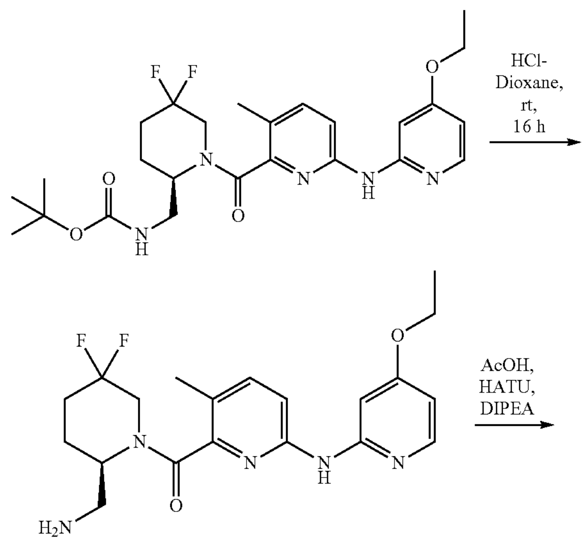

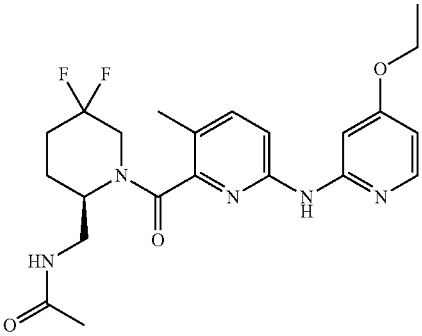

Step 1: (R)-((1-(6-((4-ethoxypyridin-2-yl)amino)-3-methylpyridine-2-carbonyl)-5,5-difluoropiperidin-2-yl)methyl)t-butyl carbamate (36)

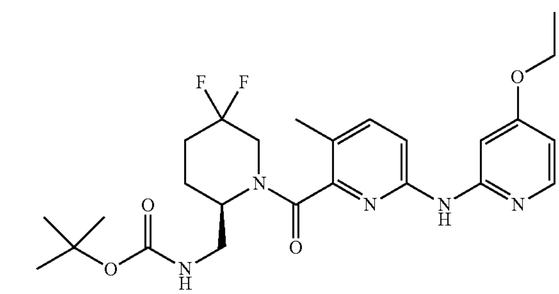 [SMILES: CCOc1ccnc(Nc2ccc(C)c(C(=O)N3CC(F)(F)CC[C@@H]3CNC(=O)OC(C)(C)C)n2)c1]

(R)-((1-(6-((4-ethoxypyridin-2-yl)amino)-3-methylpyridine-2-carbonyl)-5,5-difluoropiperidin-2-yl)methyl)t-butyl carbamate was obtained by a method similar to the synthesis method of Compound 31 in Example 28. $^1H$ NMR (400 MHz, Chloroform-d) δ 8.14-8.02 (m, 0.7H), 7.86 (d, J=8.6 Hz, 0.3H), 7.59-7.46 (m, 1H), 7.19 (s, 1H), 6.65-6.39 (m, 2H), 5.17-5.00 (m, 1H), 4.08 (q, J=6.9, 5.9 Hz, 2H), 3.96-3.36 (m, 3H), 3.24-2.97 (m, 1H), 2.29 (s, 2H), 2.25 (s, 1H), 2.22-1.84 (m, 4H), 1.79-1.27 (m, 12H). LC-MS (m/z): 506.3 $[M+H]^+$.

Step 2: (R)-(2-(aminomethyl)-5,5-difluoropiperidin-1-yl)(6-((4-ethoxypyridin-2-yl)amino)-3-methylpyridin-2-yl)methanone (37)

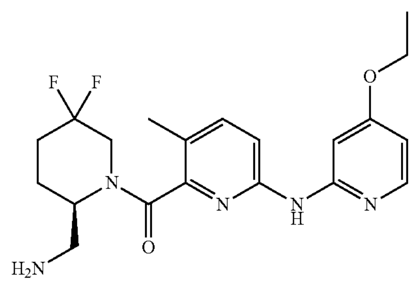 [SMILES: CCOc1ccnc(Nc2ccc(C)c(C(=O)N3CC(F)(F)CC[C@@H]3CN)n2)c1]

(R)-(2-(aminomethyl)-5,5-difluoropiperidin-1-yl)(6-((4-ethoxypyridin-2-yl)amino)-3-methylpyridin-2-yl)methanone was obtained by a method similar to the synthesis method of Compound 3 in Example 1. $^1H$ NMR (400 MHz, Methanol-$d_4$) δ 8.03 (t, J=6.2 Hz, 1H), 7.68 (dd, J=12.0, 8.8 Hz, 1H), 7.52 (d, J=8.5 Hz, 1H), 6.88 (d, J=2.3 Hz, 0.4H), 6.80 (d, J=2.2 Hz, 0.6H), 6.57 (dd, J=5.8, 2.0 Hz, 1H), 5.20-4.94 (m, 1H), 4.20-4.06 (m, 2H), 3.71-3.48 (m, 2H), 3.27-3.00 (m, 2H), 2.29-1.74 (m, 7H), 1.43 (td, J=7.0, 1.5 Hz, 3H). LC-MS (m/z): 406.2 $[M+H]^+$.

Step 3: (R)—N-((1-(6-((4-ethoxypyridin-2-yl)amino)-3-methylpyridine-2-carbonyl)-5,5-difluoropiperidin-2-yl)methyl)acetamide (35)

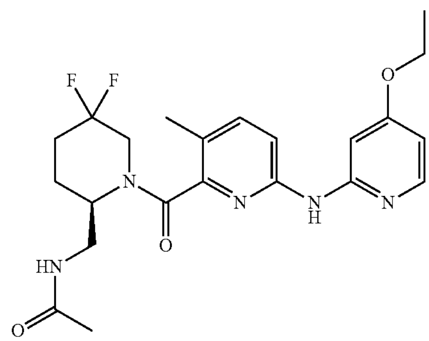 [SMILES: CCOc1ccnc(Nc2ccc(C)c(C(=O)N3CC(F)(F)CC[C@@H]3CNC(C)=O)n2)c1]

(R)—N-((1-(6-((4-ethoxypyridin-2-yl)amino)-3-methylpyridine-2-carbonyl)-5,5-difluoropiperidin-2-yl)methyl) acetamide was obtained by a method similar to the synthesis method of Compound 4 in Example 1. $^1H$ NMR (400 MHz, DMSO-$d_6$) δ 9.67 (s, 0.3H), 9.56 (s, 0.7H), 8.13 (s, 1H), 8.03 (d, J=5.5 Hz, 1H), 7.92 (s, 0.4H), 7.75-7.66 (m, 0.6H), 7.59 (q, J=8.7, 8.3 Hz, 1H), 7.37 (s, 1H), 6.49 (d, J=5.6 Hz, 1H), 6.11 (d, J=5.7 Hz, 0.6H), 5.95 (s, 0.4H), 5.80 (s, 1H), 4.76 (dd, J=28.5, 14.7 Hz, 1H), 4.22-3.90 (m, 3H), 3.70 (s, 1H), 2.28-2.09 (m, 5H), 1.92-1.68 (m, 5H), 1.32 (dt, J=10.4, 6.8 Hz, 3H). LC-MS (m/z): 448.2 $[M+H]^+$.

Example 31: (4,4-Difluoroazepin-1-yl)(3-methyl-6-((4-(trifluoromethoxy)pyridin-2-yl)amino)pyridin-2-yl)methanone (38)

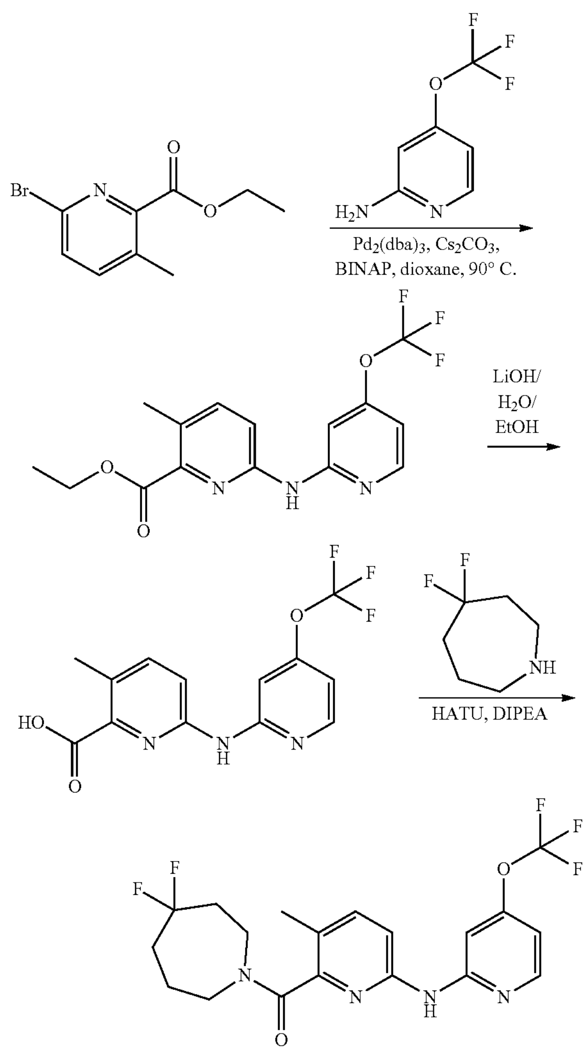

Step 1: Ethyl 3-methyl-6-((4-(trifluoromethoxy)pyridin-2-yl)amino)picolinate (39)

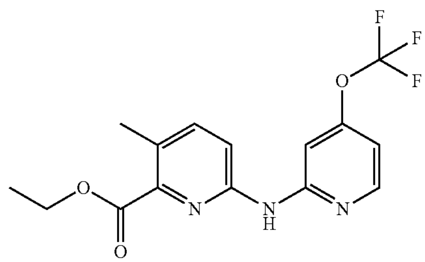 [SMILES: CCOC(=O)c1nc(Nc2cc(OC(F)(F)F)ccn2)ccc1C]

Ethyl 3-methyl-6-((4-(trifluoromethoxy)pyridin-2-yl)amino)picolinate was obtained by a method similar to the synthesis method of Compound 1 in Example 1. LC-MS (m/z): 342.1 $[M+H]^+$.

Step 2: 3-Methyl-6-((4-(trifluoromethoxy)pyridin-2-yl)amino)picolinic acid (40)

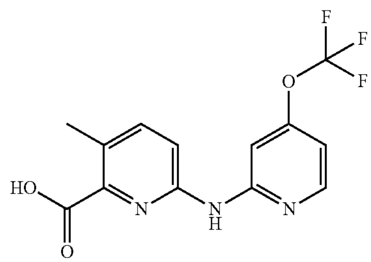 [SMILES: Cc1ccc(Nc2cc(OC(F)(F)F)ccn2)nc1C(=O)O]

With stirring, ethyl 3-methyl-6-((4-(trifluoromethoxy)pyridin-2-yl)amino)picolinate (0.5 g, 1.47 mmol, 1.0 eq.) and LiOH monohydrate (614.75 mg, 14.65 mmol, 10.0 eq.) were dissolved in $H_2O$/EtOH (1:5) and stirred for 3 h at room temperature. The reaction mixture was neutralized with 2N HCl to pH=4 and extracted with EtOAc. The organic phase was dried over $MgSO_4$ and dried in vacuum to obtain 3-methyl-6-((4-(trifluoromethoxy)pyridin-2-yl)amino)picolinic acid. LC-MS (m/z): 314.1 $[M+H]^+$.

Step 3: (4,4-Difluoroazepin-1-yl)(3-methyl-6-((4-(trifluoromethoxy)pyridin-2-yl)amino)pyridin-2-yl)methanone (38)

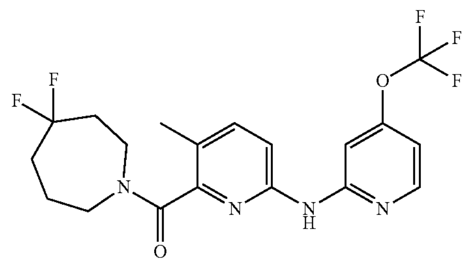 [SMILES: Cc1ccc(Nc2cc(OC(F)(F)F)ccn2)nc1C(=O)N1CCCC(F)(F)CC1]

(4,4-Difluoroazepin-1-yl)(3-methyl-6-((4-(trifluoromethoxy)pyridin-2-yl)amino)pyridin-2-yl) methanone was obtained by a method similar to the synthesis method of Compound 2 in Example 1. $^1H$ NMR (400 MHz, DMSO-$d_6$) δ 10.15 (d, J=2.4 Hz, 1H), 8.32 (d, J=5.7 Hz, 1H), 7.85 (d, J=11.9 Hz, 1H), 7.70-7.51 (m, 2H), 6.86 (d, J=5.8 Hz, 1H), 3.78-3.51 (m, 2H), 3.26 (t, J=6.2 Hz, 2H), 2.38-2.20 (m, 1H), 2.14-2.06 (m, 5H), 1.93-1.64 (m, 3H). LC-MS (m/z): 431.1 $[M+H]^+$.

Example 32: (R)-((1-(3-methyl-6-((4-(trifluoromethoxy)pyridin-2-yl)amino)pyridine-2-carbonyl) piperidin-2-yl)methyl)t-butyl carbamate (41)

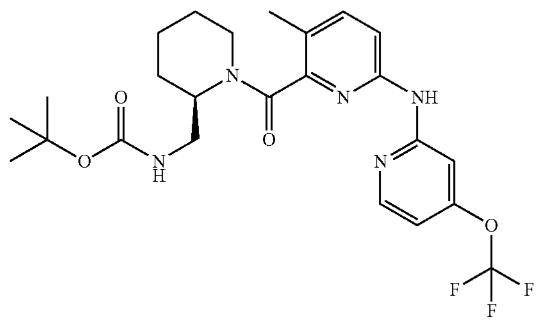 [SMILES: Cc1ccc(Nc2cc(OC(F)(F)F)ccn2)nc1C(=O)N1CCCC[C@@H]1CNC(=O)OC(C)(C)C]

(R)-((1-(3-methyl-6-((4-(trifluoromethoxy)pyridin-2-yl) amino)pyridine-2-carbonyl)piperidin-2-yl)methyl)t-butyl carbamate was obtained by a method similar to the synthesis method of Compound 38 in Example 31. LC-MS (m/z): 510.1 $[M+H]^+$.

Example 33: (S)—N-(5,5-difluoro-1-(3-methyl-6-((4-(trifluoromethoxy)pyridin-2-yl)amino)pyridine-2-carbonyl)piperidin-3-yl)acetamide (42)

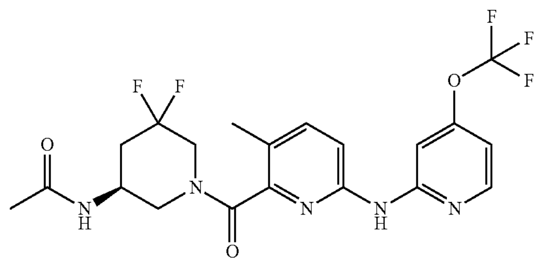 [SMILES: CC(=O)N[C@@H]1CN(C(=O)c2nc(Nc3cc(OC(F)(F)F)ccn3)ccc2C)CC(F)(F)C1]

(S)—N-(5,5-difluoro-1-(3-methyl-6-((4-(trifluoromethoxy)pyridin-2-yl)amino)pyridine-2-carbon yl)piperidin-3-yl)acetamide was obtained by a method similar to the synthesis method of Compound 38 in Example 31. $^1$H NMR (400 MHz, DMSO-$d_6$) δ 10.18 (s, 0.3H), 10.12 (s, 0.7H), 8.32 (dd, J=5.8, 1.6 Hz, 1H), 8.09 (d, J=7.5 Hz, 0.3H), 7.92 (d, J=7.1 Hz, 0.7H), 7.82-7.60 (m, 3H), 6.86 (d, J=5.7 Hz, 1H), 4.73-4.51 (m, 1H), 4.14-3.80 (m, 1H), 3.70-3.38 (m, 3H), 2.35 (d, J=14.7 Hz, 1H), 2.22-1.94 (m, 4H), 1.87 (s, 1H), 1.70 (s, 2H). LC-MS (m/z): 474.2 $[M+H]^+$.

Example 34: (R)—N-(5,5-difluoro-1-(3-methyl-6-((4-(trifluoromethoxy)pyridin-2-yl)amino)pyridine-2-carbonyl)piperidin-3-yl)acetamide (43)

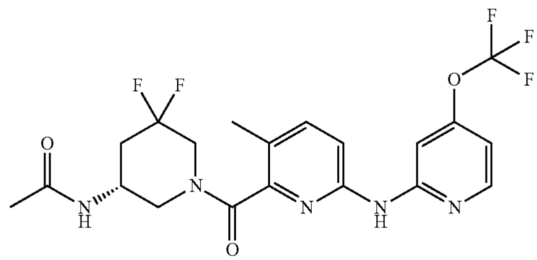 [SMILES: CC(=O)N[C@H]1CN(C(=O)c2nc(Nc3cc(OC(F)(F)F)ccn3)ccc2C)CC(F)(F)C1]

(R)—N-(5,5-difluoro-1-(3-methyl-6-((4-(trifluoromethoxy)pyridin-2-yl)amino)pyridine-2-carbon yl)piperidin-3-yl)acetamide was obtained by a method similar to the synthesis method of Compound 38 in Example 31. $^1$H NMR (400 MHz, DMSO-$d_6$) δ 10.18 (s, 0.3H), 10.12 (s, 0.7H), 8.32 (dd, J=5.7, 1.6 Hz, 1H), 8.09 (d, J=7.5 Hz, 0.3H), 7.92 (d, J=7.1 Hz, 0.7H), 7.84-7.59 (m, 3H), 6.86 (d, J=5.7 Hz, 1H), 4.66 (s, 1H), 3.86 (s, 1H), 3.69-3.38 (m, 3H), 2.43-2.29 (m, 1H), 2.22-1.95 (m, 4H), 1.78 (d, J=69.0 Hz, 3H). LC-MS (m/z): 474.2 $[M+H]^+$.

Example 35: N-((5,5-difluoro-1-(3-methyl-6-((4-(trifluoromethoxy)pyridin-2-yl)amino)pyridine-2-carbonyl)piperidin-2-yl)methyl)acetamide (44)

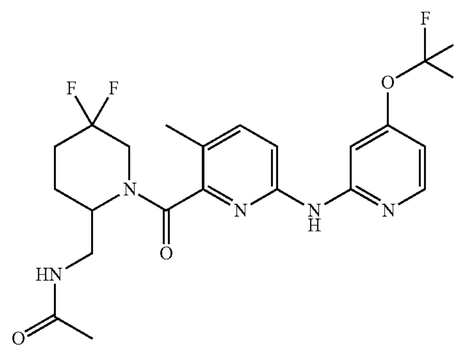

N-((5,5-difluoro-1-(3-methyl-6-((4-(trifluoromethoxy) pyridin-2-yl)amino)pyridine-2-carbonyl) piperidin-2-yl) methyl)acetamide was obtained by a method similar to the synthesis method of Compound 38 in Example 31. $^1$H NMR (400 MHz, DMSO-$d_6$) δ 10.15 (s, 0.3H), 10.10 (s, 0.7H), 8.32 (dd, J=5.7, 4.4 Hz, 1H), 8.15 (t, J=6.1 Hz, 0.3H), 7.98-7.86 (m, 1.7H), 7.64 (dd, J=8.7, 1.8 Hz, 1H), 7.56 (d, J=8.5 Hz, 0.3H), 7.49 (d, J=8.5 Hz, 0.7H), 6.87 (d, J=2.4 Hz, 1H), 4.82 (s, 0.3H), 4.72 (t, J=13.3 Hz, 0.7H), 3.74-3.37 (m, 3H), 3.32-3.11 (m, 1H), 2.35-1.96 (m, 5H), 1.93-1.66 (m, 5H). LC-MS (m/z): 488.2 $[M+H]^+$.

Example 36: (R)—N-((1-(3-methyl-6-((4-(trifluoromethoxy)pyridin-2-yl)amino)pyridine-2-carbonyl) piperidin-2-yl)methyl)acetamide (45)

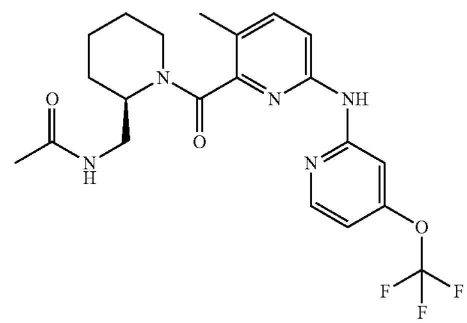 [SMILES: CC(=O)NC[C@H]1CCCCN1C(=O)c1nc(Nc2cc(OC(F)(F)F)ccn2)ccc1C]

(R)—N-((1-(3-methyl-6-((4-(trifluoromethoxy)pyridin-2-yl)amino)pyridine-2-carbonyl)piperidin-2-yl)methyl)acetamide was obtained by a method similar to the synthesis method of Compound 38 in Example 31. $^1$H NMR (400

MHz, DMSO-$d_6$) δ 10.14 (s, 0.7H), 10.08 (s, 0.3H), 8.32 (d, J 5.7 Hz, 1H), 8.12-7.80 (m, 2H), 7.60 (dd, J=8.5, 3.8 Hz, 1H), 7.52 (d, J=8.5 Hz, 0.6H), 7.44 (d, J=8.4 Hz, 0.4H), 6.87 (d, J=5.6 Hz, 1H), 4.78 (q, J=7.2 Hz, 0.5H), 4.47 (dd, J 9.7, 5.2 Hz, 0.5H), 3.75-3.48 (m, 3H), 3.27-2.76 (m, 4H), 2.15 (s, 1H), 2.11 (s, 2H), 2.02-1.33 (m, 6H). LC-MS (m/z): 452.2 $[M+H]^+$.

Example 37: (Hexahydro-1H-pyrrolo[1,2-a][1,4]diazepin-2-2(3H)-yl)(3-methyl-6-((4-(trifluoromethoxy)pyridin-2-yl)amino)pyridin-2-yl)methanone (46)

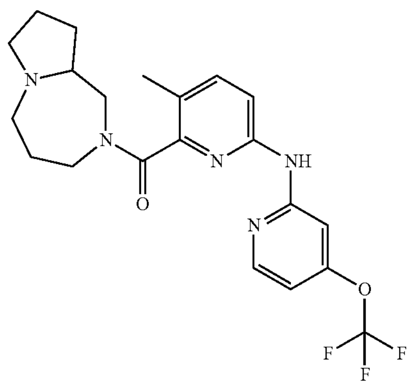 [SMILES: Cc1ccc(Nc2cc(OC(F)(F)F)ccn2)nc1C(=O)N1CCCN2CCCC2C1]

(Hexahydro-1H-pyrrolo[1,2-a][1,4]diazepin-2-2(3H)-yl)(3-methyl-6-((4-(trifluoromethoxy)pyridin-2-yl)amino)pyridin-2-yl)methanone was obtained by a method similar to the synthesis method of Compound 38 in Example 31. $^1H$ NMR (400 MHz, DMSO-$d_6$) δ 10.13 (s, 1H), 8.32 (d, J=5.6 Hz, 1H), 8.17 (s, 1H), 7.82 (d, J=16.8 Hz, 1H), 7.71-7.46 (m, 1H), 6.86 (d, J 5.7 Hz, 1H), 4.14 (dd, J=13.7, 2.5 Hz, 1H), 3.69 (q, J=5.3 Hz, 1H), 3.42-3.23 (m, 2H), 3.15-2.87 (m, 3H), 2.70-2.59 (m, 1H), 2.48-2.23 (m, 2H), 2.21-2.12 (m, 3H), 2.02 (ddd, J 17.2, 7.8, 3.7 Hz, 1H), 1.93-1.83 (m, 1H), 1.82-1.41 (m, 3H). LC-MS (m/z): 436.2 $[M+H]^+$.

Example 38: (5,5-Difluoro-1-(3-methyl-6-((4-(trifluoromethoxy)pyridin-2-yl)amino)pyridine-2-carbonyl)piperidin-2-yl)(pyrrolidin-1-yl)methanone (47)

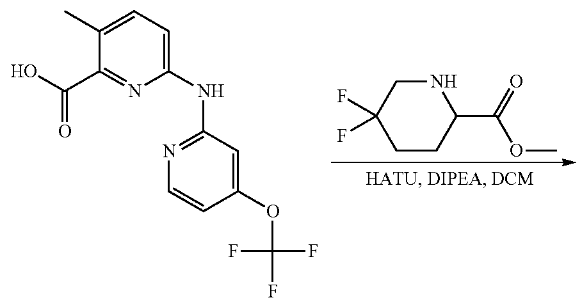

-continued

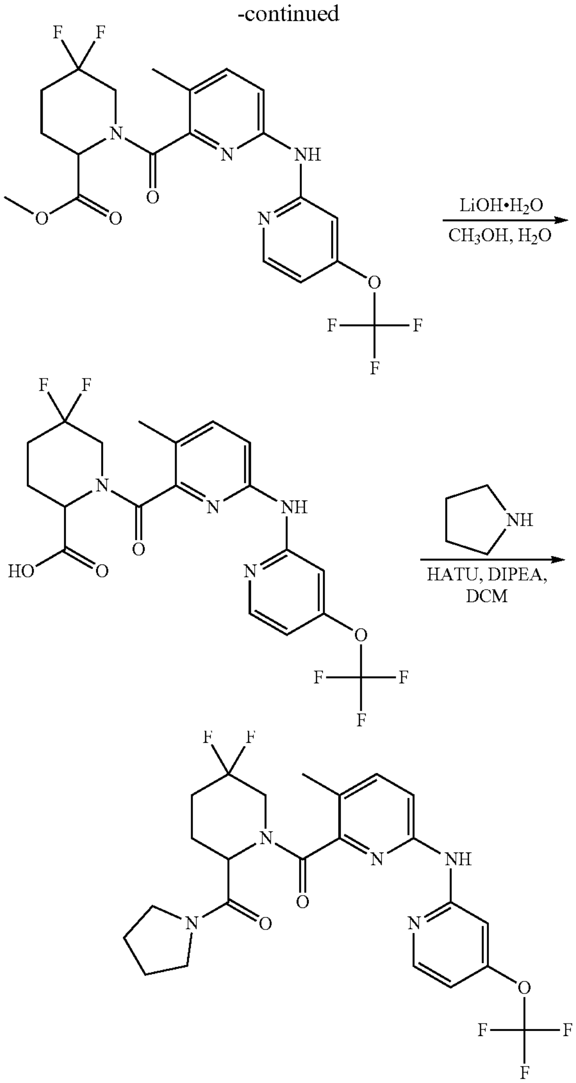

Step 1: 5,5-Difluoro-1-(3-methyl-6-((4-(trifluoromethoxy)pyridin-2-yl)amino)pyridine-2-carbonyl)piperidine-2-methyl formate (47-1)

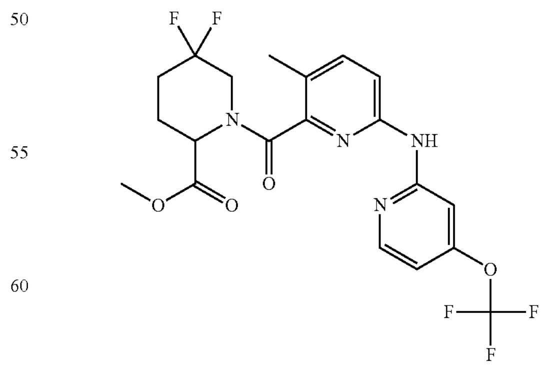

With stirring, 3-methyl-6-((4-(trifluoromethoxy)pyridin-2-yl)amino)picolinic acid (0.313 g, 1.0 mmol, 1 eq.) was dissolved in DCM (5 mL), and DIPEA (0.39 g, 3.0 mmol, 3 eq.) and HATU (0.57 g, 1.50 mmol, 1.5 eq.) were added at a temperature of an ice water bath. The reaction mixture was stirred at 0° C. for half an hour, and then methyl 5,5-difluoropiperidine-2-carboxylate (0.2 g, 1.10 mmol, 1.1 eq.) was added. The reaction mixture was stirred overnight at ambient temperature. The reaction mixture was treated with water and EtOAc, and the organic phase was isolated. The organic phase was washed with water, dried over $MgSO_4$, and concentrated to dryness. The crude product was purified through column chromatography (Biotage Rening Flash 25 g, EtOAc/n-Hep=20%-50%) to obtain the title compound (0.32 g, 67.01%).

Step 2: 5,5-Difluoro-1-(3-methyl-6-((4-(trifluoromethoxy)pyridin-2-yl)amino)pyridine-2-carbonyl)piperidine-2-carboxylic acid (47-2)

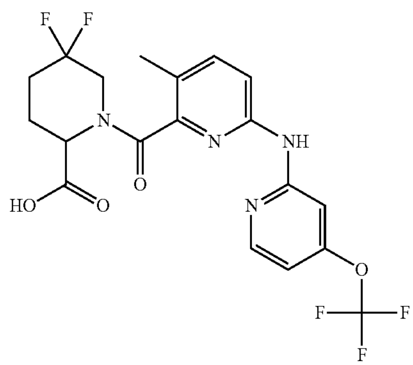 [SMILES: Cc1ccc(Nc2cc(OC(F)(F)F)ccn2)nc1C(=O)N1CC(F)(F)CCC1C(=O)O]

With stirring, 5,5-difluoro-1-(3-methyl-6-((4-(trifluoromethoxy)pyridin-2-yl)amino)pyridine-2-carbonyl)piperidine-2-methyl formate (0.25 g, 0.53 mmol, 1.0 eq.) and LiOH monohydrate (222.4 mg, 5.3 mmol, 10.0 eq.) were dissolved in $H_2O$/EtOH (1:5) and stirred for 3 h at room temperature. The reaction mixture was neutralized with 2N HCl to pH=4 and extracted with EtOAc. The organic phase was dried over $MgSO_4$ and dried in vacuum to obtain the title compound. LC-MS (m/z): 461.4 $[M+H]^+$.

Step 3: (5,5-Difluoro-1-(3-methyl-6-((4-(trifluoromethoxy)pyridin-2-yl)amino)pyridine-2-carbonyl)piperidin-2-yl)(pyrrolidin-1-yl)methanone (47)

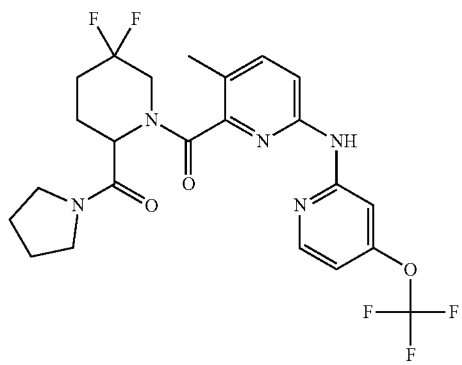 [SMILES: Cc1ccc(Nc2cc(OC(F)(F)F)ccn2)nc1C(=O)N1CC(F)(F)CCC1C(=O)N1CCCC1]

With stirring, 5,5-difluoro-1-(3-methyl-6-((4-(trifluoromethoxy)pyridin-2-yl)amino)pyridine-2-carbonyl)piperidine-2-carboxylic acid (0.12 g, 0.25 mmol, 1.0 eq.) was dissolved in DCM (5 mL), and DIPEA (0.097 g, 0.75 mmol, 3 eq.) and HATU (0.14 g, 0.38 mmol, 1.5 eq.) were added at a temperature of an ice water bath. The reaction mixture was stirred at 0° C. for half an hour, and then tetrahydropyrrole (0.36 g, 0.5 mmol, 2.0 eq.) was added. The reaction mixture was stirred overnight at ambient temperature. The reaction mixture was treated with water and EtOAc, and the organic phase was isolated. The organic phase was washed with water, dried over $MgSO_4$, and concentrated to dryness. The crude product was purified through column chromatography (Biotage Rening Flash 80 g, EtOAc/n-Hep=20%-50%) to obtain (5,5-difluoro-1-(3-methyl-6-((4-(trifluoromethoxy)pyridin-2-yl)amino)pyridine-2-carbonyl)piperidin-2-yl)(pyrrolidin-1-yl)methanone. $^1$H NMR (400 MHz, DMSO-d6) δ 10.18 (s, 1H), 8.33 (d, J 5.7 Hz, 1H), 7.86-7.58 (m, 3H), 6.88 (d, J=5.6 Hz, 1H), 5.46 (s, 0.4H), 4.70 (t, J=13.8 Hz, 0.6H), 4.22 (s, 1H), 4.05-3.87 (m, 1H), 3.71-3.43 (m, 2H), 3.17-3.01 (m, 2H), 2.38-1.99 (m, 5H), 1.98-1.69 (m, 4H), 1.67-1.20 (m, 2H). LC-MS (m/z): 514.3 $[M+H]^+$.

Example 39: (R)-1-((5,5-difluoro-1-(3-methyl-6-((4-(trifluoromethoxy)pyridin-2-yl)amino)pyridine-2-carbonyl)piperidin-2-yl)methyl)pyrrolidinone-2-one (48)

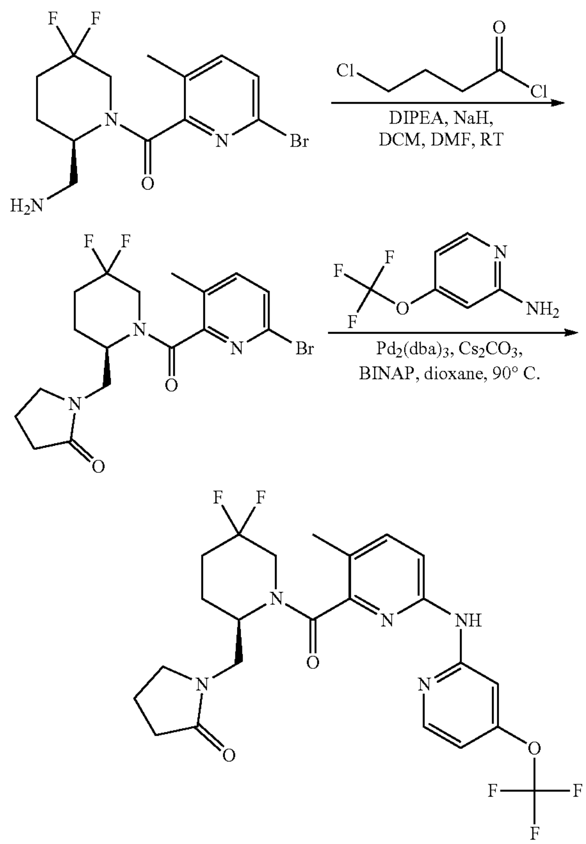

Step 1: (R)-1-(((1-(6-bromo-3-methylpyridinolinyl)-5,5-difluoropiperidin-2-yl)methyl) pyrrolidin-2-one (48-1)

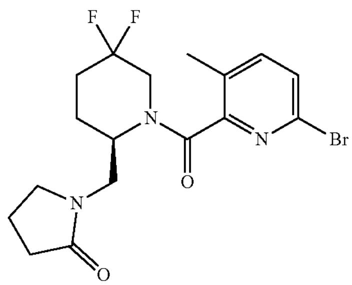 [SMILES: Cc1ccc(Br)nc1C(=O)N1CC(F)(F)CC[C@@H]1CN1CCCC1=O]

With stirring, (R)-(2-(aminomethyl)-5,5-difluoropiperidin-1-yl)(6-bromo-3-methylpyridin-2-yl) methanone (0.35 g, 1.0 mmol, 1 eq.) and DIPEA (0.39 g, 3.0 mmol, 3 eq.) were added to 5 mL of dichloromethane, 4-chlorobutyryl chloride (0.21 g, 1.5 mmol, 1.5 eq.) was added dropwise at room temperature and reacted for 2 h, and the solvent was spin-dried. 5 mL of DMF was added, and 60% sodium hydride (0.12 g, 3.0 mmol, 3.0 eq.) was added under an ice bath and reacted for 12 h at room temperature. The reaction solution was poured into ice water and extracted with ethyl acetate. The organic layer was dried over anhydrous magnesium sulfate and concentrated to dryness. The crude product was purified through column chromatography (Biotage Rening Flash 25 g, EtOAc/n-Hep=20%-50%) to obtain the title compound. LC-MS (m/z): 416.0 $[M+H]^+$.

Step 2: (R)-1-((5,5-difluoro-1-(3-methyl-6-((4-(trifluoromethoxy)pyridin-2-yl)amino)pyridine-2-carbonyl)piperidin-2-yl)methyl)pyrrolidinone-2-one (48)

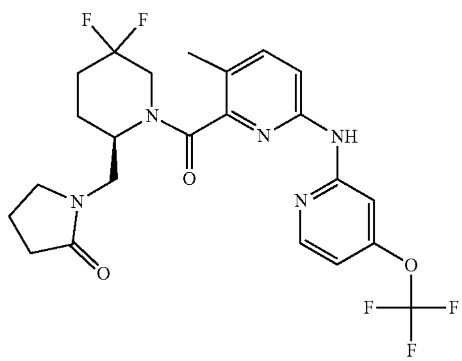 [SMILES: Cc1ccc(Nc2cc(OC(F)(F)F)ccn2)nc1C(=O)N1CC(F)(F)CC[C@@H]1CN1CCCC1=O]

(R)-1-((5,5-difluoro-1-(3-methyl-6-((4-(trifluoromethoxy)pyridin-2-yl)amino)pyridine-2-carbon yl)piperidin-2-yl)methyl)pyrrolidinone-2-one was obtained by a method similar to the synthesis method of Compound 4 in Example 1. $^1$H NMR (400 MHz, DMSO-$d_6$) δ 10.11 (d, J=4.4 Hz, 1H), 8.32 (dd, J=7.0, 5.7 Hz, 1H), 7.86 (d, J=27.2 Hz, 1H), 7.71-7.45 (m, 2H), 6.87 (d, J 9.2, Hz, 1H), 5.03 (s, 0.5H), 4.73 (t, J=13.3 Hz, 0.6H), 3.96-3.39 (m, 4H), 3.31-3.14 (m, 1H), 2.99 (td, J=8.8, 5.7 Hz, 1H), 2.90-2.79 (m, 1H), 2.40-2.00 (m, 7H), 2.01-1.59 (m, 3H). LC-MS (m/z): 514.2 $[M+H]^+$.

Example 40: N-ethyl-5,5-difluoro-1-(3-methyl-6-((4-(trifluoromethoxy)pyridin-2-yl)amino)pyridine-2-carbonyl)piperidine-2-carboxamide (49)

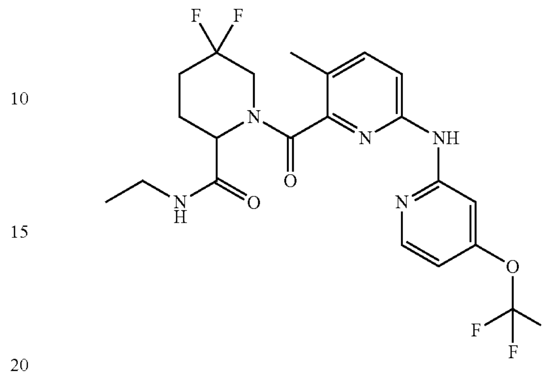

N-ethyl-5,5-difluoro-1-(3-methyl-6-((4-(trifluoromethoxy)pyridin-2-yl)amino)pyridine-2-carbonyl)piperidine-2-carboxamide was obtained by a method similar to the synthesis method of Compound 47 in Example 38. $^1$H NMR (400 MHz, DMSO-$d_6$) δ 10.19 (s, 1H), 8.32 (dd, J 5.7, 1.9 Hz, 1H), 8.24 (t, J=6.2 Hz, 0.5H), 7.84 (d, J=2.5 Hz, 1H), 7.79 (s, 0.5H), 7.68-7.62 (m, 1.5H), 7.55 (d, J=8.6 Hz, 0.5H), 6.87 (tt, J=6.2, 1.3 Hz, 1H), 5.23 (s, 0.4H), 4.71 (t, J 13.5 Hz, 0.6H), 4.23-3.59 (m, 1H), 3.51-3.37 (m, 1H), 3.23-3.08 (m, 1H), 3.05-2.89 (m, 1H), 2.34-1.99 (m, 5H), 1.98-1.80 (m, 2H), 1.07 (t, J=7.2 Hz, 1H), 0.87 (t, J=7.2 Hz, 2H). LC-MS (m/z): 488.2 $[M+H]^+$.

Example 41: N-((1S,5R)-5-acetamido-3,3-difluorocyclohexyl)-3-methyl-6-((4-4-trifluoromethoxypyridin-2-yl)amino)pyridine-2-carbonylamide (50)

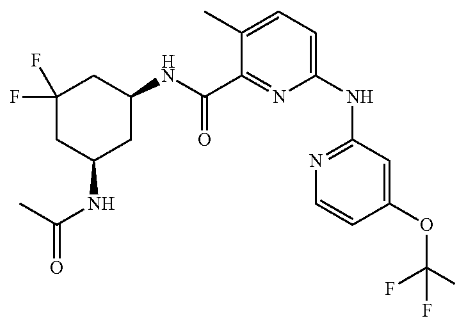

N-((1 S,5R)-5-acetamido-3,3-difluorocyclohexyl)-3-methyl-6-((4-4-trifluoromethoxypyridin-2-yl)amino)pyridine-2-carbonylamide was obtained by a method similar to the synthesis method of Compound 38 in Example 31. $^1$H NMR (400 MHz, DMSO-$d_6$) δ 10.11 (s, 1H), 8.50 (d, J 8.2 Hz, 1H), 8.33 (d, J=5.7 Hz, 1H), 8.04 (d, J=7.8 Hz, 1H), 7.91 (s, 1H), 7.70-7.50 (m, 2H), 6.88 (d, J=5.7 Hz, 1H), 4.05-4.97 (m, 1H), 3.93-3.74 (m, 1H), 2.45-2.14 (m, 5H), 2.11-1.54 (m, 7H). LC-MS (m/z): 488.4 $[M+H]^+$.

Example 42: (R)—N-((5,5-difluoro-1-(3-methyl-6-((4-(trifluoromethoxy)pyridin-2-yl)amino)pyridine-2-carbonyl)piperidin-2-yl)methyl)cyclopropanecarboxamide (51)

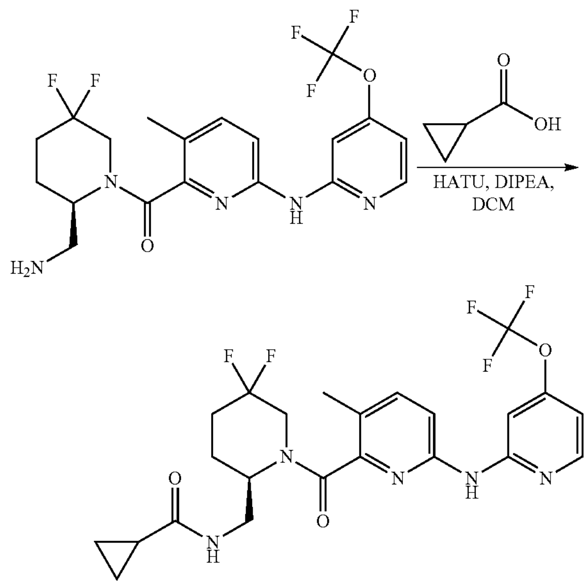

(R)—N-((5,5-difluoro-1-(3-methyl-6-((4-(trifluoromethoxy)pyridin-2-yl)amino)pyridine-2-carbonyl)piperidin-2-yl)methyl)cyclopropanecarboxamide was obtained by a method similar to the synthesis method of Compound 4 in Example 1. $^1H$ NMR (400 MHz, DMSO-$d_6$) δ 10.16 (s, 0.3H), 10.10 (s, 0.7H), 8.37 (t, J=6.2 Hz, 0.3H), 8.32 (t, J=5.3 Hz, 1H), 8.18 (t, J=6.1 Hz, 0.7H), 7.95 (s, 0.7H), 7.89 (s, 0.3H), 7.67-7.54 (m, 1.3H), 7.47 (d, J=8.5 Hz, 0.7H), 6.87 (d, J 10.0 Hz, 1H), 4.84 (s, 0.3H), 4.74 (t, J=13.4 Hz, 0.7H), 3.75-3.57 (m, 1H), 3.55-3.37 (m, 2H), 3.30-3.19 (m, 1H), 2.30-1.85 (m, 5H), 1.78-1.14 (m, 3H), 0.77-0.45 (m, 4H). LC-MS (m/z): 514.2 $[M+H]^+$.

Example 43: (R)—N-((5,5-difluoro-1-(3-methyl-6-((4-(trifluoromethoxy)pyridin-2-yl)amino)pyridine-2-carbonyl)piperidin-2-yl)methyl)-N-methylacetamide (52)

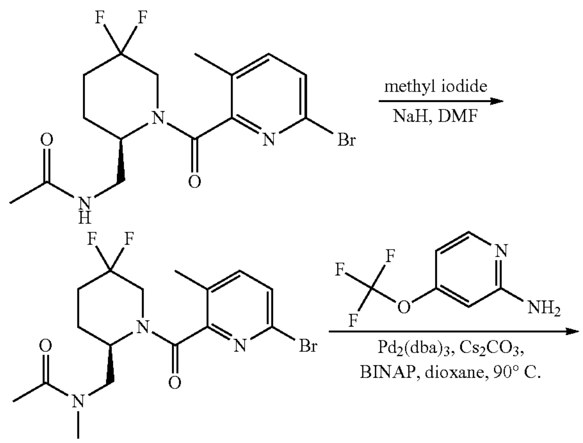

-continued

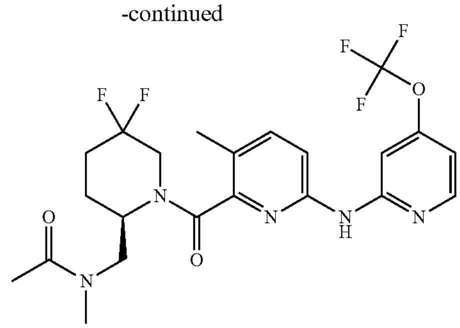

Step 1: (R)—N-((1-(6-bromo-3-methylpyridinolinyl)-5,5-difluoropiperidin-2-yl)methyl)-N-methylacetamide (52-1)

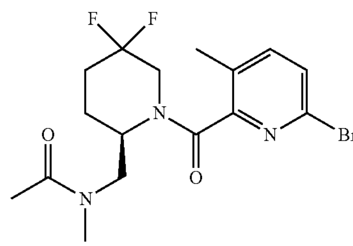

With stirring, (R)—N-((1-(6-bromo-3-methylpyridinolinyl)-5,5-difluoropiperidin-2-yl)methyl) acetamide (0.39 g, 1.0 mmol, 1 eq.) was dissolved in DMF (5 mL), 60% sodium hydride (0.12 g, 3 mmol, 3 eq.) was added at 0° C. and reacted at 0° C. for 2 h, and then iodomethane (0.28 g, 2.0 mmol, 2 eq.) was added and reacted at room temperature for 12 h. The reaction was quenched with water, the reaction solution was poured into ice water and extracted with ethyl acetate (3×30 mL), and the organic layer was dried over anhydrous magnesium sulfate and concentrated to dryness. The crude product was purified through column chromatography (Biotage Rening Flash 25 g, EtOAc/n-Hep=10%-50%) to obtain the title compound. LC-MS (m/z): 404.1 $[M+H]^+$.

Step 2: (R)—N-((5,5-difluoro-1-(3-methyl-6-((4-(trifluoromethoxy)pyridin-2-yl)amino)pyridine-2-carbonyl)piperidin-2-yl)methyl)-N-methylacetamide (52)

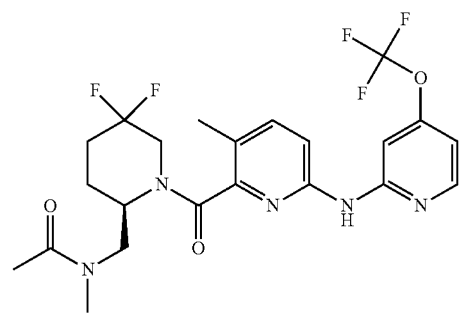 [SMILES: CC(=O)N(C)C[C@H]1CCC(F)(F)CN1C(=O)c1nc(Nc2cc(OC(F)(F)F)ccn2)ccc1C]

(R)—N-((5,5-difluoro-1-(3-methyl-6-((4-(trifluoromethoxy)pyridin-2-yl)amino)pyridine-2-carbonyl)piperidin-2-yl)methyl)-N-methylacetamide was obtained by a method similar to the synthesis method of Compound 1 in Example 1. $^1$H NMR (400 MHz, DMSO-$d_6$) δ 10.11 (d, J 6.0 Hz, 0.8H), 10.06 (s, 0.2H), 8.33 (t, J=6.2 Hz, 1H), 7.91 (s, 0.4H), 7.86 (s, 0.6H), 7.67-7.64 (m, 1H), 7.59-7.46 (m, 1H), 6.88 (t, J=7.4 Hz, 1H), 4.83-4.69 (m, 1H), 4.10-3.40 (m, 3H), 3.26 (s, 1H), 3.08 (s, 1H), 2.64 (s, 2H), 2.37-2.02 (m, 5H), 2.01-1.56 (m, 5H). LC-MS (m/z): 502.2 [M+H]$^+$.

Example 44: (R)-((1-(6-((4-ethoxypyridin-2-yl)amino)-3-methylpyridine-2-carbonyl)-5,5-difluoropiperidin-2-yl)methyl)methyl carbamate (53)

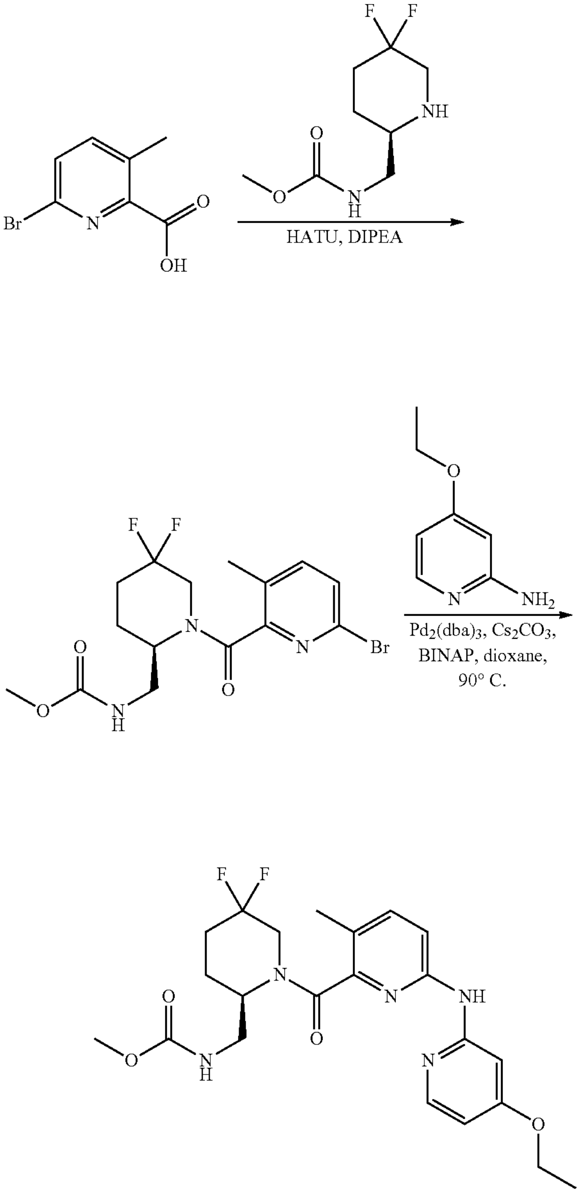

Step 1: (R)-((1-(6-bromo-3-methylpyridine-2-carbonyl)-5,5-difluoropiperidin-2-yl)methyl)methyl carbamate (54)

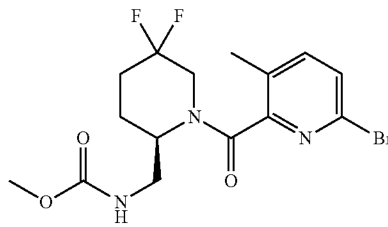

(R)-((1-(6-bromo-3-methylpyridine-2-carbonyl)-5,5-difluoropiperidin-2-yl)methyl)methyl carbamate was obtained by a method similar to the synthesis method of Compound 2 in Example 1. LC-MS (m/z): 406.1 [M+H]$^+$.

Step 2: (R)-((1-(6-((4-ethoxypyridin-2-yl)amino)-3-methylpyridine-2-carbonyl)-5,5-difluoropiperidin-2-yl)methyl)methyl carbamate (53)

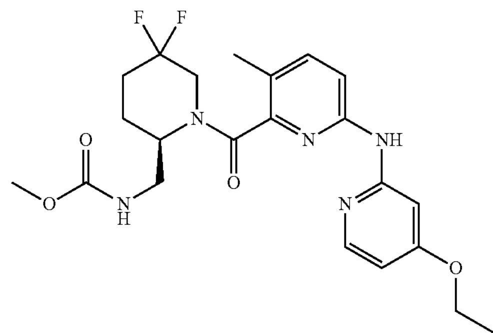 [SMILES: CCOc1ccnc(Nc2ccc(C)c(C(=O)N3CC(F)(F)CC[C@@H]3CNC(=O)OC)n2)c1]

(R)-((1-(6-((4-ethoxypyridin-2-yl)amino)-3-methylpyridine-2-carbonyl)-5,5-difluoropiperidin-2-yl)methyl)methyl carbamate was obtained by a method similar to the synthesis method of Compound 1 in Example 1. H NMR (400 MHz, DMSO-dl) δ 9.68 (s, 0.3H), 9.56 (s, 0.7H), 8.02 (dd, J=5.9, 4.0 Hz, 1H), 7.80-7.50 (m, 2H), 7.39 (dd, J=20.0, 2.4 Hz, 1H), 7.22 (t, J 6.0 Hz, 1H), 6.55-6.43 (m, 1H), 4.81 (s, 0.4H), 4.73 (t, J=13.4 Hz, 0.6H), 4.18-3.96 (m, 2H), 3.86-3.59 (m, 1H), 3.55 (s, 1H), 3.42 (s, 2H), 3.23 (t, J=20.4 Hz, 2H), 3.04 (dd, J 13.8, 6.8 Hz, 1H), 2.30-1.60 (m, 6H), 1.40-1.24 (m, 4H). LC-MS (m/z): 464.2 [M+H]$^+$.

Example 45: (R)-2-((6-(2-(acetamidomethyl)-5,5-difluoropiperidine-1-carbonyl)-5-methylpyridin-2-yl)amino)-N-methyl isonicotinamide (55)

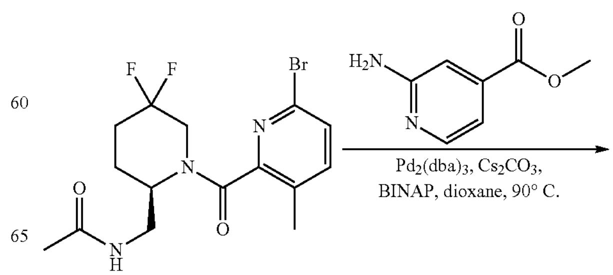

-continued

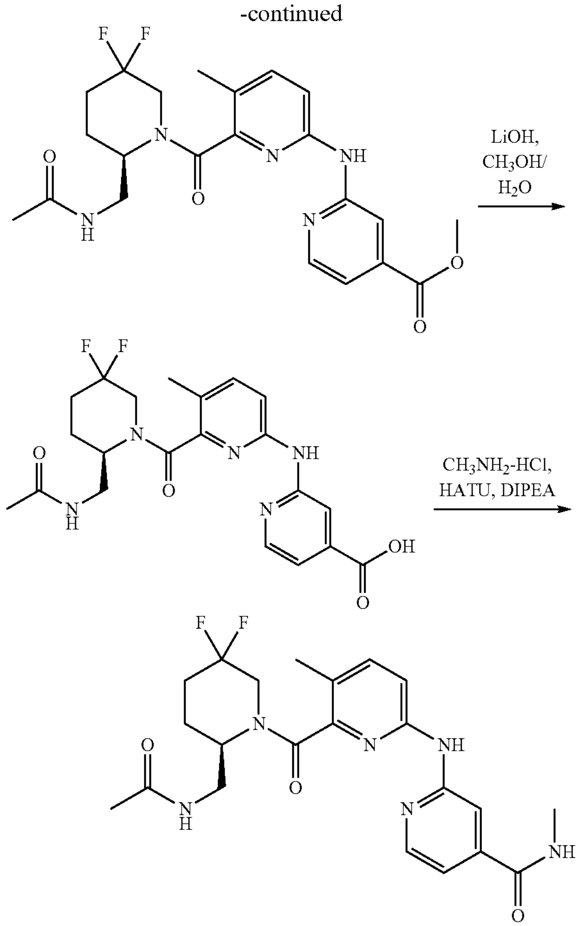

Step 1: (R)-2-((6-(2-(acetamidomethyl)-5,5-difluoropiperidine-1-carbonyl)-5-methylpyridin-2-yl)amino)methyl isonicotinate (56)

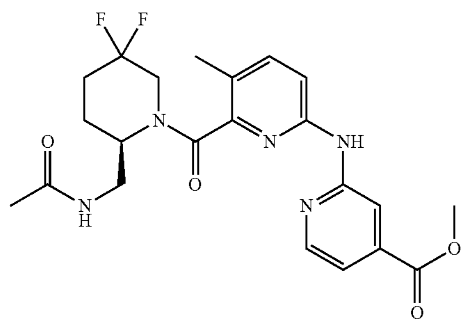 [SMILES: COC(=O)c1ccnc(Nc2ccc(C)c(C(=O)N3CC(F)(F)CC[C@@H]3CNC(C)=O)n2)c1]

(R)-2-((6-(2-(acetamidomethyl)-5,5-difluoropiperidine-1-carbonyl)-5-methylpyridin-2-yl)amino)methyl isonicotinate was obtained by a method similar to the synthesis method of Compound 1 in Example 1. $^1$H NMR (400 MHz, DMSO-$d_6$) δ 10.10 (s, 0.3H), 9.96 (s, 0.7H), 8.40 (dd, J=5.1, 0.8 Hz, 1H), 8.21 (d, J=1.2 Hz, 0.3H), 8.16-8.11 (m, 1H), 7.89 (t, J=6.1 Hz, 0.7H), 7.73 (dd, J=11.4, 8.6 Hz, 1H), 7.63 (dd, J=8.6, 3.4 Hz, 1H), 7.28 (dt, J=5.2, 1.2 Hz, 1H), 4.81 (s, 0.3H), 4.75 (t, J=13.4 Hz, 0.7H), 3.87 (s, 3H), 3.76-3.64 (m, 1H), 3.63-3.37 (m, 2H), 3.28 (s, 1H), 2.34-1.97 (m, 5H), 1.93-1.65 (m, 5H). LC-MS (m/z): 462.2 [M+H]$^+$.

Step 2: (R)-2-((6-(2-(acetamidomethyl)-5,5-difluoropiperidine-1-carbonyl)-5-methylpyridin-2-yl)amino)isonicotinic acid (57)

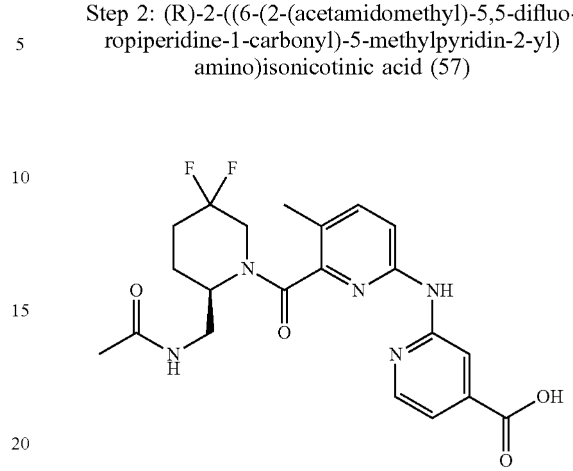

An aqueous solution of LiOH (1 M, 2 mL, 2.0 mmol) was slowly added to a solution of (R)-2-((6-(2-(acetamidomethyl)-5,5-difluoropiperidine-1-carbonyl)-5-methylpyridin-2-yl)amino)methyl isonicotinate (0.1 g, 0.2 mmol) in MeOH (10 mL) over 15 minutes. The reaction mixture was heated with stirring to room temperature overnight. The organic solvent was removed in vacuum and the residual aqueous solution was separated into layers with EA. The combined aqueous phases were acidified with 1N HCl to pH=2 and then the organic phase was extracted with water (twice). The combined organic extracts were dried over $MgSO_4$ and concentrated to obtain (R)-2-((6-(2-(acetamidomethyl)-5,5-difluoropiperidine-1-carbonyl)-5-methylpyridin-2-yl)amino)isonicotinic acid (0.06 g, 67.1%). $^1$H NMR (400 MHz, DMSO-$d_6$) δ 10.04 (s, 0.3H), 9.89 (s, 0.7H), 8.36 (dd, J=5.3, 1.6 Hz, 1H), 8.25 (s, 0.4H), 8.14 (t, J=6.1 Hz, 0.3H), 8.03 (s, 0.6H), 7.90 (t, J=6.1 Hz, 0.7H), 7.82 (d, J=8.5 Hz, 0.7H), 7.70 (d, J=8.6 Hz, 0.3H), 7.63 (dd, J=8.7, 2.4 Hz, 1H), 7.26 (td, J=4.8, 1.4 Hz, 1H), 4.82 (s, 0.4H), 4.74 (t, J 13.3 Hz, 0.6H), 3.80-3.54 (m, 1H), 3.42 (d, J=14.2 Hz, 1H), 3.32-3.17 (m, 2H), 2.70-2.53 (m, 2H), 2.36-1.90 (m, 4H), 1.87-1.65 (m, 4H). LC-MS (m/z): 448.2 [M+H]$^+$.

Step 3: (R)-2-((6-(2-(acetamidomethyl)-5,5-difluoropiperidine-1-carbonyl)-5-methylpyridin-2-yl)amino)-N-methyl isonicotinamide (55)

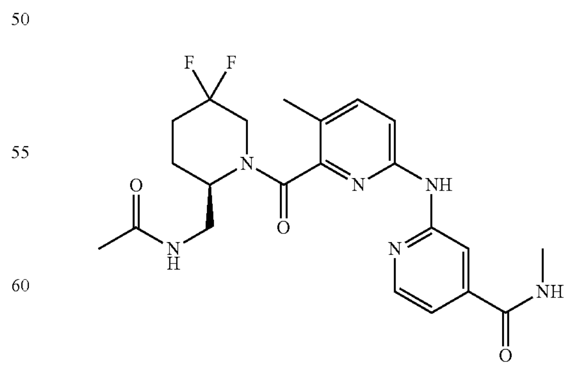

With stirring, (R)-2-((6-(2-(acetamidomethyl)-5,5-difluoropiperidine-1-carbonyl)-5-methylpyridin-2-yl)amino)isonicotinic acid (0.045 g, 0.1 mmol, 1.0 eq.) was dissolved in DCM (2 mL), and DIPEA (0.07 g, 0.5 mmol, 5 eq.) and HATU (0.06 g, 0.15 mmol, 1.5 eq.) were added at a temperature of an ice water bath. The reaction mixture was stirred at 0° C. for half an hour, and then methylamine hydrochloride (0.015 g, 0.2 mmol, 2.0 eq.) was added. The reaction mixture was stirred overnight at ambient temperature. The reaction mixture was treated with water and EtOAc, and the organic phase was isolated. The organic phase was washed with water, dried over $MgSO_4$, and concentrated to dryness. The crude product was purified through column chromatography (Biotage Rening Flash 25 g, n-Hep/EtOAc=50%-100%) to obtain the title compound (0.03 g, 65.21%). $^1$H NMR (400 MHz, DMSO-$d_6$) δ 9.97 (s, 0.4H), 9.80 (s, 0.6H), 8.60 (d, J=4.7 Hz, 0.4H), 8.54 (d, J=4.7 Hz, 0.6H), 8.31 (t, J=5.0 Hz, 1H), 8.12 (t, J=6.1 Hz, 0.4H), 8.03 (s, 0.6H), 7.89 (d, J=7.3 Hz, 1H), 7.77 (t, J=1.1 Hz, 0.7H), 7.72 (d, J=8.6 Hz, 0.3H), 7.62 (dd, J=8.6, 3.3 Hz, 1H), 7.17 (d, J=5.2, Hz, 0.3H), 7.13 (d, J=5.3, Hz, 0.7H), 4.83 (s, 0.3H), 4.72 (t, J=13.4 Hz, 0.7H), 3.86-3.54 (m, 2H), 3.45-3.41 (m, 1H), 3.31-3.19 (m, 1H), 2.77 (dd, J=4.6, 3.4 Hz, 3H), 2.27-2.05 (m, 5H), 1.97-1.58 (m, 5H). LC-MS (m/z): 461.2 [M+H]$^+$.

Example 46: (R)—N-((5,5-difluoro-1-((2-methyl-5-((4-(trifluoromethoxy)pyridin-2-yl)amino)phenyl)sulfonyl)piperidin-2-yl)methyl)acetamide (58)

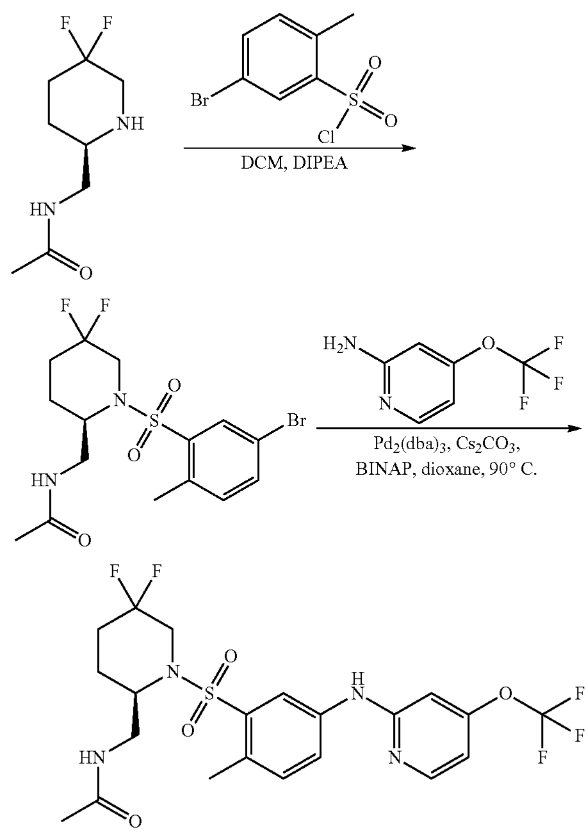

Step 1: (R)—N-((1-((5-bromo-2-methylphenyl)sulfonyl)-5,5-difluoropiperidin-2-yl)methyl) acetamide (59)

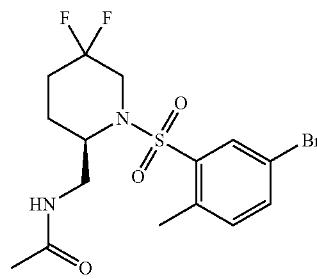 [SMILES: CC(=O)NC[C@H]1CCC(F)(F)CN1S(=O)(=O)c1cc(Br)ccc1C]

DIPEA (0.39 g, 3.0 mmol) was added to a solution of N-(5,5-difluoro-piperidin-2-ylmethyl)-acetamide (0.19 g, 1.0 mmol), and then a solution of phenylacetyl chloride (0.27 g, 1 mmol) in DCM (2 mL) was added dropwise. The reaction solution was stirred at 25° C. for 2 h, washed with 10% HCl, 10% $NaHCO_3$ and water in sequence, dried over $MgSO_4$ and filtered. The solvent was evaporated to obtain impure amide. The amide was recrystallized from ethanol to obtain (R)—N-((1-((5-bromo-2-methylphenyl)sulfonyl)-5,5-difluoropiperidin-2-yl)methyl)acetamide (0.2 g, 47.6%).

Step 2: (R)—N-((5,5-difluoro-1-((2-methyl-5-((4-(trifluoromethoxy)pyridin-2-yl)amino) phenyl)sulfonyl)piperidin-2-yl)methyl)acetamide (58)

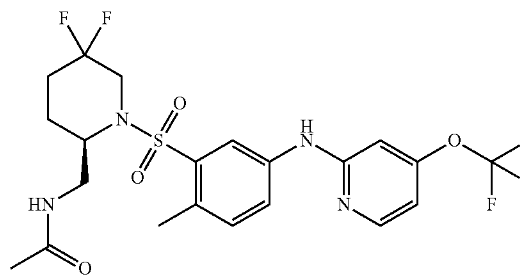

(R)—N-((5,5-difluoro-1-((2-methyl-5-((4-(trifluoromethoxy)pyridin-2-yl)amino)phenyl)sulfonyl) piperidin-2-yl)methyl)acetamide was obtained by a method similar to the synthesis method of Compound 1 in Example 1. $^1$H NMR (400 MHz, DMSO-$d_6$) δ 9.67 (s, 1H), 8.28 (d, J=5.7 Hz, 1H), 8.18 (s, 1H), 7.95 (d, J=7.8 Hz, 1H), 7.76 (s, 1H), 7.32 (d, J=8.3 Hz, 1H), 6.89-6.62 (m, 2H), 3.81 (d, J=12.2 Hz, 2H), 3.65-3.53 (m, 2H), 3.30-3.05 (m, 1H), 2.40 (s, 3H), 2.18-2.02 (m, 2H), 1.82-1.61 (m, 5H). LC-MS (m/z): 523.1 [M+H]$^+$.

Example 47: N-((1R,5S)-3,3-difluoro-5-((3-methyl-6-((4-(trifluoromethoxy)pyridin-2-yl)amino)pyridin-2-yl)amino)cyclohexyl)acetamide (60)

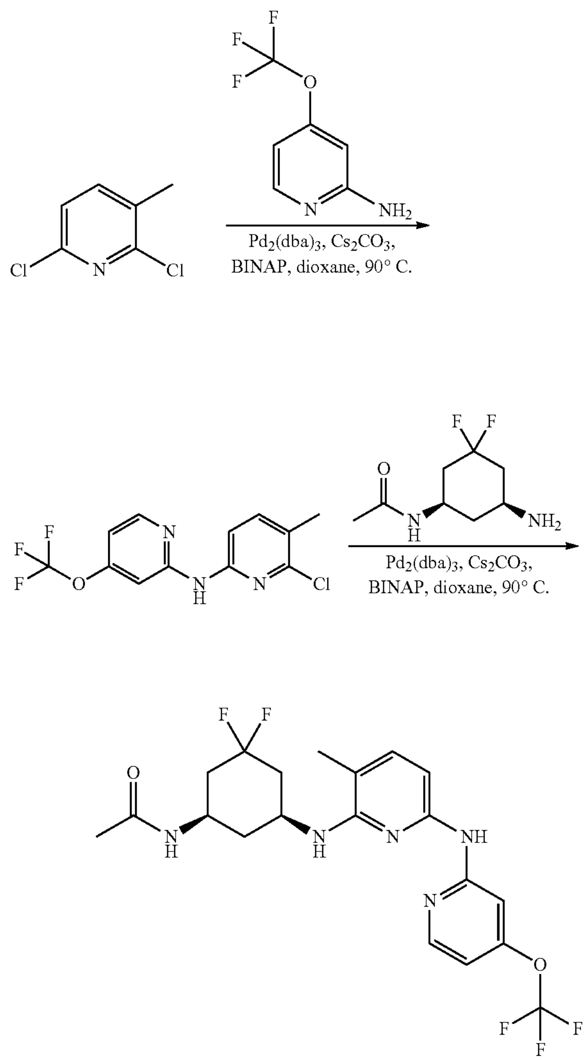

Step 1: 6-Chloro-5-methyl-N-(4-(trifluoromethoxy)pyridin-2-yl)pyridin-2-amine (61)

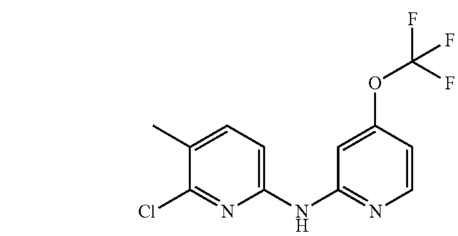 [SMILES: Cc1ccc(Nc2cc(OC(F)(F)F)ccn2)nc1Cl]

6-Chloro-5-methyl-N-(4-(trifluoromethoxy)pyridin-2-yl)pyridin-2-amine was obtained by a method similar to the synthesis method of Compound 1 in Example 1. LC-MS (m/z): 304.1 $[M+H]^+$.

Step 2: N-((1R,5S)-3,3-difluoro-5-((3-methyl-6-((4-(trifluoromethoxy)pyridin-2-yl)amino)pyridin-2-yl)amino)cyclohexyl)acetamide (60)

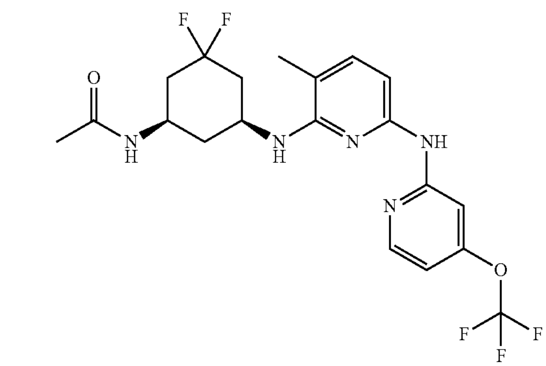 [SMILES: CC(=O)N[C@@H]1C[C@H](Nc2nc(Nc3cc(OC(F)(F)F)ccn3)ccc2C)CC(F)(F)C1]

N-((1R,5S)-3,3-difluoro-5-((3-methyl-6-((4-(trifluoromethoxy)pyridin-2-yl)amino)pyridin-2-yl)amino)cyclohexyl)acetamide was obtained by a method similar to the synthesis method of Compound 1 in Example 1. $^1H$ NMR (400 MHz, DMSO-$d_6$) δ 9.52 (s, 1H), 8.25 (d, J=5.7 Hz, 1H), 7.96 (d, J=7.5 Hz, 1H), 7.82 (d, J=2.1 Hz, 1H), 7.18 (dd, J=7.8, 0.9 Hz, 1H), 6.76 (dd, J 5.3, 2.7 Hz, 1H), 6.65 (d, J=7.8 Hz, 1H), 5.66 (d, J=8.6 Hz, 1H), 4.26 (d, J=11.4 Hz, 1H), 3.87 (s, 1H), 2.39-2.19 (m, 2H), 2.15-1.89 (s, 5H), 1.85-1.41 (m, 5H). LC-MS (m/z): 460.2$[M+H]^+$.

Example 48: (R)—N-((5,5-difluoro-1-((3-methyl-6-((4-(trifluoromethoxy)pyridin-2-yl)amino)pyridin-2-yl)methyl)piperidin-2-yl)methyl)acetamide (62)

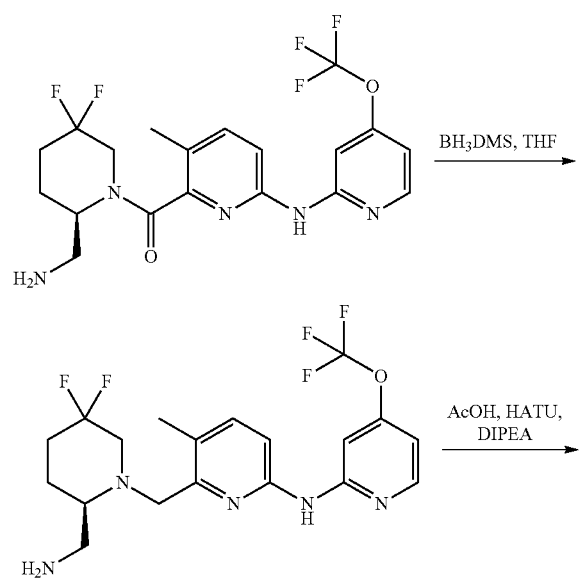

-continued

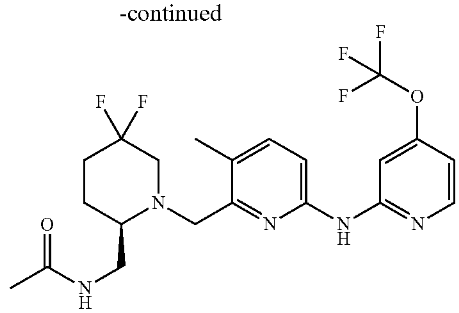

Step 1: (R)-6-((2-(aminomethyl)-5,5-difluoropiperidin-1-yl)methyl)-5-methyl-N-(4-(trifluoromethoxy)pyridin-2-yl)pyridin-2-amine (63)

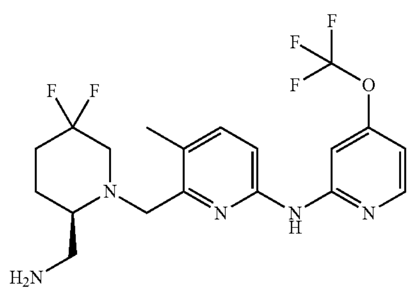 [SMILES: Cc1ccc(Nc2cc(OC(F)(F)F)ccn2)nc1CN1CC(F)(F)CC[C@@H]1CN]

$BH_3DMS$ (0.5 mL, 5.0 mmol) was added dropwise to a mixture of (R)-(2-(aminomethyl)-5,5-difluoropiperidin-1-yl)(3-methyl-6-((4-(trifluoromethoxy)pyridin-2-yl)amino)pyridin-2-yl)methanone (0.22 g, 0.5 mmol) and THE (5 mL). The mixture was stirred at 80° C. for 4 h. The mixture was quenched by adding MeOH and concentrated. The residue was purified through silica gel column chromatography (PE:EA=1:10) to obtain (R)-6-((2-(aminomethyl)-5,5-difluoropiperidin-1-yl)methyl)-5-methyl-N-(4-(trifluoromethoxy)pyridin-2-yl)pyridin-2-amine (0.1 g, with a yield of 46.5%).

Step 2: (R)—N-((5,5-difluoro-1-((3-methyl-6-((4-(trifluoromethoxy)pyridin-2-yl)amino)pyridin-2-yl)methyl)piperidin-2-yl)methyl)acetamide (62)

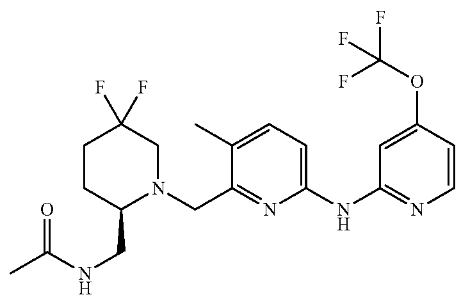 [SMILES: CC(=O)NC[C@H]1CCC(F)(F)CN1Cc1nc(Nc2cc(OC(F)(F)F)ccn2)ccc1C]

(R)—N-((5,5-difluoro-1-((3-methyl-6-((4-(trifluoromethoxy)pyridin-2-yl)amino)pyridin-2-yl)methyl)piperidin-2-yl)methyl)acetamide was obtained by a method similar to the synthesis method of Compound 4 in Example 1. $^1H$ NMR (400 MHz, DMSO-$d_6$) δ 9.99 (s, 0.4H), 9.87 (s, 0.6H), 8.30 (d, J=7.1 Hz, 1H), 8.23 (s, 1H), 8.06 (s, 0.5H), 7.56 (d, J=8.4 Hz, 0.5H), 7.43 (d, J 8.3 Hz, 1H), 7.21 (s, 1H), 6.90-6.76 (m, 1H), 5.05 (d, J=18.8 Hz, 1H), 4.05-3.95 (m, 1H), 3.46-3.30 (m, 1H), 3.08 (t, J=10.2 Hz, 1H), 2.84-2.67 (m, 3H), 2.36-2.11 (m, 5H), 2.07-1.76 (m, 4H), 1.58-1.48 (s, 1H). LC-MS (m/z): 474.4 $[M+H]^+$.

Example 49: (R)—N-((5,5-difluoro-1-(3-fluoro-6-((4-(trifluoromethoxy)pyridin-2-yl)amino)pyridine-2-carbonyl)piperidin-2-yl)methyl)acetamide (64)

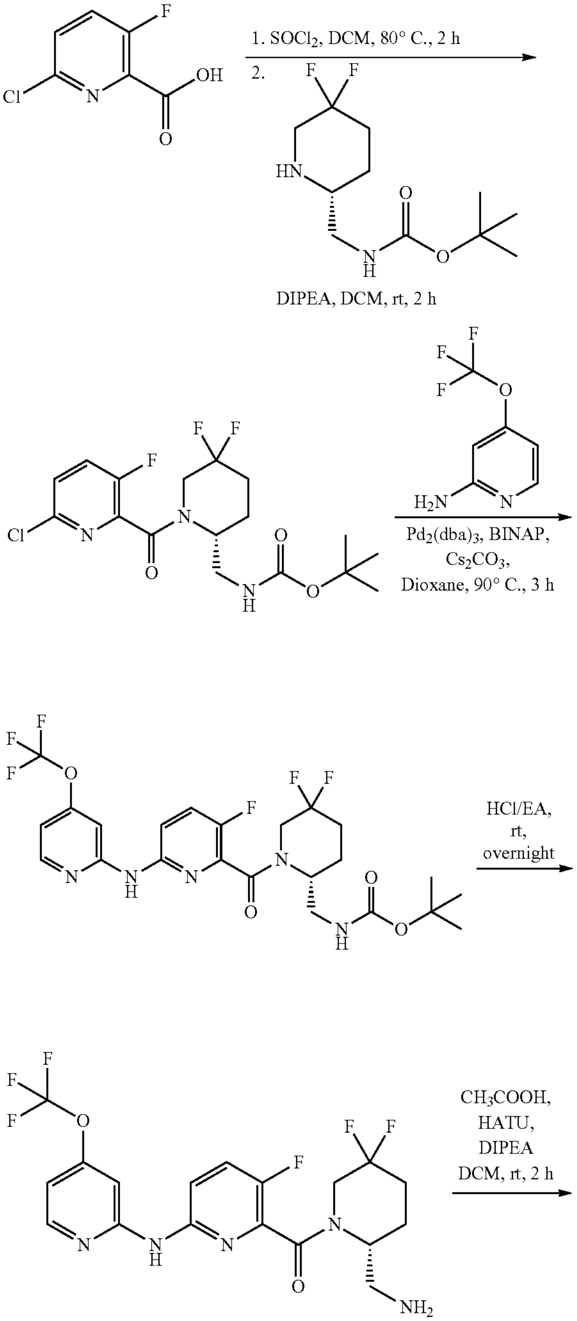

-continued

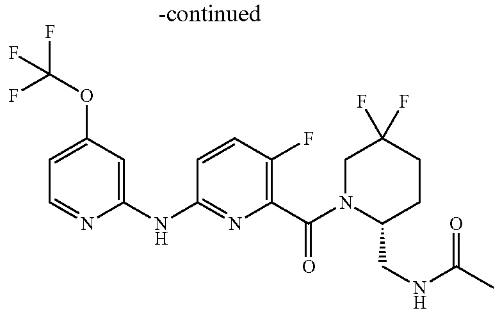

Step 1: (R)-((1-(6-chloro-3-fluoropyridine-2-carbonyl)-5,5-difluoropiperidin-2-yl)methyl) t-butyl carbamate (65)

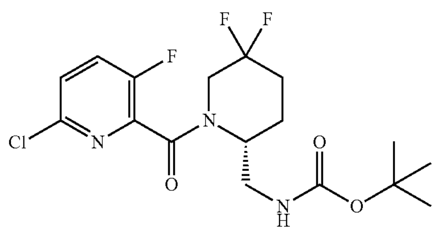 [SMILES: CC(C)(C)OC(=O)NC[C@H]1CCC(F)(F)CN1C(=O)c1nc(Cl)ccc1F]

With stirring, 6-chloro-3-fluoropicolinic acid (0.2 g, 1.14 mmol, 1.0 eq.) was dissolved in DCM (3 mL), $SOCl_2$ (677.72 mg, 5.70 mmol, 5.0 eq.) was added at room temperature, and the reaction mixture was stirred at 80° C. for 2 h. The reaction mixture was evaporated in vacuum to obtain a yellow solid. With stirring, (R)-((5,5-difluoropiperidin-2-yl)methyl)t-butyl carbamate (313.67 mg, 1.25 mmol, 1.1 eq.) and DIPEA (441.73 mg, 3.42 mmol, 3.0 eq.) were stirred into a solution and added with a solution of the previously obtained acid chloride product in DCM. The reaction mixture was stirred at room temperature for 2 h. The crude product was purified through column chromatography (Biotage Rening Flash 20 g, EtOAc/n-Hep=30%) to obtain the title compound (416 mg, with a yield of 89.5%). LC-MS (m/z): 407.8 $[M+H]^+$.

Step 2: (R)-((5,5-difluoro-1-(3-fluoro-6-((4-(trifluoromethoxy)pyridin-2-yl)amino)pyridinyl) piperidin-2-yl)methyl)t-butyl carbamate (66)

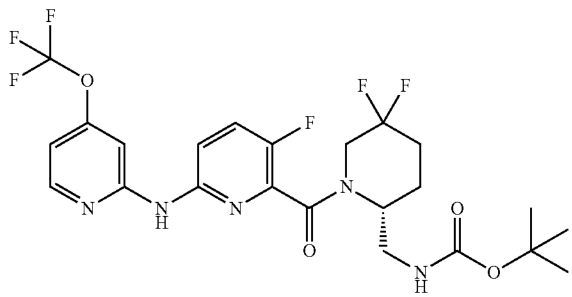 [SMILES: CC(C)(C)OC(=O)NC[C@H]1CCC(F)(F)CN1C(=O)c1nc(Nc2cc(OC(F)(F)F)ccn2)ccc1F]

A mixture of (R)-((1-(6-chloro-3-fluoropyridine-2-carbonyl)-5,5-difluoropiperidin-2-yl)methyl)t-butyl carbamate (150 mg, 367.81 μmol, 1 eq.), 4-(trifluoromethoxy)pyridin-2-amine (79.50 mg, 441.38 μmol, 1.2 eq.), $Pd_2(dba)_3$ (16.85 mg, 18.39 μmol, 0.05 eq.), BINAP (22.90 mg, 36.78 μmol, 0.1 eq.) and $Cs_2CO_3$ (239.68 mg, 735.63 μmol, 2.0 eq.) was suspended in 1,4-dioxane (3.0 mL). The resulting mixture was heated to 90° C. to react for 3 h under a nitrogen atmosphere. The reaction solution was purified through column chromatography (Biotage Rening Flash 10 g, EtOAc/n-Hep=100%, methanol/EtOAc=10%) and subjected to reverse phase column chromatography (MeCN/water=40%) to obtain the title compound (95 mg, 47.0%). $^1$H NMR (400 MHz, Chloroform-d) δ 8.65 (d, J=9.3 Hz, 0.3H), 8.29-8.24 (m, 1H), 8.02 (dd, J=9.0, 3.3 Hz, 0.4H), 7.86-7.66 (m, 1H), 7.60-7.42 (m, 1H), 7.18-6.61 (m, 2H), 5.38 (t, J=5.2, 0.6H), 5.13-4.97 (m, 1H), 4.89 (d, J=6.5 Hz, 0.4H), 4.00 (s, 1H), 3.80-2.99 (m, 4H), 2.28-1.70 (m, 4H), 1.65-1.43 (m, 9H). LC-MS (m/z): 549.5 $[M+H]^+$.

Step 3: (R)-(2-(aminomethyl)-5,5-difluoropiperidin-1-yl)(3-fluoro-6-((4-(trifluoromethoxy)pyridin-2-yl)amino)pyridin-2-yl)methanone (67)

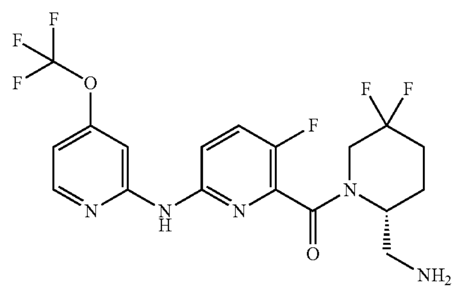 [SMILES: NC[C@H]1CCC(F)(F)CN1C(=O)c1nc(Nc2cc(OC(F)(F)F)ccn2)ccc1F]

With stirring, (R)-((5,5-difluoro-1-(3-fluoro-6-((4-(trifluoromethoxy)pyridin-2-yl)amino)pyridinyl)piperidin-2-yl)methyl)t-butyl carbamate (80 mg, 145.60 μmol, 1 eq.) was dissolved in DCM (3 mL), and a solution of HCl in EA (4 M, 3.64 mL, 100 eq.) was added at a temperature of an ice water bath. The reaction mixture was stirred overnight at room temperature. The mixture was neutralized with a saturated aqueous solution of $NaHCO_3$ and extracted with DCM. The solvent was removed by being evaporated in vacuum to obtain the title compound (50 mg, with a yield of 76.4%). $^1$H NMR (400 MHz, Chloroform-d) δ 8.30-8.22 (m, 1H), 8.13-7.87 (m, 1H), 7.70 (td, J=8.8, 8.3, 3.6 Hz, 1H), 7.53-7.38 (m, 2H), 6.75 (s, 0.5H), 6.74 (s, 0.5H), 5.07-4.97 (m, 1H), 3.79-3.66 (m, 1H), 3.51-2.65 (m, 4H), 2.26-1.77 (m, 5H). LC-MS (m/z): 449.4 $[M+H]^+$.

Step 4: (R)—N-((5,5-difluoro-1-(3-fluoro-6-((4-(trifluoromethoxy)pyridin-2-yl)amino)pyridine-2-carbonyl)piperidin-2-yl)methyl)acetamide (64)

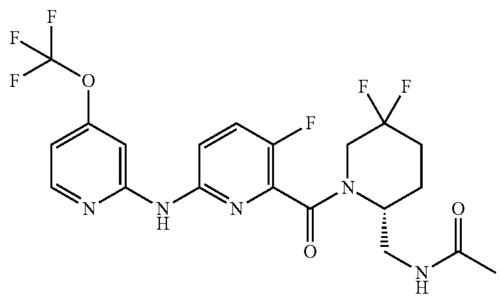 [SMILES: CC(=O)NC[C@H]1CCC(F)(F)CN1C(=O)c1nc(Nc2cc(OC(F)(F)F)ccn2)ccc1F]

With stirring, $CH_3COOH$ (3.01 mg, 50.07 μmol, 1.5 eq.), HATU (19.04 mg, 50.07 μmol, 1.5 eq.) and DIPEA (12.94 mg, 100.14 μmol, 3.0 eq.) were dissolved in DCM (3 mL), and a solution of (R)-(2-(aminomethyl)-5,5-difluoropiperidin-1-yl)(3-fluoro-6-((4-(trifluoromethoxy)pyridin-2-yl)amino)pyridin-2-yl)methanone (15 mg, 33.38 μmol, 1.0 eq.) in DCM (2 mL) was added dropwise at room temperature. The reaction mixture was stirred for 2 h at room temperature. The mixture was washed with brine and extracted with DCM. The crude product was purified through reverse phase column chromatography (MeCN/water=30%) to obtain the title compound (10.5 mg, 64.0%). $^1$H NMR (400 MHz, DMSO-$d_6$) δ 10.32 (s, 0.2H), 10.29 (s, 0.8H), 8.36-8.33 (m, 1H), 8.09 (t, J=6.2 Hz, 0.2H), 7.93 (t, J=6.1 Hz, 0.8H), 7.83-7.75 (m, 2H), 7.70 (d, J=3.5 Hz, 0.5H), 7.68 (d, J=3.5 Hz, 0.2H), 6.93-6.89 (m, 1H), 4.83-4.75 (m, 0.3H), 4.70-4.60 (m, 1H), 3.87-3.37 (m, 3H), 3.10 (dt, J=13.8, 5.7 Hz, 1H), 2.35-1.82 (m, 4H), 1.74-1.67 (m, 3H). LC-MS (m/z): 491.4 $[M+H]^+$.

Example 50: (R)—N-((5,5-difluoro-1-(2-methyl-5-((4-(trifluoromethoxy)pyridin-2-yl)amino)benzoyl)piperidin-2-yl)methyl)acetamide (68)

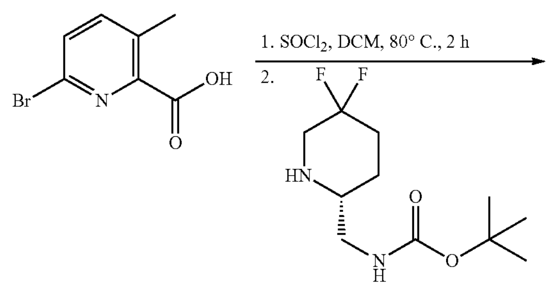

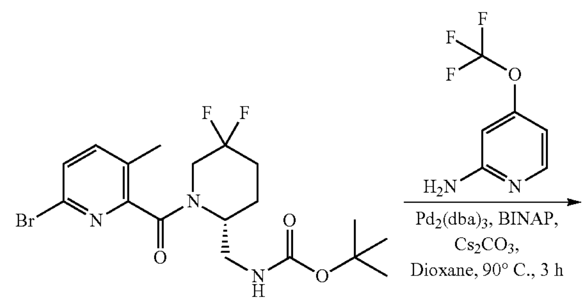

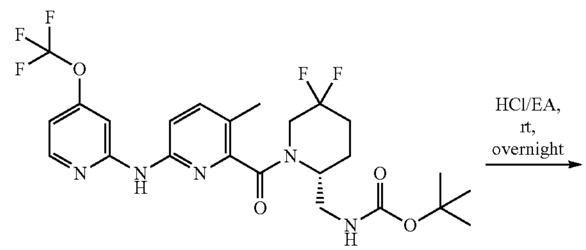

-continued

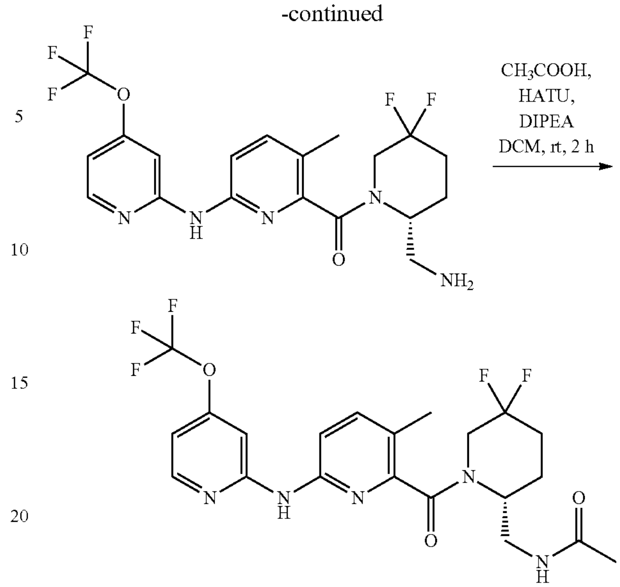

Step 1: (R)-((1-(5-bromo-2-methylbenzoyl)-5,5-difluoropiperidin-2-yl)methyl)t-butyl carbamate (69)

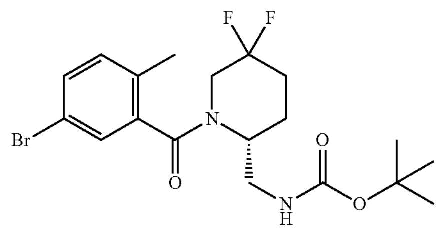 [SMILES: Cc1ccc(Br)cc1C(=O)N1CC(F)(F)CC[C@@H]1CNC(=O)OC(C)(C)C]

(R)-((1-(5-bromo-2-methylbenzoyl)-5,5-difluoropiperidin-2-yl)methyl)t-butyl carbamate was obtained by a method similar to the synthesis method of Compound 65 in Example 49. LC-MS (m/z): 446.3 $[M+H]^+$.

Step 2: (R)-((5,5-difluoro-1-(2-methyl-5-((4-(trifluoromethoxy)pyridin-2-yl)amino)benzoyl) piperidin-2-yl)methyl)t-butyl carbamate (70)

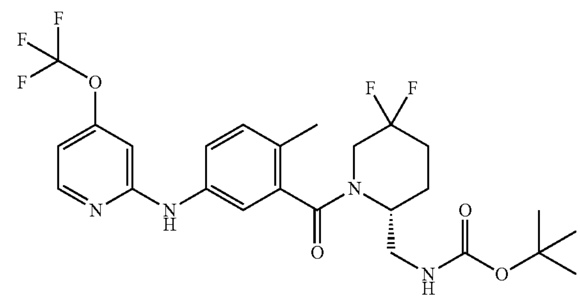 [SMILES: Cc1ccc(Nc2cc(OC(F)(F)F)ccn2)cc1C(=O)N1CC(F)(F)CC[C@@H]1CNC(=O)OC(C)(C)C]

(R)-((5,5-difluoro-1-(2-methyl-5-((4-(trifluoromethoxy)pyridin-2-yl)amino)benzoyl)piperidin-2-yl)methyl)t-butyl carbamate was obtained by a method similar to the synthesis method of Compound 66 in Example 49. $^1$H NMR (400

MHz, Chloroform-d) δ 8.22-8.09 (m, 1H), 7.52-7.31 (m, 1H), 7.25-6.94 (m, 2H), 6.72-6.44 (m, 3H), 5.94-4.91 (m, 2H), 3.91-3.35 (m, 4H), 3.24-2.90 (m, 2H), 2.36-2.24 (m, 3H), 2.20-1.78 (m, 4H), 1.49-1.26 (m, 9H). LC-MS (m/z): 544.5 $[M+H]^+$.

Step 3: (R)-(2-(aminomethyl)-5,5-difluoropiperidin-1-yl)(2-methyl-5-((4-(trifluoromethoxy)pyridin-2-yl)amino)phenyl)methanone (71)

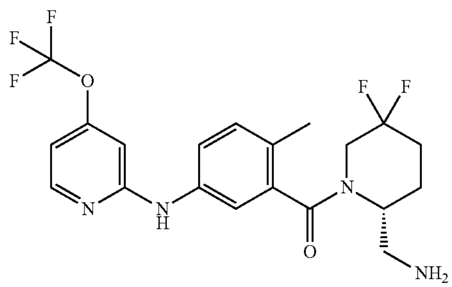

(R)-(2-(aminomethyl)-5,5-difluoropiperidin-1-yl)(2-methyl-5-((4-(trifluoromethoxy)pyridin-2-yl)amino)phenyl)methanone was obtained by a method similar to the synthesis method of Compound 67 in Example 49. LC-MS (m/z): 444.4 $[M+H]^+$.

Step 4: (R)—N-((5,5-difluoro-1-(2-methyl-5-((4-(trifluoromethoxy)pyridin-2-yl)amino)benzoyl) piperidin-2-yl)methyl)acetamide (68)

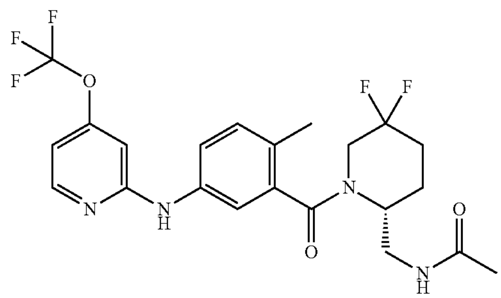 [SMILES: CC(=O)NC[C@H]1CCC(F)(F)CN1C(=O)c1cc(Nc2cc(OC(F)(F)F)ccn2)ccc1C]

(R)—N-((5,5-difluoro-1-(2-methyl-5-((4-(trifluoromethoxy)pyridin-2-yl)amino)benzoyl)piperidin-2-yl)methyl)acetamide was obtained by a method similar to the synthesis method of Compound 64 in Example 49. $^1$H NMR (400 MHz, Chloroform-d) δ 8.21 (s, 0.8H), 8.10 (s, 0.2H), 7.36 (d, J=8.4 Hz, 1H), 7.25-7.18 (m, 1H), 7.14-6.66 (m, 2H), 6.66-6.44 (m, 2H), 6.17 (d, J=42.9 Hz, 1H), 5.42-5.37 (m, 0.2H), 5.10-5.01 (m, 0.8H), 4.25-4.06 (m, 1H), 3.99-2.95 (m, 4H), 2.40-1.62 (m, 10H). LC-MS (m/z): 486.4 $[M+H]^+$.

Example 51: (R)—N-((5,5-difluoro-1-(5-methyl-2-((4-(trifluoromethoxy)pyridin-2-yl)amino) isonicotinoyl)piperidin-2-yl)methyl)acetamide (72)

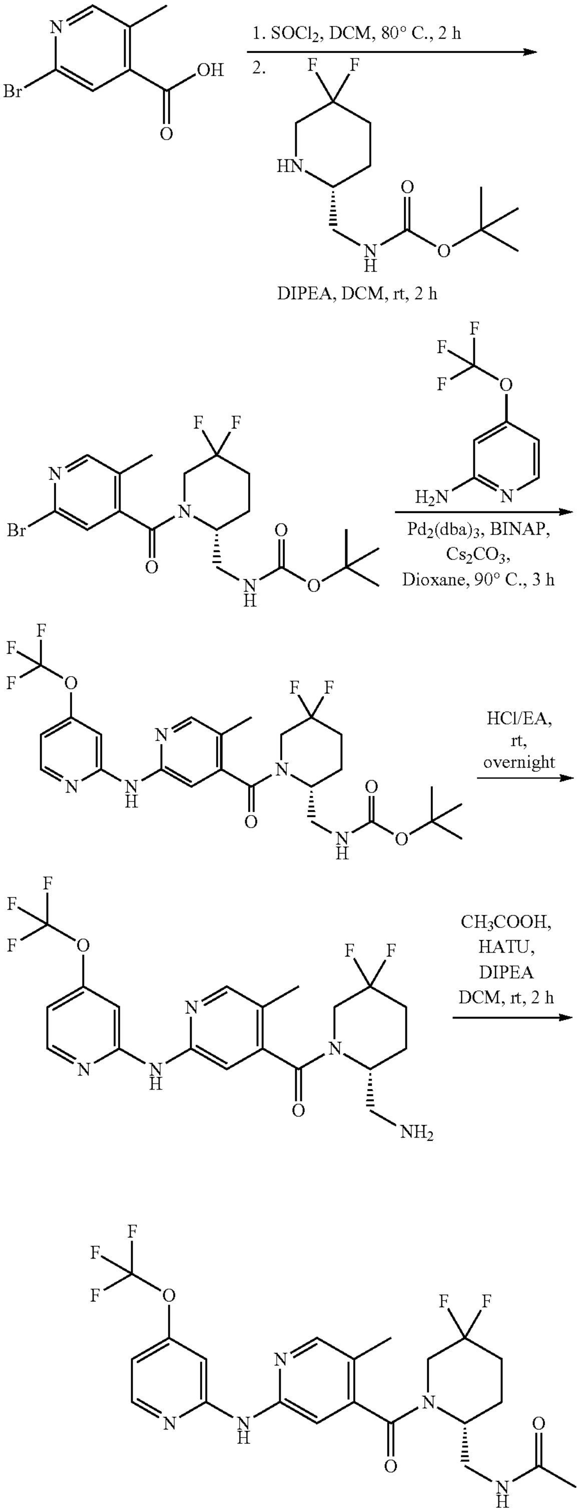

Step 1: (R)-((1-(2-bromo-5-methylisonicotinoyl)-5,5-difluoropiperidin-2-yl)methyl)t-butyl carbamate (73)

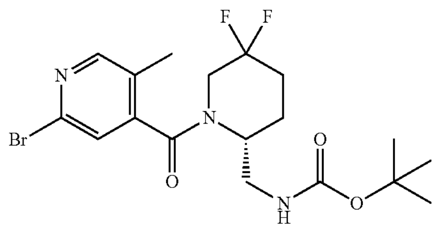 [SMILES: Cc1cnc(Br)cc1C(=O)N1CC(F)(F)CC[C@@H]1CNC(=O)OC(C)(C)C]

(R)-((1-(2-bromo-5-methylisonicotinoyl)-5,5-difluoropiperidin-2-yl)methyl)t-butyl carbamate was obtained by a method similar to the synthesis method of Compound 65 in Example 49. LC-MS (m/z): 448.3 $[M+H]^+$.

Step 2: (R)-((5,5-difluoro-1-(5-methyl-2-((4-(trifluoromethoxy)pyridin-2-yl)amino) isonicotinoyl)piperidin-2-yl)methyl)t-butyl carbamate (74)

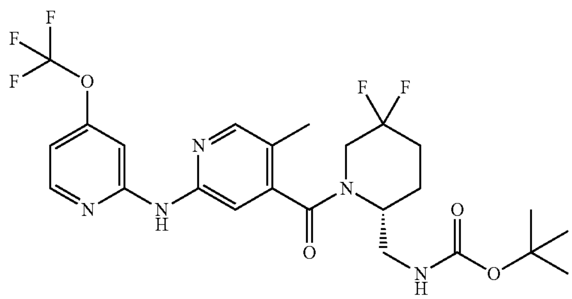 [SMILES: Cc1cnc(Nc2cc(OC(F)(F)F)ccn2)cc1C(=O)N1CC(F)(F)CC[C@@H]1CNC(=O)OC(C)(C)C]

(R)-((5,5-difluoro-1-(5-methyl-2-((4-(trifluoromethoxy) pyridin-2-yl)amino)isonicotinoyl) piperidin-2-yl)methyl)t-butyl carbamate was obtained by a method similar to the synthesis method of Compound 66 in Example 49. $^1$H NMR (400 MHz, DMSO-$d_6$) δ 10.06 (t, J=24.7 Hz, 1H), 8.33-8.16 (m, 2H), 7.86-7.43 (m, 2H), 7.12-6.81 (m, 2H), 4.77 (d, J=67.8 Hz, 1H), 3.75-3.39 (m, 2H), 3.24-2.93 (m, 2H), 2.32-1.64 (m, 7H), 1.49-1.11 (m, 9H). LC-MS (m/z): 545.5 $[M+H]^+$.

Step 3: (R)-(2-(aminomethyl)-5,5-difluoropiperidin-1-yl)(5-methyl-2-((4-(trifluoromethoxy)pyridin-2-yl) amino)pyridin-4-yl)methanone (75)

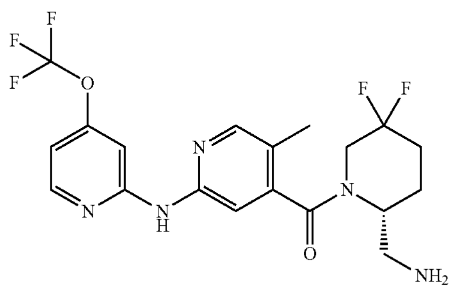 [SMILES: Cc1cnc(Nc2cc(OC(F)(F)F)ccn2)cc1C(=O)N1CC(F)(F)CC[C@@H]1CN]

(R)-(2-(aminomethyl)-5,5-difluoropiperidin-1-yl)(5-methyl-2-((4-(trifluoromethoxy)pyridin-2-yl)amino)pyridin-4-yl)methanone was obtained by a method similar to the synthesis method of Compound 67 in Example 49. LC-MS (m/z): 445.4 $[M+H]^+$.

Step 4: (R)—N-((5,5-difluoro-1-(5-methyl-2-((4-(trifluoromethoxy)pyridin-2-yl)amino) isonicotinoyl) piperidin-2-yl)methyl)acetamide (72)

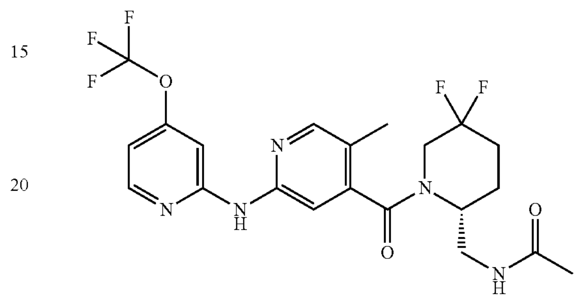

(R)—N-((5,5-difluoro-1-(5-methyl-2-((4-(trifluoromethoxy)pyridin-2-yl)amino)isonicotinoyl)piperidin-2-yl)methyl)acetamide was obtained by a method similar to the synthesis method of Compound 64 in Example 49. $^1$H NMR (400 MHz, DMSO-$d_6$) δ 10.12 (s, 0.4H), 10.07 (s, 0.6H), 8.30 (dd, J=5.7, 1.5 Hz, 1H), 8.23-7.91 (m, 2H), 7.83-7.43 (m, 2H), 6.88-6.85 (m, 1H), 4.78 (dt, J=50.4, 9.7 Hz, 1H), 3.83-3.38 (m, 3H), 3.28-3.10 (m, 1H), 2.36-1.80 (m, 7H), 1.73 (s, 3H). LC-MS (m/z): 487.4 $[M+H]^+$.

Example 52: (R)—N-((5,5-difluoro-1-(5-methyl-2-((4-(trifluoromethoxy)pyridin-2-yl)amino)pyrimidine-4-carbonyl)piperidin-2-yl)methyl)acetamide (76)

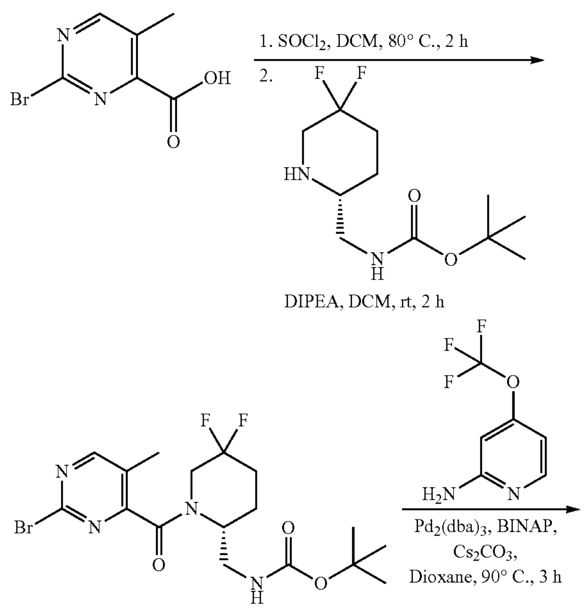

-continued

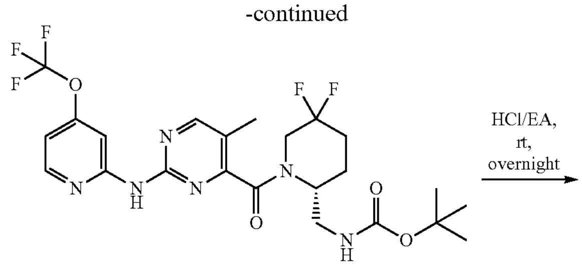

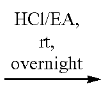

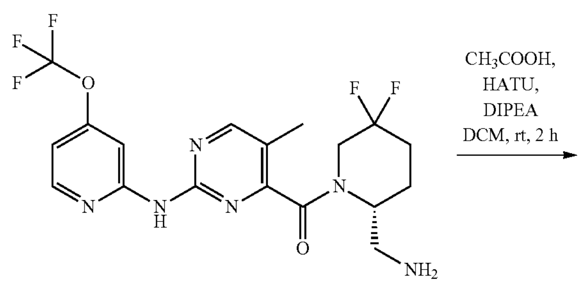

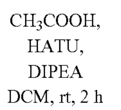

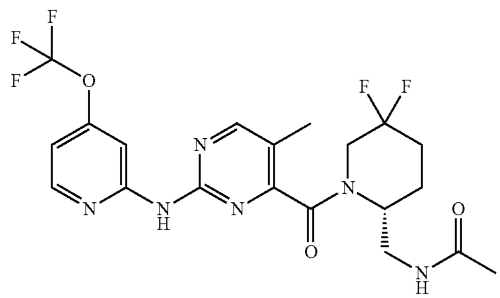

Step 1: (R)-((1-(2-chloro-5-methylpyrimidine-4-carbonyl)-5,5-difluoropiperidin-2-yl)methyl) t-butyl carbamate (77)

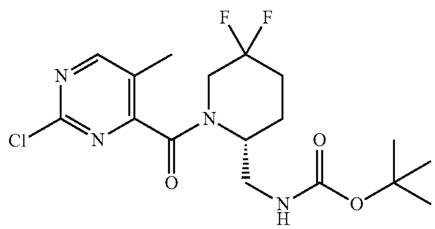 [SMILES: Cc1cnc(Cl)nc1C(=O)N1CC(F)(F)CC[C@@H]1CNC(=O)OC(C)(C)C]

(R)-((1-(2-chloro-5-methylpyrimidine-4-carbonyl)-5,5-difluoropiperidin-2-yl)methyl)t-butyl carbamate was obtained by a method similar to the synthesis method of Compound 65 in Example 49. LC-MS (m/z): 404.8 $[M+H]^+$.

Step 2: (R)-((5,5-difluoro-1-(5-methyl-2-((4-(trifluoromethoxy)pyridin-2-yl)amino)pyrimidine-4-carbonyl)piperidin-2-yl)methyl)t-butyl carbamate (78)

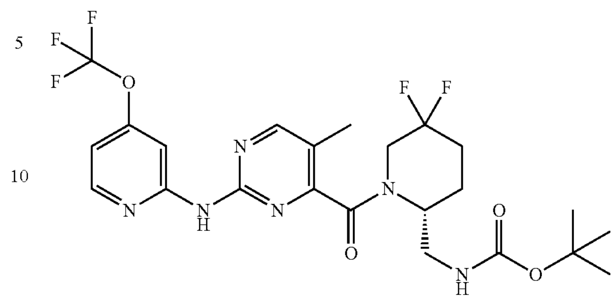

(R)-((5,5-difluoro-1-(2-methyl-5-((4-(trifluoromethoxy)pyridin-2-yl)amino)benzoyl)piperidin-2-yl)methyl)t-butyl carbamate was obtained by a method similar to the synthesis method of Compound 66 in Example 49. $^1H$ NMR (400 MHz, Chloroform-d) δ 8.50 (d, J=9.7 Hz, 1H), 8.37-8.29 (m, 2H), 8.18 (d, J=11.4 Hz, 1H), 6.81 (dd, J=11.1, 5.6 Hz, 1H), 5.81 (s, 0.5H), 5.06-4.96 (m, 1H), 4.91 (t, J=4, 0.5H), 3.75 (s, 1H), 3.67-3.16 (m, 4H), 2.25 (d, J=17.6 Hz, 3H), 2.18-1.73 (m, 4H), 1.49 (d, J=3.4 Hz, 9H). LC-MS (m/z): 546.5 $[M+H]^+$.

Step 3: (R)-(2-(aminomethyl)-5,5-difluoropiperidin-1-yl)(5-methyl-2-((4-(trifluoromethoxy)pyridin-2-yl)amino)pyrimidin-4-yl)methanone (79)

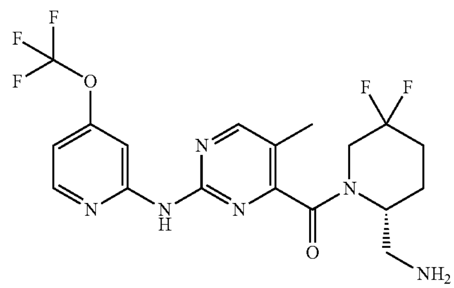 [SMILES: Cc1cnc(Nc2cc(OC(F)(F)F)ccn2)nc1C(=O)N1CC(F)(F)CC[C@@H]1CN]

(R)-(2-(aminomethyl)-5,5-difluoropiperidin-1-yl)(5-methyl-2-((4-(trifluoromethoxy)pyridin-2-yl)amino)pyrimidin-4-yl)methanone was obtained by a method similar to the synthesis method of Compound 67 in Example 49. LC-MS (m/z): 446.4 $[M+H]^+$.

Step 4: (R)—N-((5,5-difluoro-1-(5-methyl-2-((4-(trifluoromethoxy)pyridin-2-yl)amino)pyrimidine-4-carbonyl)piperidin-2-yl)methyl)acetamide (76)

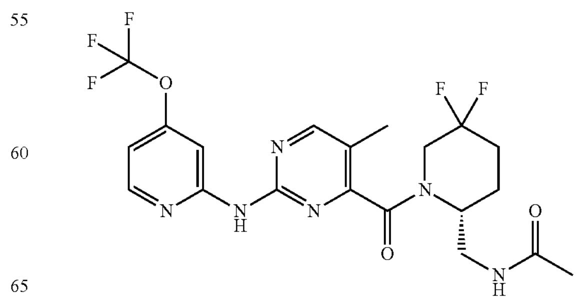

(R)—N-((5,5-difluoro-1-(5-methyl-2-((4-(trifluoromethoxy)pyridin-2-yl)amino)pyrimidine-4-carbonyl)piperidin-2-yl)methyl)acetamide was obtained by a method similar to the synthesis method of Compound 64 in Example 49. $^1$H NMR (400 MHz, DMSO-$d_6$) δ 10.43 (s, 0.8H), 10.40 (s, 0.2H), 8.61 (s, 0.8H), 8.58 (s, 0.2H), 8.40-8.36 (m, 1H), 8.26 (s, 0.3H), 8.25-8.22 (m, 0.7H), 8.13 (t, J=6.2 Hz, 0.3H), 7.93 (t, J=6.1 Hz, 0.7H), 7.01-6.96 (m, 1H), 4.83-4.75 (m, 0.4H), 4.67 (t, J=13.2 Hz, 0.6H), 3.76-3.37 (m, 4H), 3.25-3.18 (m, 1H), 2.35-1.79 (m, 7H). LC-MS (m/z): 488.4 $[M+H]^+$.

Example 53: (R)—N-((5,5-difluoro-1-(6-((4-(trifluoromethoxy)pyridin-2-yl)amino)pyridine-2-carbonyl)piperidin-2-yl)methyl)acetamide (80)

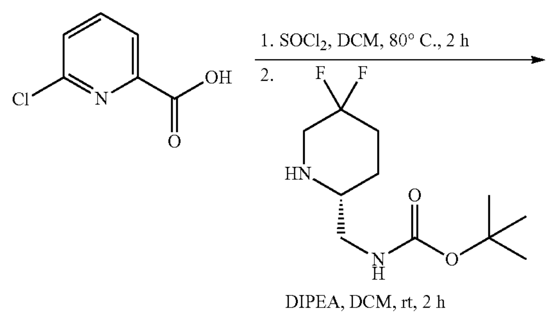

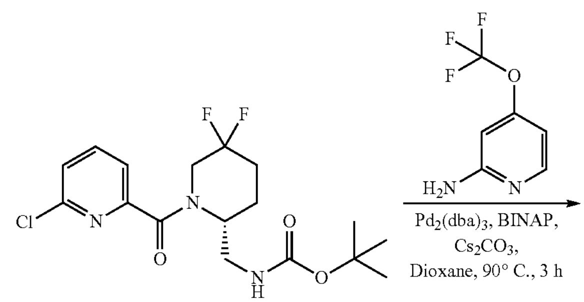

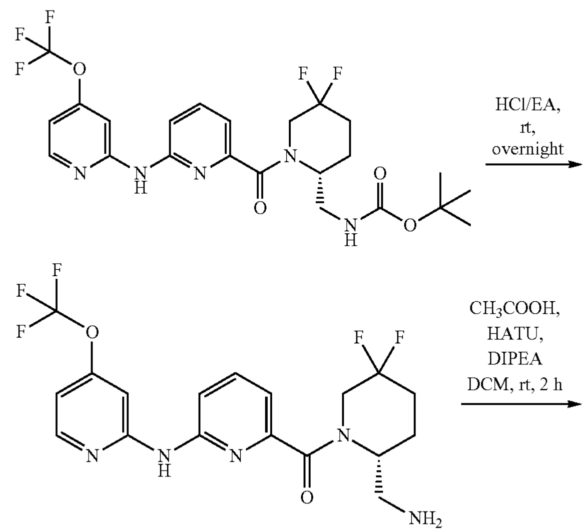

-continued

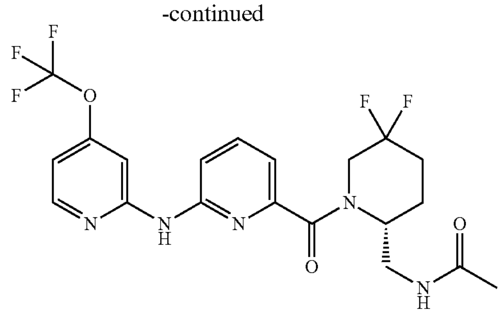

Step 1: (R)-((1-(6-chloropyridine-2-carbonyl)-5,5-difluoropiperidin-2-yl)methyl)t-butyl carbamate (81)

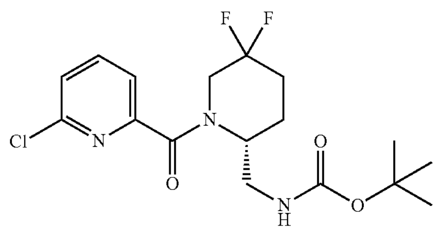 [SMILES: CC(C)(C)OC(=O)NC[C@H]1CCC(F)(F)CN1C(=O)c1cccc(Cl)n1]

(R)-((1-(6-chloropyridine-2-carbonyl)-5,5-difluoropiperidin-2-yl)methyl)t-butyl carbamate was obtained by a method similar to the synthesis method of Compound 65 in Example 49. LC-MS (m/z): 389.8 $[M+H]^+$.

Step 2: (R)-((5,5-difluoro-1-(6-((4-(trifluoromethoxy)pyridin-2-yl)amino)pyridine-2-carbonyl)piperidin-2-yl)methyl)t-butyl carbamate (82)

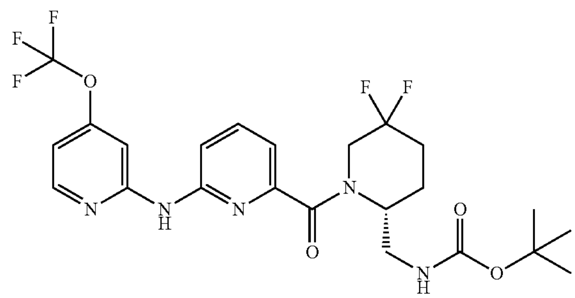 [SMILES: CC(C)(C)OC(=O)NC[C@H]1CCC(F)(F)CN1C(=O)c1cccc(Nc2cc(OC(F)(F)F)ccn2)n1]

(R)-((5,5-difluoro-1-(6-((4-(trifluoromethoxy)pyridin-2-yl)amino)pyridine-2-carbonyl)piperidin-2-yl)methyl)t-butyl carbamate was obtained by a method similar to the synthesis method of Compound 66 in Example 49. LC-MS (m/z): 531.5 $[M+H]^+$.

Step 3: (R)-(2-(aminomethyl)-5,5-difluoropiperidin-1-yl)(6-((4-(trifluoromethoxy)pyridin-2-yl)amino)pyridin-2-yl)methanone (83)

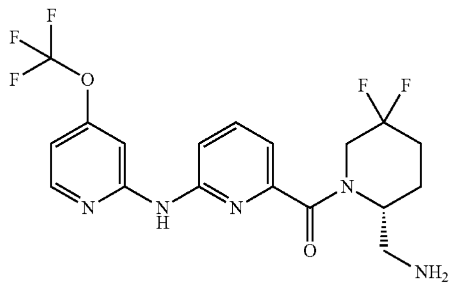 [SMILES: NC[C@H]1CCC(F)(F)CN1C(=O)c1cccc(Nc2cc(OC(F)(F)F)ccn2)n1]

(R)-(2-(aminomethyl)-5,5-difluoropiperidin-1-yl)(6-((4-(trifluoromethoxy)pyridin-2-yl)amino)pyridin-2-yl)methanone was obtained by a method similar to the synthesis method of Compound 67 in Example 49. LC-MS (m/z): 431.4 [M+H]+.

Step 4: (R)—N-((5,5-difluoro-1-(6-((4-(trifluoromethoxy)pyridin-2-yl)amino)pyridine-2-carbonyl)piperidin-2-yl)methyl)acetamide (80)

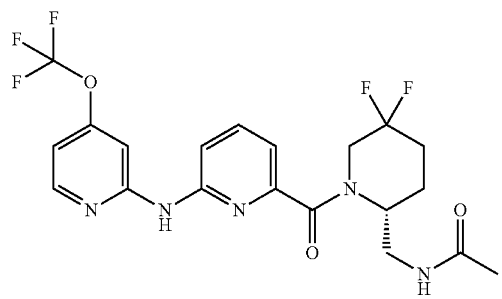 [SMILES: CC(=O)NC[C@H]1CCC(F)(F)CN1C(=O)c1cccc(Nc2cc(OC(F)(F)F)ccn2)n1]

(R)—N-((5,5-difluoro-1-(6-((4-(trifluoromethoxy)pyridin-2-yl)amino)pyridine-2-carbonyl) piperidin-2-yl)methyl) acetamide was obtained by a method similar to the synthesis method of Compound 64 in Example 49. $^1$H NMR (400 MHz, DMSO-$d_6$) δ 10.27 (s, 0.2H), 10.23 (s, 0.8H), 8.36 (d, J=5.7 Hz, 1H), 8.15-7.78 (m, 3H), 7.68 (d, J=8.5 Hz, 0.3H), 7.59 (d, J=8.4 Hz, 0.7H), 7.02-6.89 (m, 2H), 4.77 (s, 0.3H), 4.62 (t, J=13.3 Hz, 0.7H), 4.10 (s, 1H), 3.77-3.36 (m, 3H), 3.14 (dt, J=13.1, 5.9 Hz, 1H), 2.33-1.83 (m, 4H), 1.74-1.69 (m, 3H). LC-MS (m/z): 473.4 [M+H]+.

Example 54: (R)—N-((1-(3-chloro-6-((4-(trifluoromethoxy)pyridin-2-yl)amino)pyridine-2-carbonyl)-5,5-difluoropiperidin-2-yl)methyl)acetamide (84)

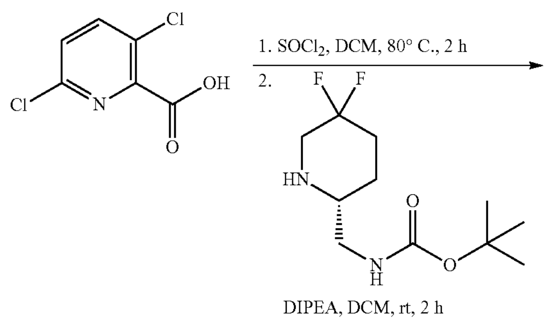

-continued

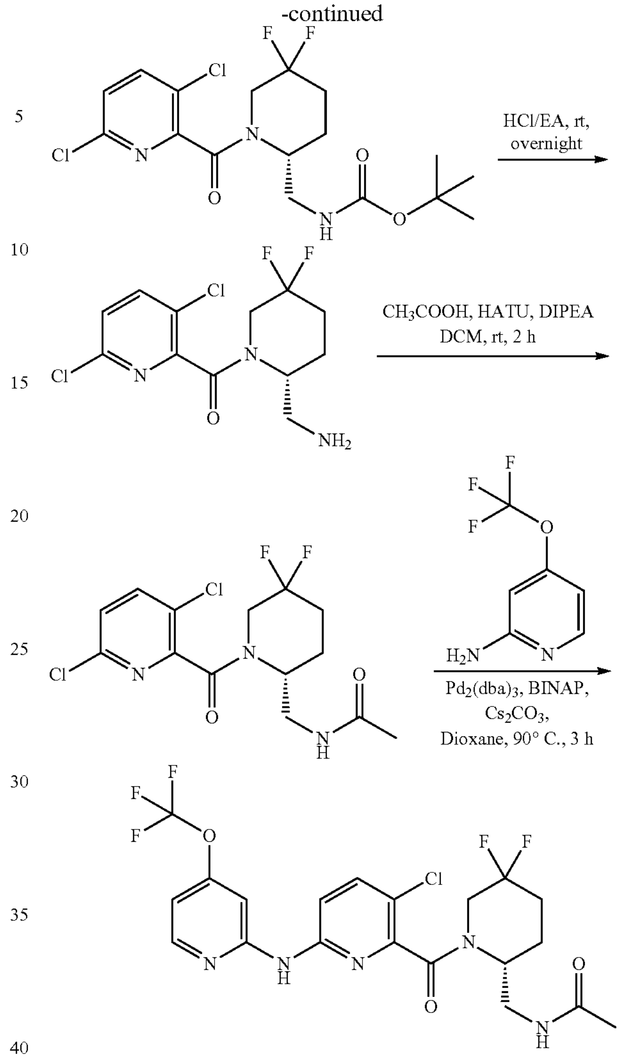

Step 1: (R)-((1-(3,6-dichloropyridine-2-carbonyl)-5,5-difluoropiperidin-2-yl)methyl)t-butyl carbamate (85)

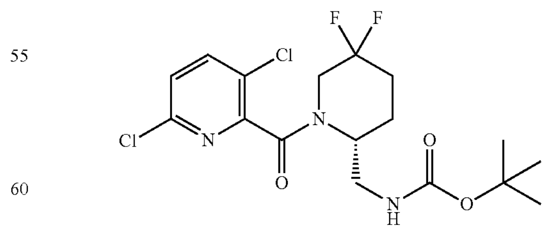

(R)-((1-(3,6-dichloropyridine-2-carbonyl)-5,5-difluoropiperidin-2-yl)methyl)t-butyl carbamate was obtained by a method similar to the synthesis method of Compound 65 in Example 49. LC-MS (m/z): 424.3 [M+H]+.

Step 2: (R)-(2-(aminomethyl)-5,5-difluoropiperidin-1-yl)(3,6-dichloropyridin-2-yl)methanone (86)

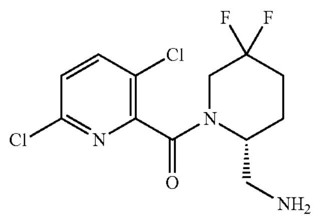 [SMILES: NC[C@H]1CCC(F)(F)CN1C(=O)c1nc(Cl)ccc1Cl]

With stirring, (R)-((1-(3,6-dichloropyridine-2-carbonyl)-5,5-difluoropiperidin-2-yl)methyl)t-butyl carbamate (0.2 g, 471.40 μmol, 1 eq.) was dissolved in DCM (3 mL), and a solution of HCl in EA (4 M, 2 mL, 16.97 eq.) was added at a temperature of an ice water bath. The reaction mixture was stirred overnight at room temperature. The mixture was neutralized with a saturated aqueous solution of $NaHCO_3$ and extracted with DCM. The solvent was removed by being evaporated in vacuum to obtain the title compound (140 mg, with a yield of 91.6%). LC-MS (m/z): 324.2 $[M+H]^+$.

Step 3: (R)—N-((1-(3,6-dichloropyridine-2-carbonyl)-5,5-difluoropiperidin-2-yl)methyl) acetamide (87)

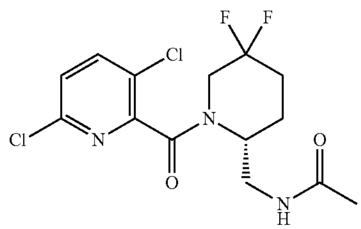 [SMILES: CC(=O)NC[C@H]1CCC(F)(F)CN1C(=O)c1nc(Cl)ccc1Cl]

With stirring, $CH_3COOH$ (27.79 mg, 462.74 μmol, 1.5 eq.), HATU (175.95 mg, 462.74 μmol, 1.5 eq.) and DIPEA (119.61 mg, 925.49 μmol, 3.0 eq.) were dissolved in DCM (5 mL), and a solution of (R)-(2-(aminomethyl)-5,5-difluoropiperidin-1-yl)(3,6-dichloropyridin-2-yl) methanone (100.00 mg, 308.50 μmol, 1.0 eq.) in DCM (2 mL) was added dropwise at room temperature. The reaction mixture was stirred for 2 h at room temperature. The mixture was washed with brine and extracted with DCM. The crude product was purified through reverse phase column chromatography (MeCN/water=30%) to obtain the title compound (10.5 mg, 64.0%). LC-MS (m/z): 366.2 $[M+H]^+$.

Step 4: (R)—N-((1-(3-chloro-6-((4-(trifluoromethoxy)pyridin-2-yl)amino)pyridine-2-carbonyl)-5,5-difluoropiperidin-2-yl)methyl)acetamide (84)

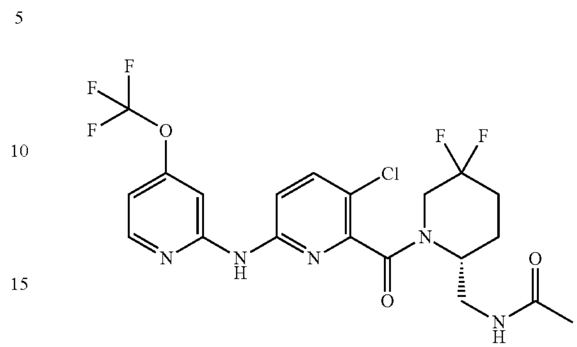

(R)—N-((1-(3,6-dichloropyridine-2-carbonyl)-5,5-difluoropiperidin-2-yl)methyl)acetamide (70.00 mg, 191.16 μmol, 1.0 eq.), 4-(trifluoromethoxy)pyridin-2-amine (37.45 mg, 210.27 μmol, 1.1 eq.), $Pd_2(dba)_3$ (8.76 mg, 9.56 μmol, 0.05 eq.), BINAP (11.90 mg, 19.12 μmol, 0.1 eq.) and $Cs_2CO_3$ (124.57 mg, 382.32 μmol, 2.0 eq.) were suspended in 1,4-dioxane (3.0 mL). The resulting mixture was heated to 90° C. to react for 3 h under a nitrogen atmosphere. The reaction solution was purified through column chromatography (Biotage Rening Flash 10 g, EtOAc/n-Hep=100%) and subjected to reverse phase column chromatography (MeCN/water=60%) to obtain the title compound (53 mg, 54.6%). $^1H$ NMR (400 MHz, DMSO-$d_6$) δ 10.45 (s, 0.2H), 10.39 (s, 0.8H), 8.37-8.35 (m, 1H), 8.08 (t, J=6.2 Hz, 0.3H), 7.91-7.86 (m, 1.7H), 7.79 (s, 1H), 7.74 (d, J=9.0 Hz, 0.3H), 7.70 (d, J=9.0 Hz, 0.7H), 6.96-6.92 (m, 1H), 4.83-4.75 (m, 0.3H), 4.69 (t, J=13.2 Hz, 0.7H), 3.77-3.38 (m, 3H), 3.30-3.28 (m, 1H), 2.36-1.78 (m, 4H), 1.72 (s, 3H). LC-MS (m/z): 507.8 $[M+H]^+$.

Biological Evaluation

Experimental Example 1 Determination of CDK9, CDK2, CDK7 and CDK1 Kinase Activity Inhibition CDK9 kinase was manufactured by the company or commercially available. CDK1, CDK2 and CDK7 were purchased from Carna Biosciences, Inc. ADP-Glo™ kit was purchased from Promega Corporation. Dithiothreitol (DTT), Tween-20, dimethylsulfoxide (DMSO), bovine serum albumin (BSA) and Tris base were obtained from Sigma at the available highest level of purity.

General procedures for CDK inhibition determination: The determination was performed in a buffer consisting of 50 μM DTT, 0.1% BSA, 40 mM Tris-HCl pH=7.5 and 20 mM $MgCl_2$. The compound dissolved in DMSO and CDK enzymes were diluted with the buffer. 1 μL of the compound solution in 5% DMSO and 2 μL of the CDK enzyme solution were added to a white low-volume 384-well microtiter plate and incubated for 20 min at room temperature. Ultra pure ATP and the substrate polypeptide (purchased from GenScript Biotech Corporation) were diluted together into the buffer and added to a mixed solution of the compound and the enzyme, 2 μL per well. They were incubated for 2 h at room temperature. Substrate and ATP reaction concentrations corresponding to different CDK enzymes are shown in Table 1.

TABLE 1

| | CDK1 | CDK2 | CDK7 | CDK9 |
|---|---|---|---|---|
| Enzyme concentration (μg/mL) | 0.2 | 0.4 | 2.0 | 1.6 |
| Polypeptide substrate sequence | GGGPATPKKAKKL (SEQ ID NO. 1) | YSPTSPSYSPTSPSYSPTSPSKKKK (SEQ ID NO. 2) | YSPTSPSYSPTSPSYSPTSPSKKKK (SEQ ID NO. 3) | YSPTSPSYSPTSPSYSPTSPSKKKK (SEQ ID NO. 4) |
| Polypeptide substrate concentration (μM) | 50 | 160 | 160 | 160 |
| ATP concentration (μM) | 50 | 10 | 10 | 10 |

After the reaction was completed, 5 μL of ADP-Glo™ reagent was added to each well and incubated for 40 min at room temperature, and then 10 μL of test reagent was added to each well and incubated for 30 mi at room temperature. Chemical luminescence values were measured by using a Tecan (Männedorf, Switzerland) multifunctional plate reader Spark for plate reading. The $IC_{50}$ value of the inhibitor was obtained by fitting the chemical luminescence intensity ratio in the S-shaped dosage reaction curve using Prism 7 (La Jolla, 15 CA) relative to the concentration of the inhibitor.

$IC_{50}$ values of the representative compounds of the present application for CDK9, CDK2, CDK7 and CDK1 kinase activity inhibition determination are shown in Table 2.

TABLE 2

| Compound | CDK9 (nM) | CDK2 (nM) | CDK7 (nM) | CDK1 (nM) |
|---|---|---|---|---|
| BAY1251152 | 6.9 | 811 | 4290 | 570 |
| AZD4573 | 3.6 | 18.6 | 31.4 | 8.3 |
| Dinaciclib | 6 | 8 | 19.4 | 4 |
| 1 | 4.9 | 36.7 | 1952 | |
| 5 | 5.8 | 217 | 2597 | 350 |
| 8 | 8.9 | 2592 | 8377 | 8730 |
| 9 | 7.8 | 8450 | >10000 | >10000 |
| 10 | 361 | >10000 | 9858 | >10000 |
| 11 | 5.1 | 368 | 4352 | 755 |
| 12 | 163 | >10000 | >10000 | |
| 13 | 64 | 704 | >10000 | |
| 14 | 107 | 1596 | 1884 | |
| 15 | 4.3 | 12 | >10000 | 503 |
| 16 | 54.6 | 6351 | >10000 | |
| 17 | 19.2 | 2873 | | >10000 |
| 18 | 33.6 | 3311 | | |
| 19 | 9 | 48.7 | 7776 | 106 |
| 20 | 44.1 | 1232 | | |
| 21 | 182 | >10000 | | |
| 22 | 35 | >10000 | | >10000 |
| 23 | 4620 | >10000 | | |
| 24 | 7.1 | 408 | 8764 | >10000 |
| 25 | 218 | >10000 | | |
| 26 | 17.8 | 3614 | | |
| 27 | 5.8 | 144 | 4567 | 426 |
| 28 | 9.4 | 1255 | | |
| 29 | 5709 | >10000 | | |
| 30 | 11.7 | 99.3 | 3180 | 291 |
| 31 | 3.7 | 180 | 7033 | 1470 |
| 32 | 11.6 | 305 | 780 | 1395 |
| 33 | 38 | 1419 | >10000 | |
| 34 | 3 | 30 | 479 | 261 |
| 35 | 5 | 6841 | >10000 | >10000 |
| 36 | 231 | >10000 | >10000 | |
| 37 | 26.6 | 3561 | | |
| 38 | 267 | 447 | | |
| 41 | 245 | 9264 | >10000 | |

TABLE 2-continued

| Compound | CDK9 (nM) | CDK2 (nM) | CDK7 (nM) | CDK1 (nM) |
|---|---|---|---|---|
| 42 | 34.8 | 361 | | |
| 43 | 167 | >10000 | | |
| 44 | 23 | 679 | | |
| 45 | 19.9 | 884 | | |
| 46 | 86.9 | 770 | | 4125 |
| 47 | 119 | 844 | | |
| 48 | 16.4 | 2866 | | |
| 49 | 107 | 3208 | | |
| 50 | 573 | >10000 | | |
| 51 | 7.7 | 1271 | | |
| 52 | 14.6 | 658 | | |
| 53 | 19.7 | >10000 | | >10000 |
| 55 | 28.3 | >10000 | | |
| 56 | 7.7 | 924 | | 3746 |
| 58 | >10000 | >10000 | | |
| 60 | 70.5 | 797 | | |
| 62 | 531 | >10000 | | |
| 64 | 6.3 | 120 | | |
| 66 | 647 | 1256 | | |
| 67 | 6.8 | 61.2 | 656 | 140 |
| 68 | 265 | >10000 | | >10000 |
| 72 | 1312 | >10000 | | |
| 76 | 18.4 | 5784 | | |
| 80 | 7.2 | 258 | | |
| 84 | 6.2 | 577 | | |

Note:
Blank represents unmeasured.

The results show that the representative compounds of the present application can effectively inhibit the kinase activity of CDK9 and their $IC_{50}$ values are comparable to that of the clinical candidate compound. Meanwhile, the inhibitory activity of the representative compounds of the present application for the critical cell cycle regulatory kinases CDK1 and CDK2 is much lower than that of the reference clinical candidate compound, the representative compounds show good selectivity, and some compounds achieve thousands of times higher selectivity.

Experimental Example 2 Tumor Cell Proliferation Inhibition Experiment

An acute myeloid leukemia (AML) cell line (MOLM-13) was purchased from NANJING COBIOER BIOSCIENCES CO., LTD. An RPMI1640 medium and a penicillin-streptomycin double-antibody were purchased from ThermoFisher (Waltham, MA, USA). Certified fetal bovine serum (FBS) was purchased from Biological Industries (Israel). A Corning 384-well cell culture plate was purchased from CORNING (USA). Cell-Titer Glo® was purchased from Promega Corporation (Madison, WI, USA).

To evaluate the ability of the synthetic compound to inhibit the proliferation of MOLM-13 cells, MOLM-13 cells at an exponential growth stage were inoculated at a density of 500,000 cell/mL in the RPMI1640 medium containing 20% bovine serum and 1% penicillin-streptomycin double-antibody, and the 384-well plate contained 20 μL per well and placed overnight in an 37° C., 5% $CO_2$ incubator. Compound powder was dissolved in DMSO to prepare a storage mother liquor with a concentration of 2 mM, and 12 dilutions with three-fold gradient concentrations were further prepared. 1 μL of gradient-diluted DMSO solution was added to 99 μL of cell culture medium (the final maximum concentration of the compound in the assay was 10 uM and the final concentration of DMSO was 0.5%). 20 μL of compound solution in the medium was added at gradients to each cell-coated test well of the 384-well plate. After the compound solution was added, the 384-well plate was incubated for 16 h in a 37° C., 5% $CO_2$ incubator. Cell viability was determined by quantifying ATPs present in test wells using the CellTiter-Glo kit from Promega (Madison, WI, USA). After 20 minutes of incubation, readings were obtained under a chemical luminescence procedure using Tecan's Spark multifunctional plate reader. The concentration ($IC_{50}$ value) of the compound at which the cell survival rate was inhibited by 50% was determined using an S-shaped dosage response model (variable slope, four parameters) in Prism 7 (LaJolla, CA).

The $IC_{50}$ values of the representative compounds of the present application in the MOLM-13 cell proliferation inhibitory activity inhibition assay are shown in Table 3.

TABLE 3

| Compound | MOLM-13 (nM) |
|---|---|
| BAY1251152 | 118 |
| AZD4573 | 17.1 |
| 1 | 24.8 |
| 5 | 27.9 |
| 11 | 45.3 |
| 19 | 24.2 |
| 24 | 70.9 |
| 27 | 22.1 |
| 28 | 133 |
| 30 | 11.3 |
| 34 | 63.1 |
| 47 | 938 |
| 48 | 683 |
| 51 | 112 |
| 56 | 180 |
| 60 | 894 |
| 64 | 120 |
| 67 | 66.8 |
| 80 | 198 |
| 84 | 58.6 |

The results show that the representative compounds of the present application can effectively inhibit the proliferation of MOLM-13 cells, and the $IC_{50}$ of most representative compounds is comparable to that of the clinical candidate compound AZD4573 and significantly higher than that of the clinical candidate compound BAY1251152.

What is claimed is:

1. A compound represented by general Formula (Id):

(Id)

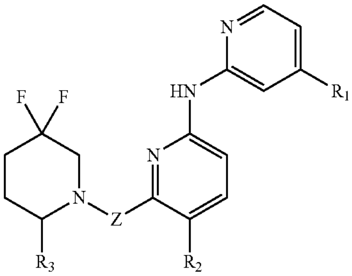

or a tautomer, a mesomer, a racemate, an enantiomer, a diastereomer, or a pharmaceutically acceptable salt thereof;

wherein Z is selected from —C(O)—, —$CH_2$—, —$S(O)_2$—, —NH—, or —C(O)NH—;

$R_1$ is selected from hydrogen, $C_1$ to $C_6$ alkyl, $C_2$ to $C_6$ alkenyl, $C_2$ to $C_6$ alkynyl, halogenated $C_1$ to $C_6$ alkyl, halogenated $C_2$ to $C_6$ alkenyl, halogenated $C_2$ to $C_6$ alkynyl, halogen, cyano, nitro, —C(O)$NR_4R_5$, —C(O)$R_4$, —C(O)$OR_4$, —$OR_4$, —OC(O)$R_4$, —OC(O)$OR_4$, —OC(O)$NR_4R_5$, —$NR_4R_5$, —$SR_4$, —S(O)$R_4$, —$S(O)_2R_4$, —$(CH_2)_n$OH, or a 3- to 10-membered saturated or unsaturated ring containing 0 to 3 heteroatoms, wherein the 3- to 10-membered saturated or unsaturated ring containing 0 to 3 heteroatoms is optionally substituted with 1 to 3 $R_4$;

$R_2$ is selected from hydrogen, $C_1$ to $C_6$ alkyl, $C_2$ to $C_6$ alkenyl, $C_2$ to $C_6$ alkynyl, halogenated $C_1$ to $C_6$ alkyl, halogenated $C_2$ to $C_6$ alkenyl, halogenated $C_2$ to $C_6$ alkynyl, halogen, cyano, nitro, —C(O)$NR_4R_5$, —C(O)$R_4$, —C(O)$OR_4$, —$OR_4$, —OC(O)$R_4$, —OC(O)$OR_4$, —OC(O)$NR_4R_5$, —$NR_4R_5$, —$(CH_2)_n NR_4R_5$, —$SR_4$, —S(O)$R_4$, —$S(O)_2R_4$, or —$(CH_2)_n$OH;

$R_3$ is selected from hydrogen, $C_1$ to $C_6$ alkyl, $C_2$ to $C_6$ alkenyl, $C_2$ to $C_6$ alkynyl, halogenated $C_1$ to $C_6$ alkyl, halogenated $C_2$ to $C_6$ alkenyl, halogenated $C_2$ to $C_6$ alkynyl, halogen, cyano, nitro, —C(O)$NR_4R_5$, —C(O)$R_4$, —C(O)$OR_4$, —$OR_4$, —OC(O)$R_4$, —OC(O)$OR_4$, —OC(O)$NR_4R_5$, —$NR_4R_5$, —$(CH_2)_n NR_4R_5$, —$SR_4$, —S(O)$R_4$, —$S(O)_2R_4$, or —$(CH_2)_n$OH;

each $R_4$ and each $R_5$ are independently selected from hydrogen, $C_1$ to $C_6$ alkyl, halogenated $C_1$ to $C_6$ alkyl, $C_3$ to $C_6$ cycloalkyl, halogenated $C_3$ to $C_6$ cycloalkyl, $C_3$ to $C_6$ heterocycloalkyl, halogenated $C_3$ to $C_6$ heterocycloalkyl, halogen, =O, —$(CH_2)_n$C(O)$NR_6R_7$, —C(O)$R_6$, —C(O)$OR_6$, —$OR_6$, —OC(O)$R_6$, —OC(O)$OR_6$, —OC(O)$NR_6R_7$, —$(CH_2)_n NR_6R_7$, —$SR_6$, —S(O)$R_6$, —$(CH_2)_n S(O)_2R_6$, —$(CH_2)$ OH, or —$(CH_2)_n$CN, respectively, or $R_4$ and $R_5$ together with adjacent atoms form a 5- to 6-membered saturated or unsaturated ring containing 0 to 3 heteroatoms, wherein the 5- to 6-membered saturated or unsaturated ring containing 0 to 3 heteroatoms is optionally substituted with 1 to 3 $R_6$;

each $R_6$ and each $R_7$ are independently selected from hydrogen, halogen, carbonyl, hydroxyl, cyano, nitro, $C_1$ to $C_6$ alkyl, halogenated $C_1$ to $C_6$ alkyl, $C_3$ to $C_6$ cycloalkyl, or halogenated $C_3$ to $C_6$ cycloalkyl, respectively; and each n is independently selected from 0, 1, 2, or 3.

2. The compound represented by general Formula (Id) according to claim 1, wherein Z is selected from —C(O)—, —$CH_2$—, or —NH—;

$R_1$ is selected from hydrogen, $C_1$ to $C_6$ alkyl, halogenated $C_1$ to $C_6$ alkyl, halogen, cyano, nitro, —C(O)$NR_4R_5$, —C(O)$OR_4$, —$OR_4$, or a 3- to 10-membered saturated or unsaturated ring containing 0 to 3 heteroatoms;

$R_2$ is selected from hydrogen, $C_1$ to $C_6$ alkyl, halogenated $C_1$ to $C_6$ alkyl, halogen, cyano, nitro, —C(O)$NR_4R_5$, —C(O) $R_4$, —C(O)$OR_4$, or —$OR_4$;

$R_3$ is selected from hydrogen, $C_1$ to $C_6$ alkyl, halogenated $C_1$ to $C_6$ alkyl, cyano, nitro, —C(O)$NR_4R_5$, —C(O) $R_4$, —C(O)$OR_4$, —$OR_4$, —$NR_4R_5$, or —$(CH_2)_n NR_4R_5$;

each $R_4$ and each $R_5$ are independently selected from hydrogen, $C_1$ to $C_6$ alkyl, halogenated $C_1$ to $C_6$ alkyl, $C_3$ to $C_6$ cycloalkyl, halogenated $C_3$ to $C_6$ cycloalkyl, $C_3$ to $C_6$ heterocycloalkyl, halogenated $C_3$ to $C_6$ heterocycloalkyl, halogen, —C(O) $R_6$, —C(O)$OR_6$, —$OR_6$, or —$(CH_2)_n S(O)_2R_6$, respectively, or $R_4$ and $R_5$ together with adjacent atoms form a 5- to 6-membered saturated or unsaturated ring containing 0 to 3 heteroatoms, wherein the 5- to 6-membered saturated or unsaturated ring containing 0 to 3 heteroatoms is optionally substituted with 1 to 3 $R_6$;

each $R_6$ and each $R_7$ are independently selected from hydrogen, halogen, carbonyl, hydroxyl, cyano, nitro, $C_1$ to $C_6$ alkyl, halogenated $C_1$ to $C_6$ alkyl, $C_3$ to $C_6$ cycloalkyl, or halogenated $C_3$ to $C_6$ cycloalkyl, respectively; and each n is independently selected from 0, 1, 2, or 3.

3. The compound represented by general Formula (Id) according to claim 1, wherein the compound represented by general Formula (Id) is a compound represented by general Formula (Ie):

(Ie)

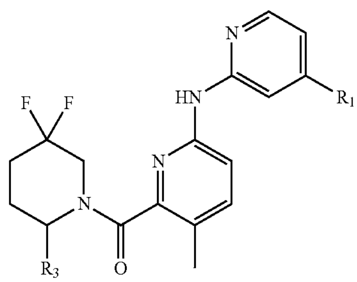

or a tautomer, a mesomer, a racemate, an enantiomer, a diastereomer, or a pharmaceutically acceptable salt thereof;

wherein $R_1$ and $R_3$ are defined as defined in claim 1.

4. The compound represented by general Formula (Id) according to claim 1, wherein $R_1$ is selected from cyano, nitro, halogen, trifluoromethyl, trifluoromethoxy, difluoromethyl, difluoromethoxy, monofluoromethyl, methyl, methoxy, or ethoxy.

5. The compound represented by general Formula (Id) according to claim 1, wherein $R_3$ is selected from halogen, $—CH_2NHC(O)CH_3$, or $—CH_2NH_2$.

6. The compound represented by general Formula (Id) according to claim 1, wherein the compound represented by general Formula (Id) is selected from the following:

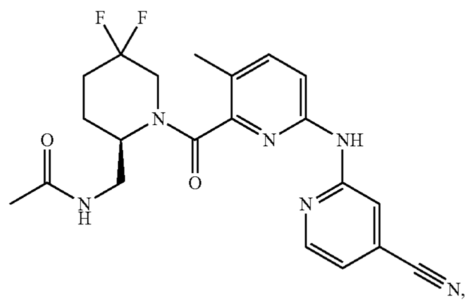

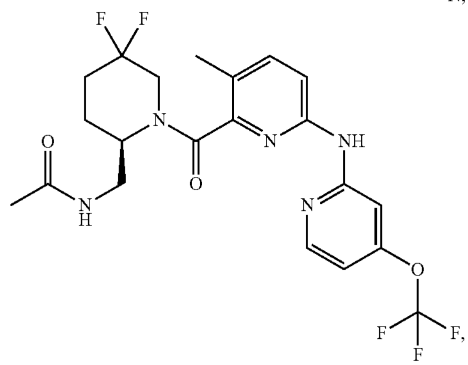

-continued

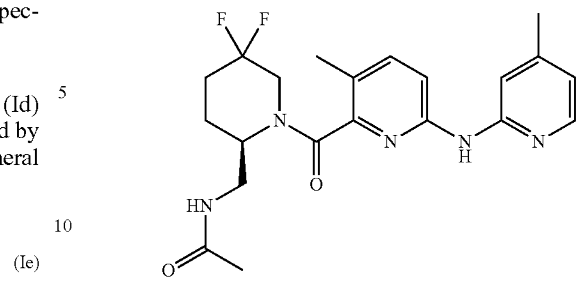

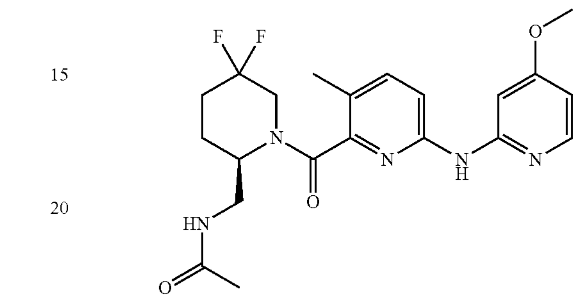

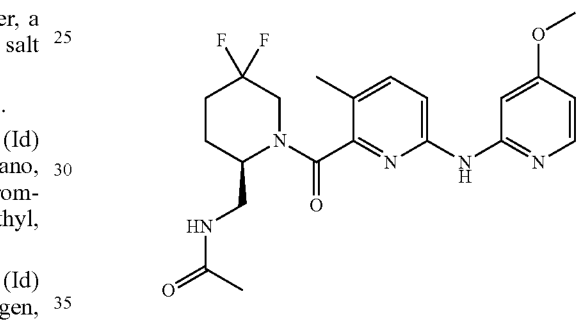

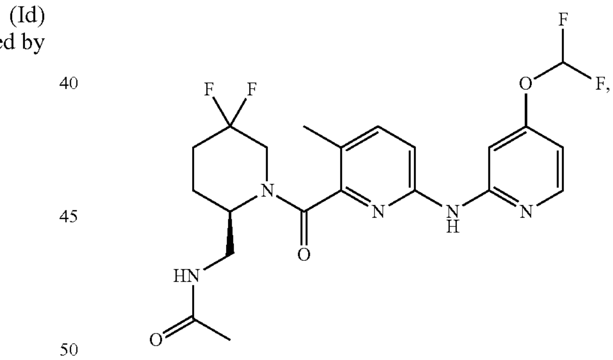

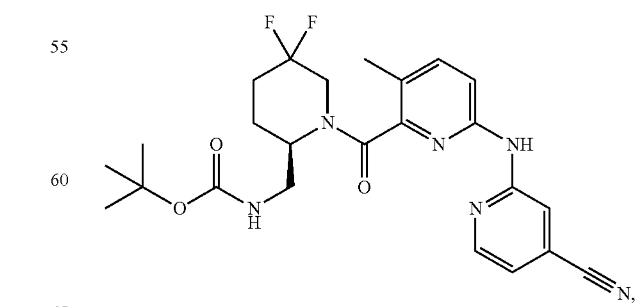

-continued
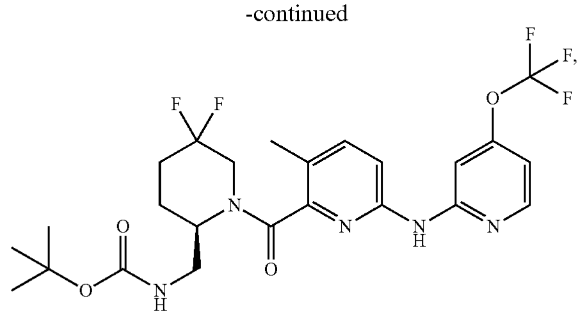
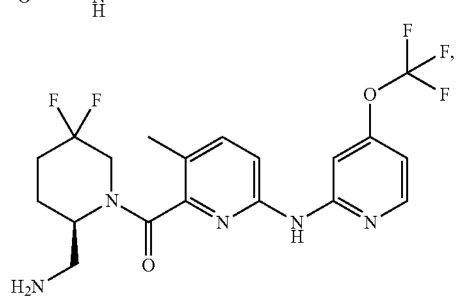
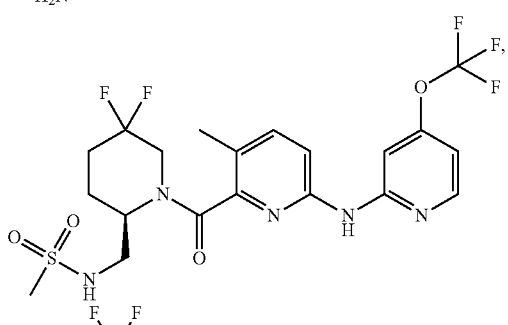
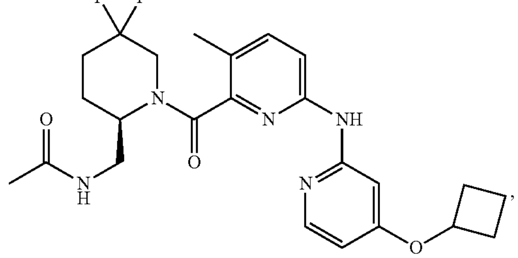
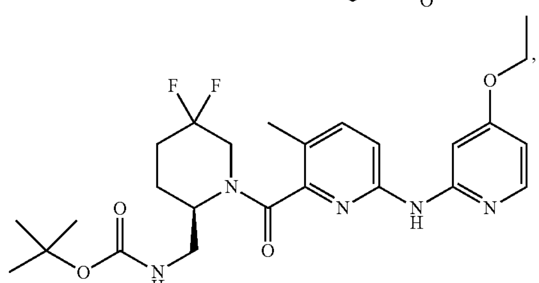
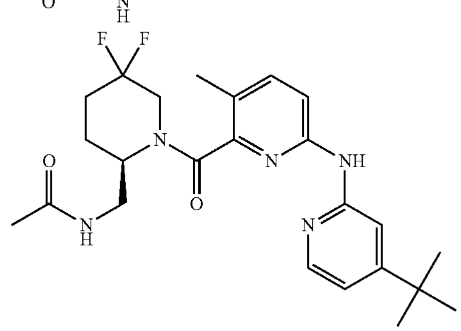
-continued
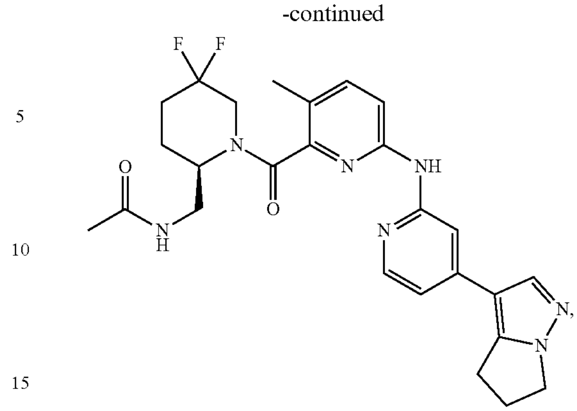
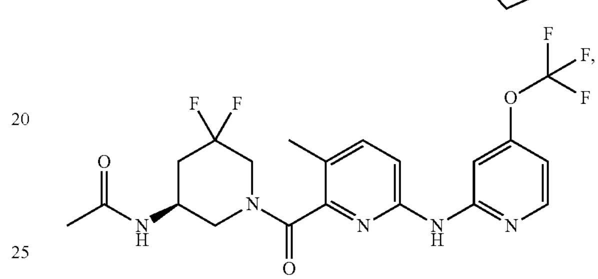
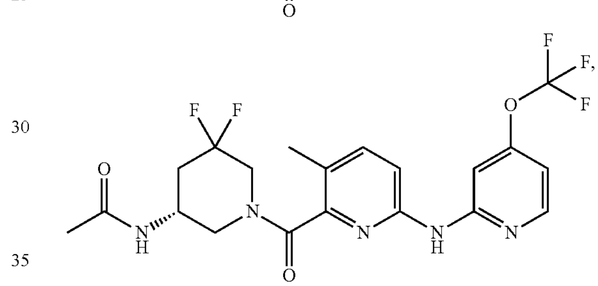
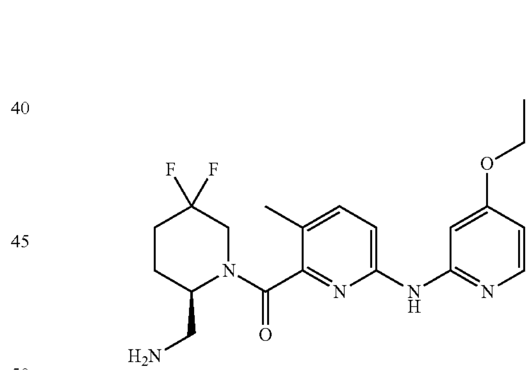
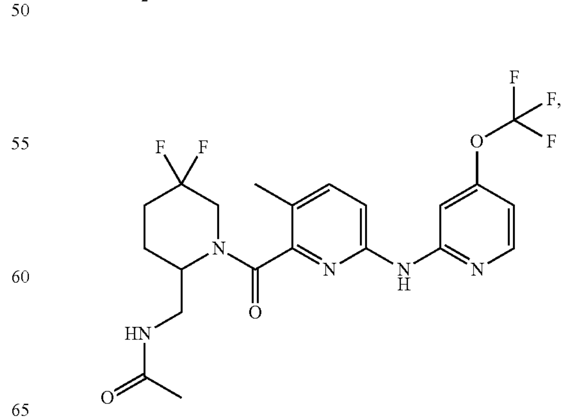

-continued
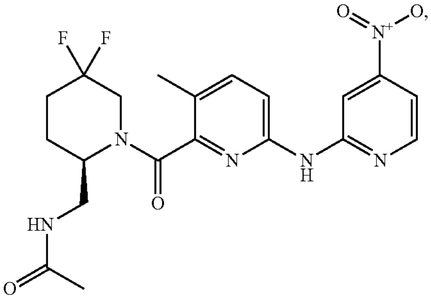
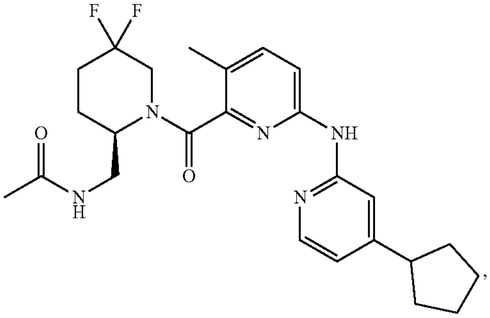
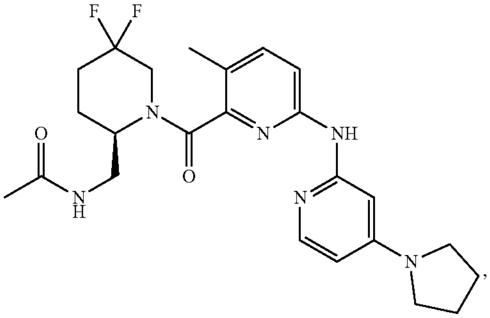
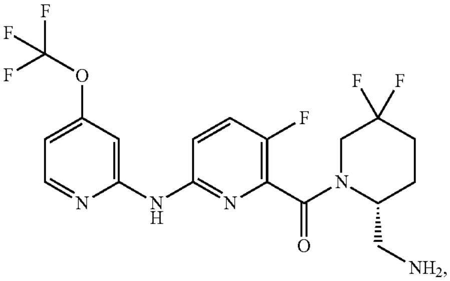
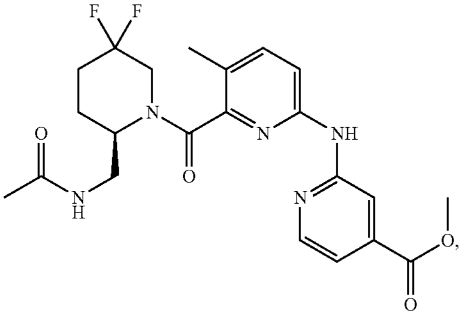
-continued
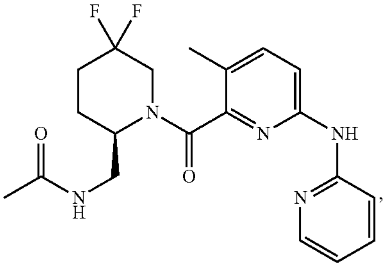
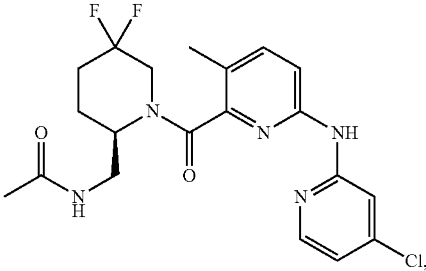
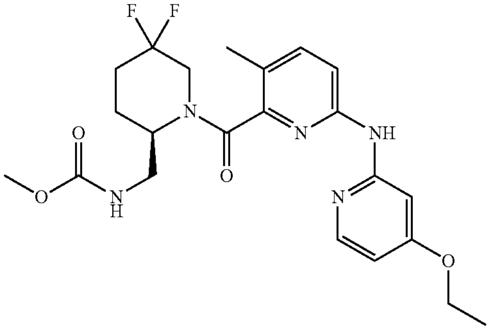
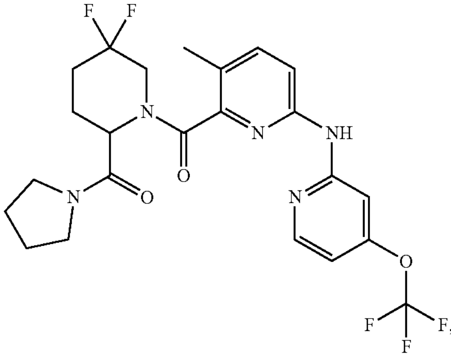
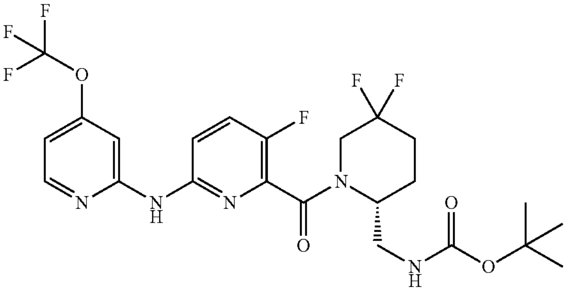

-continued
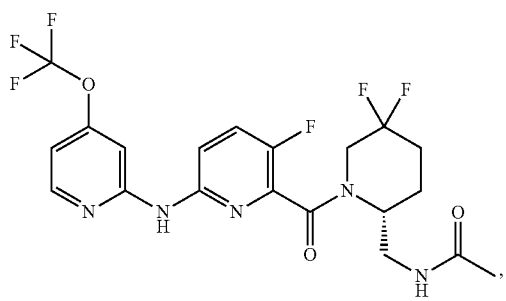 [SMILES: CC(=O)NC[C@H]1CCC(F)(F)CN1C(=O)c1nc(Nc2cc(OC(F)(F)F)ccn2)ccc1F]
,
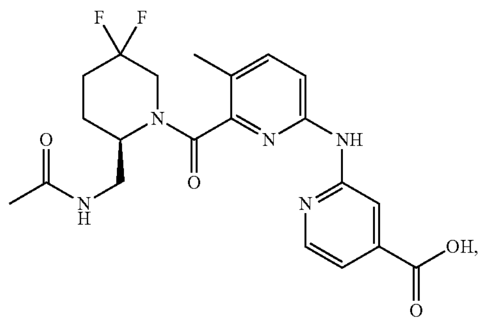
,
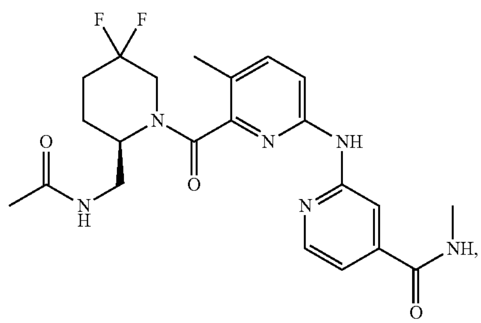
,
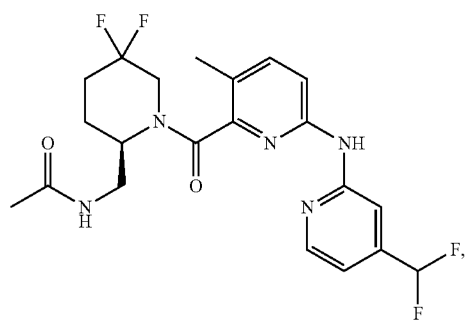
,
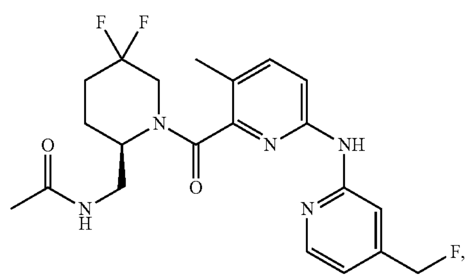
,
-continued
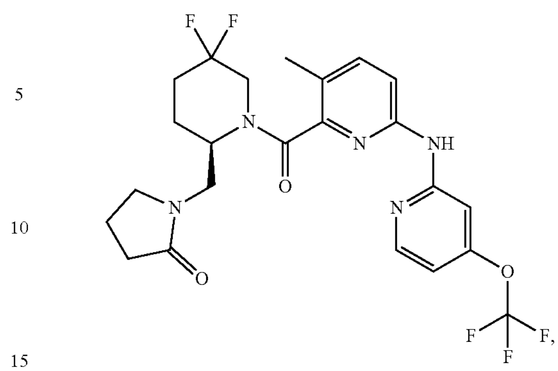
,
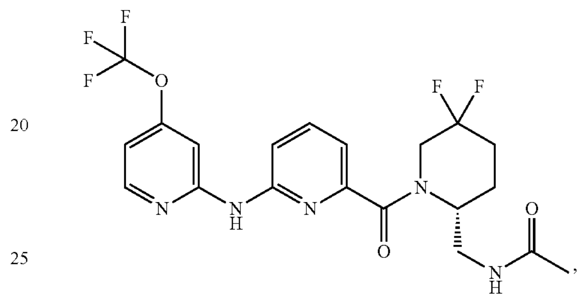
,
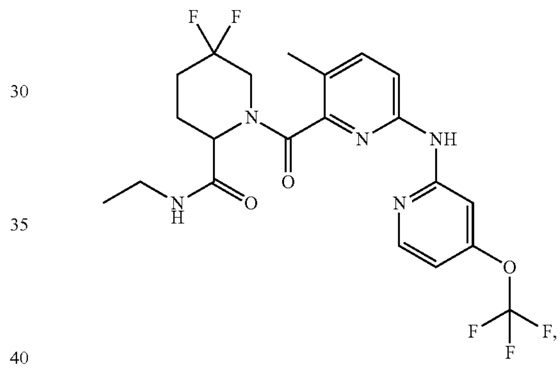
,
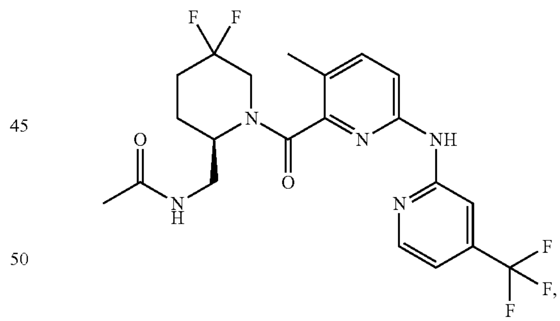
,
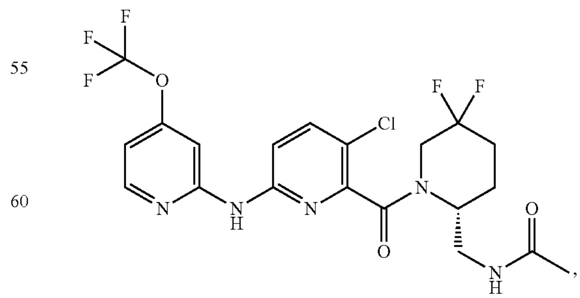
, -continued
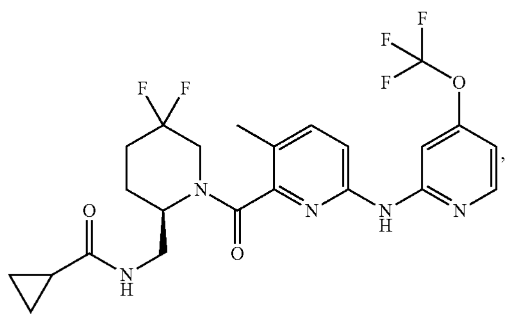
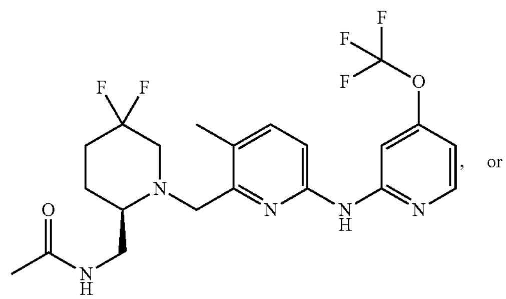
, or
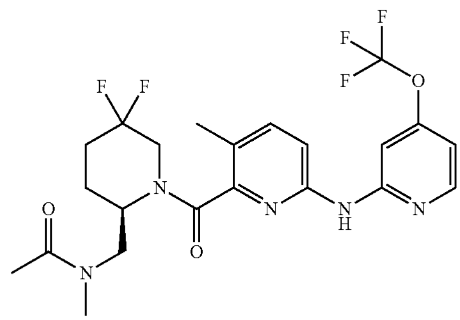
-continued
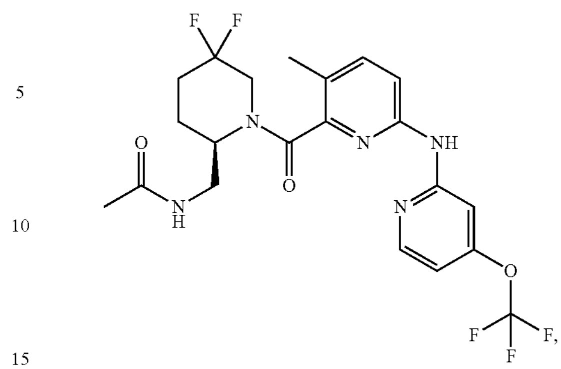
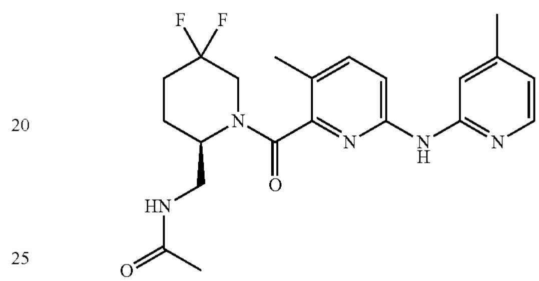
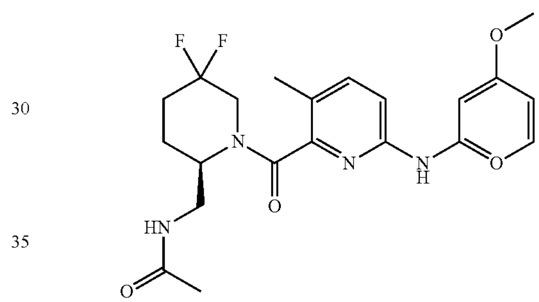
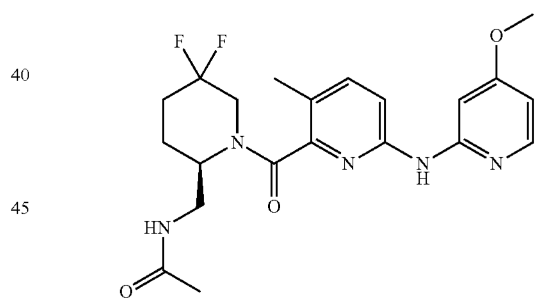
7. The compound represented by general Formula (Id) according to claim 1, wherein the compound represented by general Formula (Id) is selected from the following:
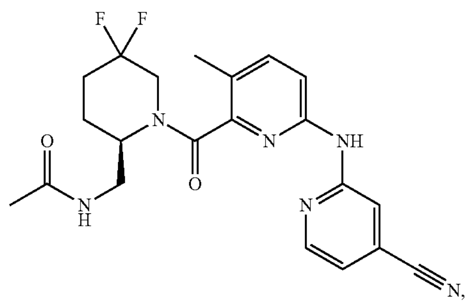
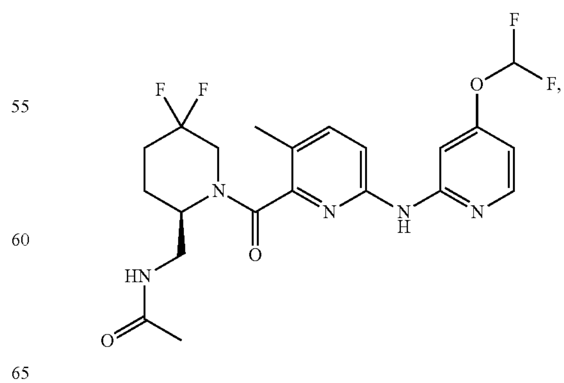

-continued
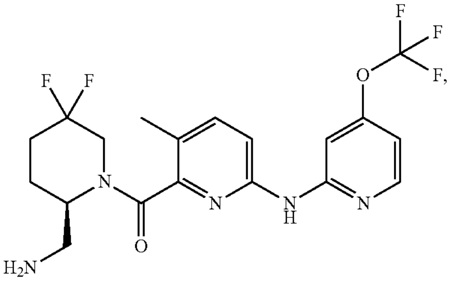
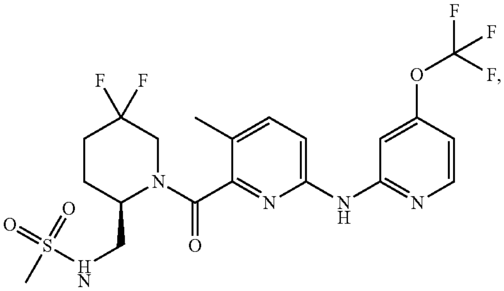
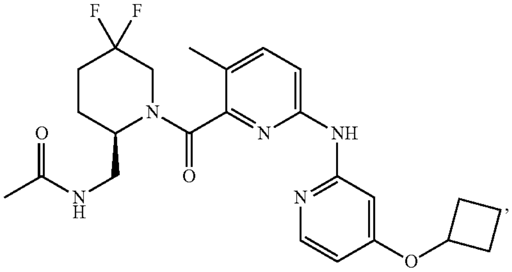
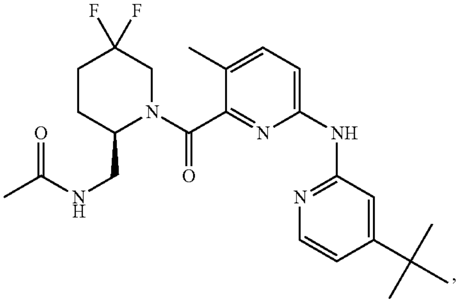
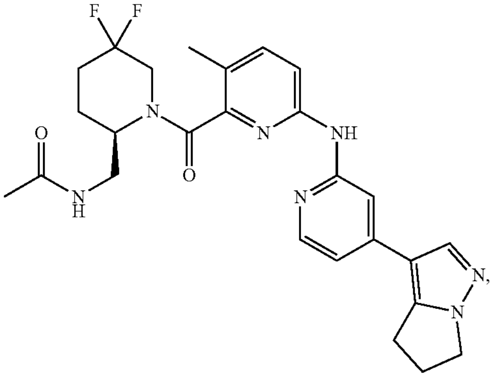
-continued
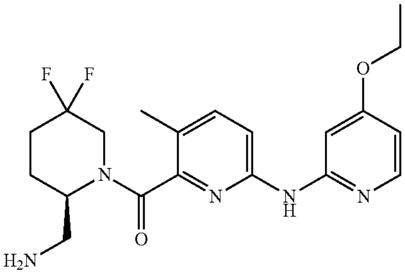
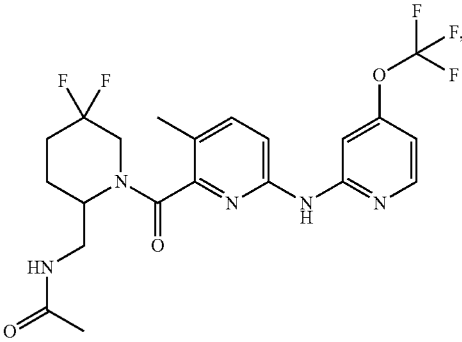
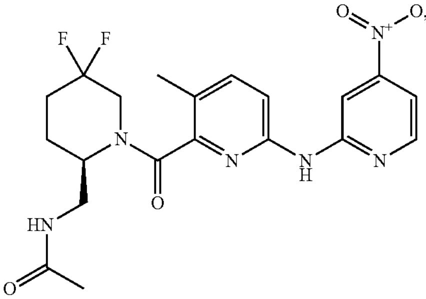
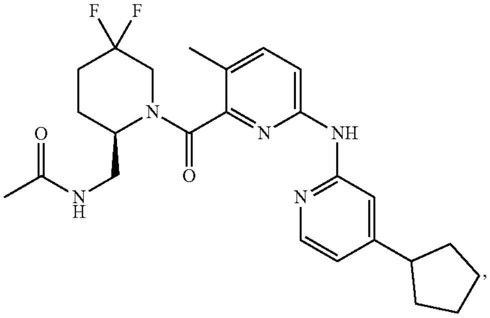
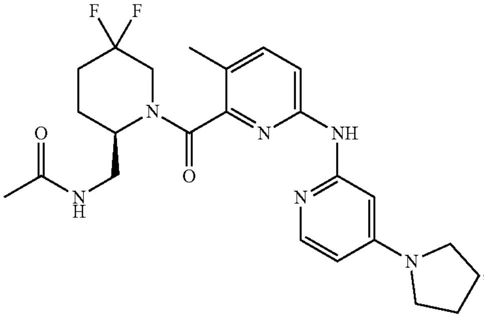

-continued
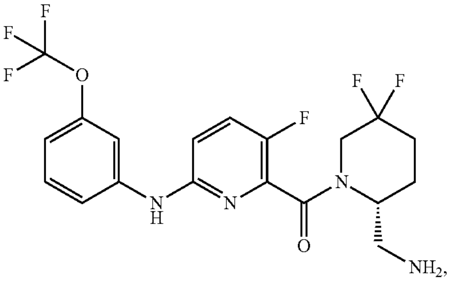
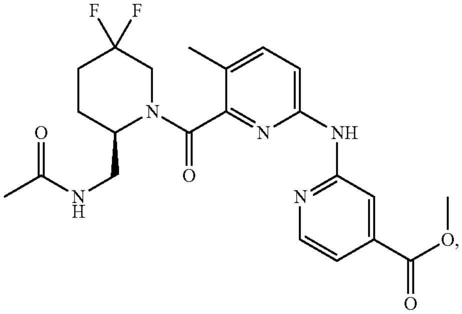
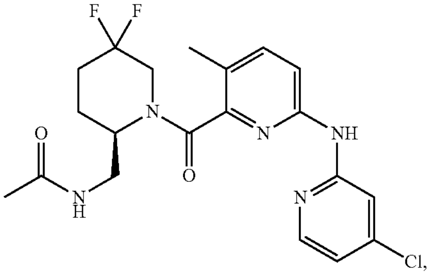
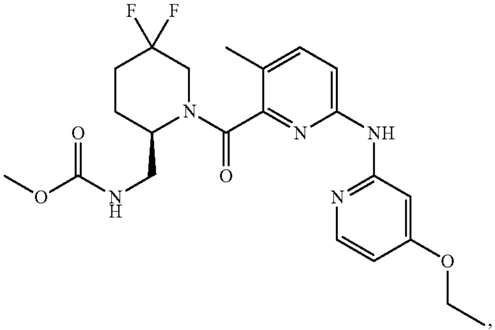
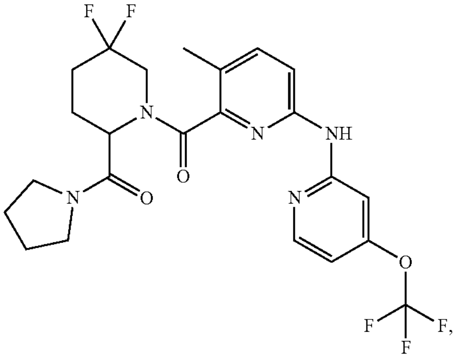
-continued
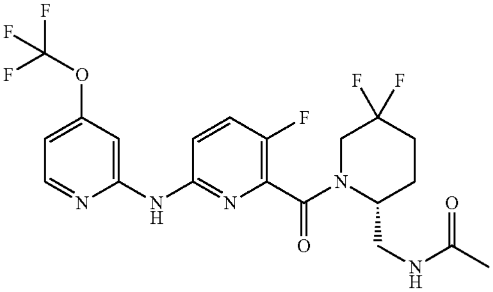
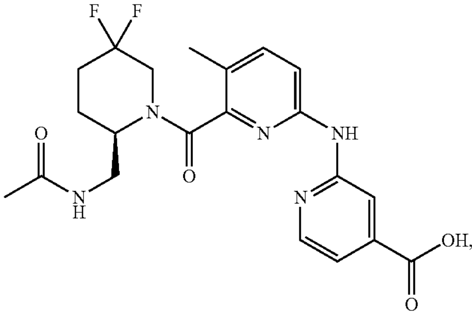
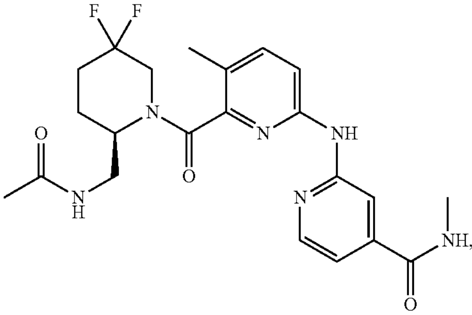
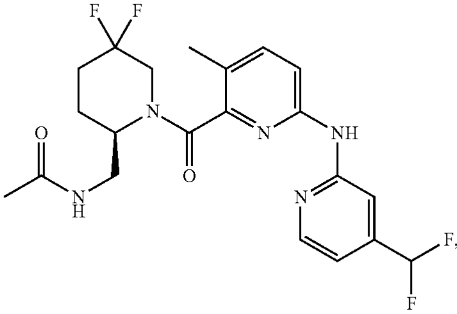
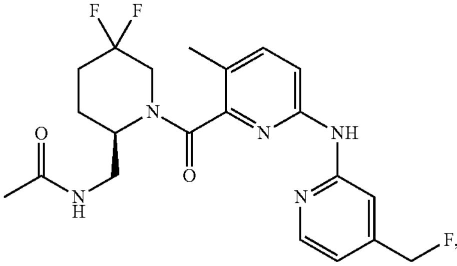

-continued
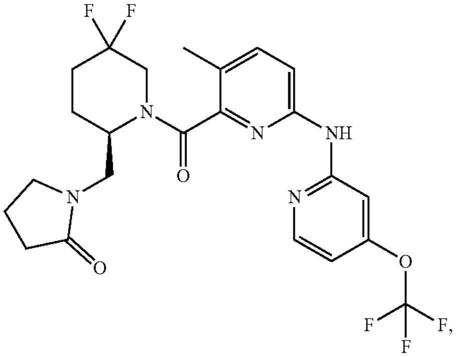
,
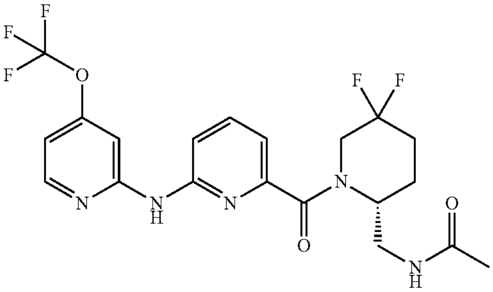
,
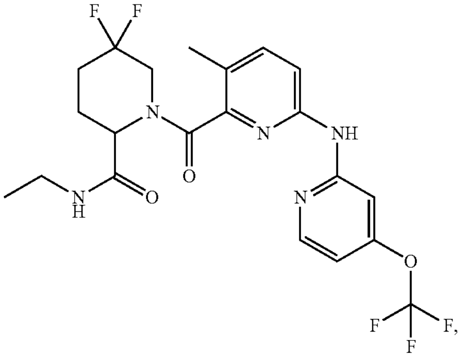
,
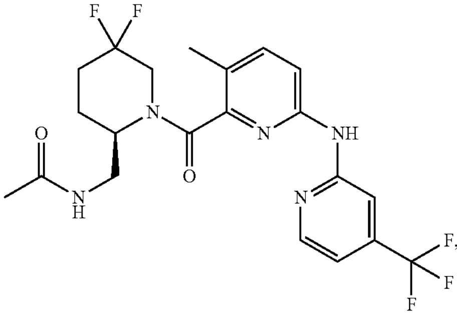
,
-continued
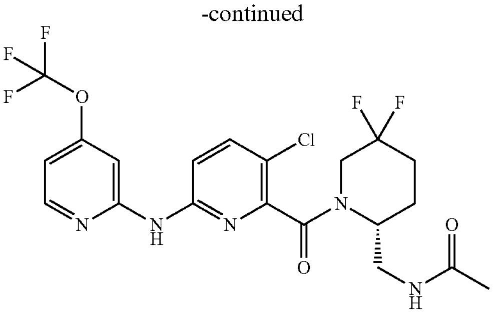
,
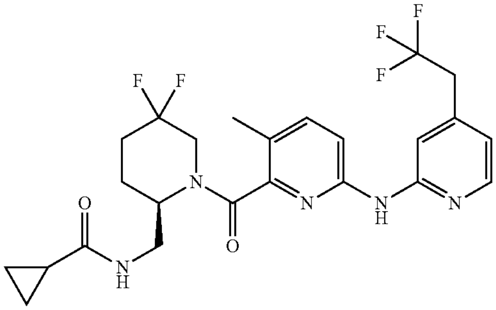
, or
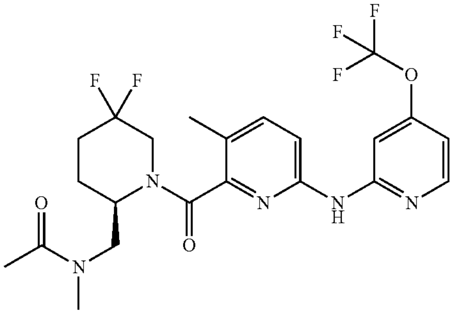
.
8. A pharmaceutical composition, comprising a therapeutically effective amount of the compound according to claim 1 or an isomer or a pharmaceutically acceptable salt thereof; and a pharmaceutically acceptable carrier or excipient.
* * * * *

SEQUENCE LISTING

```
<160> NUMBER OF SEQ ID NOS: 4

<210> SEQ ID NO 1
<211> LENGTH: 13
<212> TYPE: PRT
<213> ORGANISM: Artificial Sequence
<220> FEATURE:
<223> OTHER INFORMATION: CDK1

<400> SEQUENCE: 1

Gly Gly Gly Pro Ala Thr Pro Lys Lys Ala Lys Lys Leu
1               5                   10


<210> SEQ ID NO 2
<211> LENGTH: 25
<212> TYPE: PRT
<213> ORGANISM: Artificial Sequence
<220> FEATURE:
<223> OTHER INFORMATION: CDK2

<400> SEQUENCE: 2

Tyr Ser Pro Thr Ser Pro Ser Tyr Ser Pro Thr Ser Pro Ser Tyr Ser
1               5                   10                  15

Pro Thr Ser Pro Ser Lys Lys Lys Lys
            20                  25


<210> SEQ ID NO 3
<211> LENGTH: 25
<212> TYPE: PRT
<213> ORGANISM: Artificial Sequence
<220> FEATURE:
<223> OTHER INFORMATION: CDK7

<400> SEQUENCE: 3

Tyr Ser Pro Thr Ser Pro Ser Tyr Ser Pro Thr Ser Pro Ser Tyr Ser
```

-continued

```
1               5                   10                  15

Pro Thr Ser Pro Ser Lys Lys Lys Lys
            20                  25
```

<210> SEQ ID NO 4
<211> LENGTH: 25
<212> TYPE: PRT
<213> ORGANISM: Artificial Sequence
<220> FEATURE:
<223> OTHER INFORMATION: CDK9

<400> SEQUENCE: 4

```
Tyr Ser Pro Thr Ser Pro Ser Tyr Ser Pro Thr Ser Pro Ser Tyr Ser
1               5                   10                  15

Pro Thr Ser Pro Ser Lys Lys Lys Lys
            20                  25
```